(12) United States Patent
Carter et al.

(10) Patent No.: US 7,582,624 B2
(45) Date of Patent: Sep. 1, 2009

(54) BENZODIAZEPINE DERIVATIVES AND PHARMACEUTICAL COMPOSITIONS CONTAINING THEM

(75) Inventors: Malcolm Carter, London (GB); Philip Chambers, London (GB); Verity Dowdell, London (GB); Elisa Ann Henderson, London (GB); Richard David Kelsey, London (GB); Debra Taylor, London (GB); Stanley Tyms, London (GB); Lara Wilson, London (GB)

(73) Assignee: Arrow Therapeutics Limited, London (GB)

( * ) Notice: Subject to any disclaimer, the term of this patent is extended or adjusted under 35 U.S.C. 154(b) by 238 days.

(21) Appl. No.: 10/528,250

(22) PCT Filed: Sep. 22, 2003

(86) PCT No.: PCT/GB03/04050

§ 371 (c)(1),
(2), (4) Date: Jun. 21, 2005

(87) PCT Pub. No.: WO2004/026843

PCT Pub. Date: Apr. 1, 2004

(65) Prior Publication Data

US 2006/0040923 A1    Feb. 23, 2006

(30) Foreign Application Priority Data

Sep. 20, 2002 (GB) .................................. 0221923.6
Jan. 29, 2003 (GB) .................................. 0302078.1

(51) Int. Cl.
*C07D 243/24* (2006.01)
*C07D 409/12* (2006.01)
*C07D 405/12* (2006.01)
*C07D 403/12* (2006.01)
*A61K 31/5513* (2006.01)

(52) U.S. Cl. ...................................... 514/221; 540/509
(58) Field of Classification Search .................. 540/509; 514/221
See application file for complete search history.

(56) References Cited

U.S. PATENT DOCUMENTS

| 3,344,136 A | * | 9/1967 | Childress et al. | ............ | 540/509 |
| 4,628,084 A | * | 12/1986 | Bock et al. | .................. | 540/509 |
| 4,988,692 A | | 1/1991 | Gasc et al. | | |

(Continued)

FOREIGN PATENT DOCUMENTS

| CN | 1338456 | 3/2002 |
| EP | 0 167 919 A2 | 1/1986 |
| EP | 0 284 256 A1 | 9/1988 |
| EP | 0 421 802 A2 | 4/1991 |
| EP | 0 434 364 A2 | 6/1991 |
| EP | 0 475 231 A1 | 3/1992 |
| EP | 0491218 A1 | 6/1992 |
| EP | 0 508 797 A1 | 10/1992 |
| EP | 0 508 798 A1 | 10/1992 |
| EP | 0 523 845 A2 | 1/1993 |
| EP | 0 638 560 A1 | 2/1995 |

(Continued)

OTHER PUBLICATIONS

Haradahira et al. (Nuclear Medicine and Biology (1998), 25(3), 203-208).*

(Continued)

*Primary Examiner*—Bruck Kifle
(74) *Attorney, Agent, or Firm*—McCarter & English, LLP; Elizabeth A. Hanley, Esq.; Jermaine A. Lawrence, Esq.

(57) ABSTRACT

Benzodiazepine derivative of formula (I), and pharmaceutically acceptable salts thereof, are found to be active against RSV. Formula (I) Wherein: —$R^1$ represents $C_{1-6}$ alkyl, aryl or heteroaryl; —$R^2$ represents hydrogen or $C_{1-6}$ alkyl; —each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl) amino, nitro, cyano, —$CO_2R'$, —CONR'R", —NH—CO—R', —S(O)R', —S(O)$_2$R', —NH—S(O)$_2$R', —S(O)NR'R" or —S(O)$_2$NR'R" wherein each R' and R" is the same or different and represents hydrogen or $C_{1-6}$ alkyl; —n is from 0 to 3; $R^4$ represents hydrogen or $C_{1-6}$ alkyl; —$R^6$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-C(O)—C(O)—, heteroaryl-C(O)—C(O)—, carbocyclyl-C(O)—C(O)—, heterocyclyl-C(O)—C(O)— or, —$XR^6$; —X represents —CO—, —S(O)— or —S(O)$_2$—; and —$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)- or heterocyclyl-($C_{1-6}$ alkyl)-.

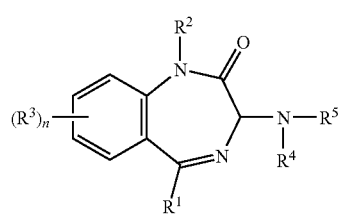

10 Claims, No Drawings

U.S. PATENT DOCUMENTS

| | | |
|---|---|---|
| 5,218,114 A | 6/1993 | Bock et al. |
| 5,220,018 A | 6/1993 | Bock et al. |
| 5,593,988 A | 1/1997 | Tahara et al. |
| 5,719,143 A | 2/1998 | Badorc et al. |
| 5,776,930 A | 7/1998 | Lynch, Jr. et al. |
| 6,436,971 B2 | 8/2002 | DeMarsh et al. |

FOREIGN PATENT DOCUMENTS

| | | |
|---|---|---|
| JP | 02-215774 | 8/1990 |
| KR | 212435 | 8/1999 |
| WO | WO 93/07129 | 4/1993 |
| WO | WO 93/11771 | 6/1993 |
| WO | WO 93/17011 A1 | 9/1993 |
| WO | WO 95/14470 | 6/1995 |
| WO | WO 95/14471 A1 | 6/1995 |
| WO | WO 98/00406 | 1/1998 |
| WO | WO 98/18473 | 5/1998 |
| WO | WO 99/19306 | 4/1999 |
| WO | WO 00/12547 A1 | 3/2000 |
| WO | WO 00/28947 | 5/2000 |
| WO | WO 00/66106 | 11/2000 |
| WO | WO 00/66106 A2 | 11/2000 |
| WO | WO 01/00611 A1 | 1/2001 |
| WO | WO 01/74783 A1 | 10/2001 |
| WO | WO 01/90084 A1 | 11/2001 |
| WO | WO 01/92235 A1 | 12/2001 |
| WO | WO 02/40023 A1 | 5/2002 |

OTHER PUBLICATIONS

Bock et al. (Journal of Medicinal Chemistry (1993), 36(26), 4276-92).*

Del Giudice, et al., Chemical Abstract 97:23755 CA, "Synthesis of 2- and 3-amino-1, 4-benzodiazepines," *Farmaco, Edizione Scientifica* 37(5):434-452 (1982).

Kelsey, R., et al., "Synthesis, Resolution and Evaluation of Small Molecule Inhibitors of Respiratory Syncytial Virus," Presented at 44th ICAAC, Oct. 30-Nov. 2, 2004.

* cited by examiner

BENZODIAZEPINE DERIVATIVES AND PHARMACEUTICAL COMPOSITIONS CONTAINING THEM

RELATED APPLICATIONS

This application is the U.S. National Stage of International Application No. PCT/GB03/004050, filed 22 Sep. 2003, published in English, and claims priority under 35 U.S.C. § 119 or 365 to Great Britain Application No. 0302078.1, filed 29 Jan. 2003 and Great Britain Application No. 0221923.6, filed 20 Sep. 2002.

The present invention relates to a series of benzodiazepine derivatives which are active against Respiratory Syncytial Virus (RSV).

RSV is a major cause of respiratory illness in patients of all ages. In adults, it tends to cause mild cold symptoms. In school-aged children, it can cause a cold and bronchial cough. In infants and toddlers it can cause bronchiolitis (inflammation of the smaller airways of the lungs) or pneumonia. It has also been found to be a frequent cause of middle ear infections (otitis media) in pre-school children. RSV infection in the first year of life has been implicated in the development of asthma during childhood.

Current anti-RSV therapy involves the use of a monoclonal antibody to RSV, called palivizumab. Such use of palivizumab is a prophylactic, rather than therapeutic, treatment of RSV. However, although this antibody is often effective, it is expensive. Indeed, its expense means that it is unavailable for many people in need of anti-RSV therapy. There is therefore an urgent need for effective alternatives to existing anti-RSV therapy.

It has now surprisingly been found that the particular benzodiazepine derivatives of the general formula (I) set out below are active against RSV.

Accordingly, the present invention provides, in a first embodiment, the use of a benzodiazepine derivative of formula (I), or a pharmaceutically acceptable salt thereof, in the manufacture of a medicament for use in treating or preventing an RSV infection

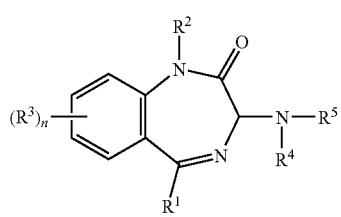

(I)

wherein:
$R^1$ represents $C_{1-6}$ alkyl, aryl or heteroaryl;
$R^2$ represents hydrogen or $C_{1-6}$ alkyl;
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl) amino, di($C_{1-6}$ alkyl)amino, nitro, cyano, —$CO_2R'$, —$CONR'R''$, —NH—CO—$R'$, —$S(O)R'$, —$S(O)_2R'$, —NH—$S(O)_2R'$, —$S(O)NR'R''$ or —$S(O)_2NR'R''$, wherein each R' and R" is the same or different and represents hydrogen or $C_{1-6}$ alkyl;
n is from 0 to 3;
$R^4$ represents hydrogen or $C_{1-6}$ alkyl;
$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-aryl-C(O)—C(O)—, heteroaryl-C(O)—C(O)—, carbocyclyl-C(O)—C(O)—, heterocyclyl-C(O)—C(O)— or —$XR^6$;
X represents —CO—, —S(O)— or —$S(O)_2$—; and
$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl), carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-$C_{1-6}$ alkyl)-, carbocyclyl-($C_{1-6}$ alkyl)- or heterocyclyl-($C_{1-6}$ alkyl)-. Typically, R' and R" are not both hydrogen.

Preferably, in the formula (I),
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl) amino, di($C_{1-6}$ alkyl)amino, nitro, cyano, —$CO_2R'$, —$CONR'R''$, —NH—CO—$R'$, —$S(O)R'$, —$S(O)_2R'$, —NH—$S(O)_2R'$ or —$S(O)NR'R''$, wherein each R' and R" is the same or different and represents hydrogen or $C_{1-6}$ alkyl;
$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —$XR^6$;
X represents —CO—, —S(O)— or —$S(O)_2$—; and
$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)- or heteroaryl-($C_{1-6}$ alkyl)-. Typically, R" and R" are not both hydrogen.

As used herein, a $C_{1-6}$ alkyl group or moiety is a lineal or branched alkyl group or moiety containing from 1 to 6 carbon atoms, such as a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a hydroxyalkyl group is typically a said alkyl group that is substituted by one or more hydroxy groups. Typically, it is substituted by one, two or three hydroxy groups. Preferably, it is substituted by a single hydroxy group. Preferred hydroxyalkyl groups are (monohydroxy)ethyl groups.

As used herein, an acyl group is a $C_{2-7}$ acyl group, for example a group —CO—R, wherein R is a said $C_{1-6}$ alkyl group.

As used herein, an aryl group is typically a $C_{6-10}$ aryl group such as phenyl or naphthyl. Phenyl is preferred. An aryl group may be unsubstituted or substituted at any position. Typically, it carries 0, 1, 2 or 3 substituents.

Suitable substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R", —S(O)R', —S(O)$_2$R', —S(O)NR'R", —S(O)$_2$NR'R" —NH—S(O)$_2$R' or —NH—CO—R', wherein each R' and R" is the same or different and represents hydrogen or $C_{1-6}$ alkyl. Examples of suitable substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R", —S(O)R', —S(O)$_2$R', —S(O)NR'R", —NH—S(O)$_2$R' or —NH—CO—R', wherein each R' and R" is the same or different and represents hydrogen or $C_{1-6}$ alkyl.

Preferred substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —S(O)R', —S(O)$_2$R' and —S(O)NR'R", wherein each R' and R" is the same or different and represents hydrogen or $C_{1-4}$ alkyl. Examples of preferred substituents on an aryl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano.

Particularly preferred substituents include fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino, di($C_{1-4}$ alkyl)amino, nitro, —$CO_2R'$, —S(O)$_2$R' and —S(O)$_2$NH$_2$, wherein R' represents $C_{1-2}$ alkyl. Examples of particularly preferred substituents include fluorine, chlorine, bromine, $C_{1-4}$ alkyl, $C_{1-4}$ alkoxy, $C_{1-4}$ haloalkyl and nitro.

As used herein, references to an aryl group include fused ring systems in which an aryl group is fused to a monocyclic carbocyclyl, heterocyclyl or heteroaryl group or to a fused group which is a monocyclic carbocyclyl, heterocyclyl or heteroaryl group which is fused to a phenyl ring. Typically, said fused ring systems are systems in which an aryl group is fused to a monocyclic carbocyclyl, heterocyclyl or heteroaryl group. Preferred such ring systems are those wherein an aryl group is fused to a fused group which is a monocyclic heterocyclyl or heteroaryl group or to a monocyclic carbocyclic group fused to a phenyl ring, in particular those wherein an aryl group is fused to a heterocyclyl or heteroaryl group. Examples of such fused ring systems are groups in which a phenyl ring is fused to a thienyl group or to a tetrahydrofuranyl group to form a benzothienyl or dihydrobenzofuranyl group. Further examples of such fused rings are groups in which a phenyl ring is fused to a dioxanyl group, a pyrrolyl group or a 2,3-dihydroinden-1-one group to form a benzodioxinyl, indolyl or a 9H-fluoren-9-one group.

As used herein, a carbocyclyl group is a non-aromatic saturated or unsaturated monocyclic hydrocarbon ring, typically having from 3 to 6 carbon atoms. Preferably it is a saturated hydrocarbon ring (i.e. a cycloalkyl group) having from 3 to 6 carbon atoms. Examples include cyclopropyl, cyclobutyl, cyclopentyl and cyclohexyl. It is preferably cyclopentyl or cyclohexyl. A cycloalkyl group may be unsubstituted or substituted at any position. Typically, it carries 0, 1, 2 or 3 substituents.

Suitable substituents on a carbocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, oxo, —$CO_2R'$, —CONR'R", —S(O)R', —S(O)$_2$R', —S(O)NR'R", —S(O)$_2$NR'R", —NH—S(O)$_2$R' or —NH—CO—R', wherein each R' and R" is the same or different and represents hydrogen or $C_{1-6}$ alkyl. Examples of suitable substituents on a carbocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R", —S(O)R', —S(O)$_2$R', —S(O)NR'R", —NH—S(O)$_2$R' or —NH—CO—R', wherein each R' and R" is the same or different and represents hydrogen or $C_{1-6}$ alkyl.

Preferred substituents on an carbocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo. Examples of preferred substituents on an carbocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl, nitro and oxo. Examples of particularly preferred substituents include fluorine, chlorine, bromine, $C_{1-4}$ alkyl, $C_{1-4}$ alkoxy, $C_{1-4}$ haloalkyl and nitro. Further examples of particularly preferred substituents include fluorine, $C_{1-4}$ alkyl, $C_{1-4}$ alkoxy, $C_{1-4}$ haloalkyl and nitro.

As used herein, a heterocyclyl group is a non-aromatic saturated or unsaturated carbocyclic ring typically having from 5 to 10 carbon atoms, in which one or more, for example 1, 2 or 3, of the carbon atoms is replaced by a heteroatom selected from N, O and S. Saturated heterocyclyl groups are preferred. Examples include tetrahydrofuranyl, tetrahydrothienyl, pyrrolidinyl, imidazolidinyl, pyrazolidinyl, dioxolanyl, thiazolidinyl, tetrahydropyranyl, piperidinyl, dioxanyl, piperazinyl, morpholinyl, thiomorpholinyl and thioxanyl. Further examples include dithiolanyl, oxazolidinyl, tetrahydrothiopyranyl and dithianyl. Piperazinyl, piperidinyl and morpholinyl are preferred.

As used herein, references to a heterocyclyl group include fused ring systems in which a heterocyclyl group is fused to a phenyl group. Preferred such fused ring systems are those wherein a 5- to 6-membered heterocyclyl group is fused to a phenyl group. An example of such a fused ring system is a group wherein a 1H-imidazol-2(3H)-onyl group or a imidazolidin-2-onyl group is fused to a phenyl ring to form a 1H-benzo[d]imidazol-2(3R)-onyl group. Most preferably, however, a heterocyclyl group is monocyclic.

A heterocyclic group may be unsubstituted or substituted at any position. Typically, it carries 0, 1 or 2 substituents.

Suitable substituents on a heterocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, oxo, —$CO_2R'$, —CONR'R", —S(O)R', —S(O)$_2$R', —S(O)NR'R", —S(O)$_2$NR'R", —NH—S(O)$_2$R' or —NH—CO—R', wherein each R' and R" is the same or different and represents hydrogen or $C_{1-6}$ alkyl. Examples of suitable substituents on a heterocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, —$CO_2R'$, —CONR'R", —S(O)R', —S(O)$_2$R', —S(O)NR'R", —NH—S(O)$_2$R' or —NH—CO—R', wherein each R' and R" is the same or different and represents hydrogen or $C_{1-6}$ alkyl.

Preferred substituents on a heterocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo. Examples of preferred substituents on a heterocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl, nitro and oxo. Examples of particularly preferred substituents include fluorine, chlorine, bromine, $C_{1-4}$ alkyl, $C_{1-4}$ alkoxy, $C_{1-4}$ haloalkyl and nitro. Further examples of particularly preferred substituents include fluorine, $C_{1-4}$ alkyl, $C_{1-4}$ alkoxy, $C_{1-4}$ haloalkyl and nitro. Most preferably, a heterocyclyl group is unsubstituted or substituted by one or two $C_{1-2}$ alkyl groups.

As used herein, a halogen is typically chlorine, fluorine, bromine or iodine. It is preferably chlorine, fluorine or bromine. It is more preferably chlorine or fluorine.

As used herein, an alkoxy group is typically a said alkyl group attached to an oxygen atom. An alkylthio group is typically a said alkyl group attached to a thio group. A haloalkyl or haloalkoxy group is typically a said alkyl or alkoxy group substituted by one or more said halogen atoms. Typically, it is substituted by 1, 2 or 3 said halogen atoms. Preferred haloalkyl and haloalkoxy groups include perhaloalkyl and perhaloalkoxy groups such as —$CX_3$ and —$OCX_3$ wherein X is a said halogen atom, for example chlorine or fluorine. Particularly preferred haloalkyl groups are —$CF_3$ and —$CCl_3$. Particularly preferred haloalkoxy groups are —$OCF_3$ and —$OCCl_3$.

As used herein, a heteroaryl group is typically a 5- to 10-membered aromatic ring, such as a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, thiazolyl, imidazolyl and pyrazolyl groups.

Further examples include oxazolyl and isothiazolyl. Preferred heteroaryl groups are pyridyl, thienyl, oxazolyl, isoxazolyl, furanyl and pyrazolyl. Examples of preferred heteroaryl groups are pyridyl, thienyl, isoxazolyl and furanyl. As used herein, references to a heteroaryl groups include fused ring systems in which a heteroaryl group is fused to a phenyl group. Preferred such fused ring systems are those wherein a 5- to 6-membered heteroaryl group is fused to a phenyl group. Examples of such fused ring systems are benzofuranyl, benzothiophenyl, indolyl, benzimidazolyl, benzoxazolyl, quinolinyl, quinazolinyl and isoquinolinyl moieties. Most preferably, however, a heterocyclyl group is monocyclic.

A heteroaryl group may be unsubstituted or substituted at any position. Typically, it carries 0, 1, 2 or 3 substituents.

Suitable substituents on a heteroaryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$C_2R'$, —CONR'R", —S(O)R', —S(O)$_2$R', —S(O)NR'R", —S(O)$_2$NR'R", —NH—S(O)$_2$R' or —NH—CO—R', wherein each R' and R" is the same or different and represents hydrogen or $C_{1-6}$ alkyl. Examples of suitable substituents on a heteroaryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl) carbamoyl, amino, mono($C_{1-6}$ alkyl)amino, di($C_{1-6}$ alkyl) amino, —$CO_2R'$, —CONR'R", —S(O)R', —S(O)$_2$R', —S(O)NR'R", —NH—S(O)$_2$R' or —NH—CO—R', wherein each R' and R" is the same or different and represents hydrogen or $C_{1-6}$ alkyl.

Preferred substituents on a heteroaryl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl) amino, nitro and cyano. Particularly preferred substituents include fluorine, chlorine, bromine, $C_{1-4}$ alkyl, $C_{1-4}$ alkoxy, $C_{1-4}$ haloalkyl and nitro. Further preferred substituents include fluorine, chlorine, bromine, $C_{1-2}$ alkyl, $C_{1-2}$ haloalkyl and di($C_{1-2}$ alkyl)amino.

As used herein, references to a heteroaryl group include fused ring systems in which a heteroaryl group is fused to a monocyclic said aryl, carbocyclyl or heterocyclyl group, or to a further heteroaryl group. Preferred such ring systems are those wherein a heteroaryl group is fused to an aryl group, for example a phenyl group. An example of such a fused ring system is a group wherein a thienyl group is fused to a phenyl ring to form a benzothienyl group. A further example of such a fused ring system is a group wherein a furanyl group is fused to a phenyl ring to form a benzofuranyl group.

When $R^1$ is an aryl or heteroaryl group it is typically unsubstituted or substituted by one, two or three substituents selected from halogen, $C_{1-6}$ alkyl, $C_{1-6}$ alkoxy, $C_{1-6}$ alkylthio, $C_{1-6}$ haloalkyl or $C_{1-6}$ haloalkoxy. Preferably, it is unsubstituted or substituted by one or two substituents selected from fluorine, chlorine, bromine, $C_{1-4}$ alkyl, $C_{1-4}$ alkoxy, $C_{1-4}$ alkylthio, $C_{1-4}$ haloalkyl or $C_{1-4}$ haloalkoxy. More preferably, it is unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent.

Typically, $R^1$ is $C_{1-6}$ alkyl or aryl. Preferably, $R^1$ is $C_{1-2}$ alkyl or aryl. More preferably, $R^1$ is $C_{1-2}$ alkyl or phenyl. More preferably, $R^1$ is phenyl.

Typically, $R^2$ is hydrogen or $C_{1-4}$ alkyl. Preferably, $R^2$ is hydrogen.

Typically, $R^3$ is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono ($C_{1-4}$ alkyl)amino or di($C_{1-4}$ alkyl)amino. Preferably, $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono($C_{1-2}$ alkyl)amino or di($C_{1-2}$ alkyl)amino. More preferably, $R^3$ is methyl, trifluoromethyl, fluorine, chlorine or bromine. Most preferably, $R^3$ is methyl or chlorine. An example of a most preferred group is when $R^3$ is chlorine.

Typically, n is 0, 1 or 2. Preferably, n is 0 or 1.

Typically, $R^4$ is hydrogen or $C_{1-4}$ alkyl. Preferably, $R^4$ is hydrogen or $C_{1-2}$ alkyl. More preferably, $R^4$ is hydrogen or methyl. Most preferably, $R^4$ is hydrogen.

When $R^5$ is a heterocyclyl group, it is typically attached via a carbon atom. Typically, $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-C(O)—C(O)—, heterocyclyl-C(O)—C(O)— or —$XR^6$. Examples of typical $R^5$ groups are those wherein $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- or —$XR^6$.

Preferably, $R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-$C_{1-2}$ alkyl)-, phenyl-C(O)—C(O)—, heteroaryl-C(O)—C(O)— or —$XR^6$. Examples of preferred $R^5$ groups are those wherein $R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)- or —$XR^6$.

More preferably, $R^5$ is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$—, furanyl-$CH_2$—, phenyl-C(O)—C(O)—, thienyl-C(O)—C(O)— or —$XR^6$. Examples of more preferred $R^5$ groups are those wherein $R^5$ is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$—, furanyl-$CH_2$— or —$XR^6$.

Most preferably, $R^5$ is phenyl-$CH_2$—, furanyl-$CH_2$—, —C(O)—C(O)— thienyl or —$XR^6$. Examples of most preferred $R^5$ groups are those wherein $R^5$ is phenyl-$CH_2$—, furanyl-$CH_2$— or —$XR^6$.

Typically, X is —CO—, —S(O)— or —S(O)$_2$—. Preferably, X is —CO— or —S(O)$_2$—.

When $R^6$ is a group —NR'R" and either R' or R" includes an aryl, heteroaryl, carbocyclyl or heterocyclyl moiety it is typically unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano. Preferably, the aryl, heteroaryl, carbocyclyl or heterocyclyl moiety is unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro. An example of preferred substitution is when the aryl, heteroaryl, carbocyclyl or heterocyclyl moiety is unsubstituted or substituted by 1 or 2 substituents selected from fluorine, chlorine, bromine, $C_{1-4}$ alkyl, $C_{1-4}$ alkoxy, $C_{1-4}$ haloalkyl and nitro. More preferably, the aryl, heteroaryl, carbocyclyl or heterocyclyl moiety is unsubstituted or substituted by one or two substituents selected from fluorine, chlorine, bromine, $C_{1-2}$ alkyl, $C_{1-2}$ alkoxy, $C_{1-2}$ alkylthio, $C_{1-2}$ haloalkyl and nitro. An example of more preferred substitution is when the aryl, heteroaryl, carbocyclyl or heterocyclyl moiety is unsubstituted or substituted by a single fluoro, chloro, methyl, methoxy or nitro substituent When R' or R" is a heteroaryl or heterocyclyl group, it is attached via a carbon atom.

Typically, R' and R" are not both hydrogen. Typically, each R' and R" is the same or different and represents hydrogen, $C_{1-4}$ alkyl, aryl, heteroaryl, carbocyclyl, aryl-($C_{1-4}$ alkyl)- or heteroaryl-$C_{1-4}$ alkyl)-. Examples of typical R' and R" groups are those wherein each R' and R" is the same or different and represents hydrogen, $C_{1-4}$ alkyl, phenyl, heteroaryl, for example thienyl, carbocyclyl, for example cyclohexyl or cyclopentyl, or phenyl-($C_{1-4}$ alkyl)-. Further examples of typical R' and R" groups are those wherein each R' and R" is the same or different and represents hydrogen, $C_{1-4}$ alkyl, phenyl, thienyl, cyclohexyl, cyclopentyl or phenyl-($CH_2$)—. Preferably, each R' and R" is the same or different and represents hydrogen, $C_{1-4}$ alkyl, phenyl, phenyl-$CH_2$—, cyclohexyl or cyclopentyl. More preferably, one of R' and R" represents hydrogen. Most preferably, one of R' and R" is hydrogen and the other is $C_{1-4}$ alkyl, phenyl, phenyl-$CH_2$—, cyclohexyl or cyclopentyl. As an additional preference, one of R' and R" is hydrogen and the other is $C_{1-4}$ alkyl, phenyl, thienyl or phenyl-$CH_2$—.

Typically, $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-$C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-($C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R" wherein R' and R" are as defined above. Examples of typical $R^6$ groups are those wherein $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- or —NR'R" wherein R' and R" are as defined above.

Preferably, $R^6$ is $C_{1-6}$ alkyl, $C_{1-6}$ alkoxy, $C_{1-6}$ alkylthio, aryl, for example phenyl, naphthyl, dihydrobenzofuranyl, benzodioxinyl, 9H-fluoren-9-onyl and indolyl, heteroaryl, for example thienyl, furanyl, oxazolyl, isoxazolyl, pyrazolyl, pyridyl, benzothienyl and benzofuranyl, carbocyclyl, for example cyclopentyl and cyclohexyl, heterocyclyl, for example piperazinyl, piperidinyl, morpholinyl and 1H-benzo[d]imidazol-2(3H)-onyl, phenyl-($C_{1-2}$ alkyl)-, phenyl-($C_{1-2}$ alkyl)-O—, phenyl-($C_{1-2}$ hydroxyalkyl)-, heteroaryl-($C_{1-2}$ hydroxyalkyl)-, heteroaryl-($C_{1-2}$ alkyl)- or —NR'R" wherein R' and R" are as defined above. Examples of preferred $R^6$ groups are those wherein $R^6$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example N-heterocyclyl, phenyl-($C_{1-2}$ alkyl)-, for example benzyl, heteroaryl-($C_{1-2}$ alkyl)- or —NR'R" wherein R' and R" are as defined above.

More preferably, $R^6$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)—, phenyl-CH(OH)—$CH_2$—, phenyl-($C_{1-2}$ alkyl)-O—, 1H-benzo[d]imidazol-2(3H)-onyl or —NR'R" wherein R' and R" are as defined above. Example of most preferred $R^6$ groups are those wherein $R^6$ is $C_{1-4}$ alkyl, phenyl, thienyl, furanyl, pyridyl, cyclopentyl, cyclohexyl, benzothienyl, dihydrobenzofuranyl, isoxazolyl, piperidinyl, for example N-piperidinyl, morpholinyl, for example N-morpholinyl, piperazinyl, for example N-piperazinyl, or —NR'R" wherein R' and R" are as, defined above.

Preferred compounds of the invention are those in which:

$R^1$ is $C_{1-6}$ alkyl or aryl;

$R^2$ is hydrogen or $C_{1-4}$ alkyl;

$R^3$ is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino or di($C_{1-4}$ alkyl)amino or, preferably, $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono ($C_{1-2}$ alkyl)amino or di ($C_{1-2}$ alkyl)amino;

n is 0, 1 or 2;

$R^4$ is hydrogen or $C_{1-4}$ alkyl;

$R^5$ is $C_{1-6}$ alkyl, aryl, heteroaryl; carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-C(O)—C(O)—, heteroaryl-C(O)—C(O)— or $XR^6$;

X is —CO—, —S(O)— or —S(O)$_2$—; and $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-($C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-$C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R", wherein each R' and R" is the same or different and represents hydrogen, $C_{1-4}$ alkyl, aryl, heteroaryl, carbocyclyl, aryl-($C_{1-4}$ alkyl)- or heteroaryl-($C_{1-4}$ alkyl)-, the aryl moiety in the $R^1$ group being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl or $C_{1-6}$ haloalkoxy;

the aryl and heteroaryl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—$R'$, wherein each $R'$ and $R''$ is the same or different and represents hydrogen or $C_{1-6}$ alkyl;

the carbocyclyl and heterocyclyl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, oxo, —$CO_2R''$, —$CONR'R''$, —$S(O)R'$, —$S(O)_2R'$, —$S(O)NR'R''$, —$S(O)_2NR'R''$, —NH—$S(O)_2R'$ or —NH—CO—$R'$, wherein each $R'$ and $R''$ is the same or different and represents hydrogen or $C_{1-6}$ alkyl; and the alkyl moieties in the aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- groups of $R^6$ being unsubstituted or substituted by one or two hydroxy substituents.

Preferably, in these preferred compounds of the invention, the aryl, heteroaryl and carbocyclyl moieties in the groups $R'$ and $R''$ are unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano.

Examples of preferred compounds of the invention are those wherein $R^1$, $R^2$, $R^3$, $R^4$ and n are as defined for the preferred compounds of the invention, $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-$C_{1-4}$ alkyl)-, heterocyclyl-($C_{1-4}$ alkyl)- or —$XR^6$;

X is —CO—, —S(O)— or —$S(O)_2$—; and $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-$C_{1-4}$ alkyl)-, heterocyclyl-($C_{1-4}$ alkyl)- or —$NR'R''$, wherein each $R'$ and $R''$ is the same or different and represents hydrogen, $C_{1-4}$ alkyl, aryl, heteroaryl, carbocyclyl, aryl-($C_{1-4}$ alkyl)- or heteroaryl-($C_{1-4}$ alkyl)-, the aryl, heteroaryl, carbocyclyl and heterocyclyl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano.

Further preferred compounds of the invention are those wherein:

$R^1$ is $C_{1-2}$ alkyl or phenyl;

$R^2$ is hydrogen or $C_{1-4}$ alkyl;

$R^3$ is methyl, trifluoromethyl, fluorine, chlorine or bromine;

n is 0 or 1;

$R^4$ is hydrogen or $C_{1-2}$ alkyl;

$R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)-, phenyl-C(O)—C(O)—, heteroaryl-C(O)—C(O)— or —$XR^6$, provided that when $R^5$ is heterocyclyl it is attached via a carbon atom;

X is —CO—, —S(O)— or —$S(O)_2$—; and $R^6$ is $C_{1-6}$ alkyl, $C_{1-6}$ alkoxy, $C_{1-6}$ alkylthio, aryl, for example phenyl, naphthyl, dihydrobenzofuranyl, benzodioxinyl, 9H-fluoren-9-onyl and indolyl, heteroaryl, for example thienyl, furanyl, oxazolyl, isoxazolyl, pyrazolyl, pyridyl, benzothienyl and benzofuranyl, carbocyclyl, for example cyclopentyl and cyclohexyl, heterocyclyl, for example piperazinyl, piperidinyl, morpholinyl and 1H-benzo[d]imidazol-2(3R)-onyl, phenyl-($C_{1-2}$ alkyl)-, phenyl-($C_{1-2}$ alkyl)-O—, phenyl-($C_{1-2}$ hydroxyalkyl)-, heteroaryl-($C_{1-2}$ hydroxyalkyl)-, heteroaryl-($C_{1-2}$ alkyl)- or —$NR'R''$ wherein each $R'$ and $R''$ is the same or different and represents hydrogen, $C_{1-4}$ alkyl, phenyl, heteroaryl, for example thienyl, carbocyclyl, for example cyclohexyl or cyclopentyl, or phenyl-$C_{1-4}$ alkyl)-, the phenyl moiety in the $R^1$ group being unsubstituted or substituted bygone or two substituents selected from fluorine, chlorine, bromine, $C_{1-4}$ alkyl, $C_{1-4}$ alkoxy, $C_{1-4}$ alkylthio, $C_{1-4}$ haloalkyl or $C_{1-4}$ haloalkoxy;

the aryl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —$S(O)R'$, —$S(O)_2R''$ and —$S(O)_2NR'R''$, wherein each $R'$ and $R''$ is the same or different and represents hydrogen or $C_{1-4}$ alkyl;

the heteroaryl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano; and the carbocyclyl and heterocyclyl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo; and the alkyl moiety in the phenyl-($C_{1-2}$ alkyl)- and heteroaryl-($C_{1-2}$ alkyl)- groups of $R^6$ being unsubstituted or substituted by a single hydroxy substituent Preferably, in these further preferred compounds of the invention, the phenyl, heteroaryl and carbocyclyl moieties in the groups $R'$ and $R''$ are unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro.

Examples of further preferred compounds of the invention are those wherein $R^1$, $R^2$, $R^3$, $R^4$ and n are as defined for the further preferred compounds of the invention, $R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)- or —$XR^6$, provided that when $R^5$ is heterocyclyl it is attached via a carbon atom;

—X is —CO—, —S(O)— or —$S(O)_2$—; and $R^6$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example N-heterocyclyl, phenyl-($C_{1-2}$ alkyl)-, for example benzyl, heteroaryl-($C_{1-2}$ alkyl)- or —NR'R", wherein each R' and R" is the same or different and represents hydrogen, $C_{1-4}$ alkyl, cyclohexyl, cyclopentyl, phenyl or phenyl-$CH_2$—, the aryl, heteroaryl, carbocyclyl and heterocyclyl moieties in the groups $R^5$ and $R^6$ being unsubstituted or substituted by 1 or 2 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl) amino, nitro and cyano.

As a further preference, in these further preferred compounds of the invention, the cyclohexyl, cyclopentyl and phenyl moieties in the groups R' and R" are unsubstituted or substituted by 1 or 2 substituents selected from fluorine, chlorine, bromine, $C_{1-4}$ alkyl, $C_{1-4}$ alkoxy, $C_{1-4}$ haloalkyl and nitro.

Particularly preferred compounds of the invention are compounds of formula (Ia) are pharmaceutically acceptable salts thereof

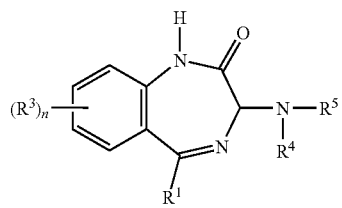

(Ia)

wherein:
$R^1$ is phenyl or methyl;
$R^3$ is methyl or chlorine;
n is 0 or 1;
$R^4$ is hydrogen or methyl;
$R^5$ is phenyl-$CH_2$—, furanyl-$CH_2$—, thienyl-C(O)—C(O)— or —$XR^6$;
X is —CO— or —S(O)$_2$—; and
$R^6$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)—, phenyl-CH(OH)—$CH_2$—, phenyl-$C_{1-2}$ alkyl)-O—, 1H-benzo[d]imidazol-2(3H)-onyl or —NR'R" wherein each R' and R" is the same or different and represents hydrogen, $C_{1-4}$ alkyl, phenyl, thienyl, cyclohexyl, cyclopentyl or phenyl-($CH_2$)—, the phenyl moiety in the group $R^1$ being unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent;

the aryl moieties in the groups $R^5$ and $R^6$ being unsubstituted or substituted by 1, 2 or 3 substituents selected from fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl) amino, di($C_{1-4}$ alkyl)amino, nitro, —$CO_2R'$, —S(O)$_2R'$ and —S(O)$_2NH_2$, wherein R' represents $C_{1-2}$ alkyl;

the heteroaryl moieties in the groups $R^5$ and $R^6$ being unsubstituted or substituted by 1 or 2 substituents selected from fluorine, chlorine, bromine, $C_{1-2}$ alkyl, $C_{1-2}$ haloalkyl and di($C_{1-2}$ alkyl)amino; and the heterocyclyl and carbocyclyl moieties in the $R^6$ group being unsubstituted or substituted by 1 or 2 substituents selected from fluorine, chlorine, bromine, $C_{1-4}$ alkyl, $C_{1-4}$ alkoxy, $C_{1-4}$ haloalkyl and nitro.

Examples of particularly preferred compounds of formula (Ia) are compounds of formula (Ia') pharmaceutically acceptable salts thereof

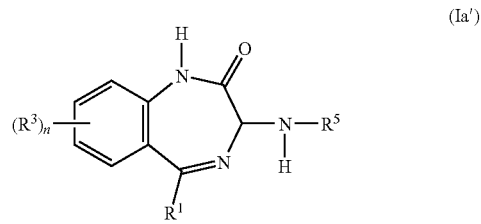

(Ia')

wherein:
$R^1$ is phenyl or methyl;
$R^3$ is chlorine;
n is 0 or 1;
$R^5$ is phenyl-$CH_2$—, furanyl-$CH_2$— or —$XR^6$;
X is —CO— or —S(O)$_2$—; and
$R^6$ is $C_{1-4}$ alkyl, phenyl, thienyl, furanyl, pyridyl, cyclopentyl, cyclohexyl, benzothienyl, dihydrobenzofuranyl, isoxazolyl, piperidinyl, for example N-piperidinyl, morpholinyl, for example N-morpholinyl, piperazinyl, for example N-piperazinyl, or —NR'R", wherein each R' and R" is the same or different and represents hydrogen, $C_{1-4}$ alkyl, cyclohexyl, cyclopentyl, phenyl or phenyl-$CH_2$—, the phenyl, thienyl, furanyl, pyridyl, cyclopentyl, cyclohexyl, benzothienyl, dihydrobenzofuranyl, isoxazolyl, piperidinyl, morpholinyl and piperazinyl moieties in the groups $R^5$ and $R^6$ being unsubstituted or substituted by 1 or 2 substituents selected from fluorine, chlorine, bromine, $C_{1-4}$ alkyl, $C_{1-4}$ alkoxy, $C_{1-4}$ haloalkyl and nitro.

Preferably, in these particularly preferred compounds of the invention, the cyclohexyl, cyclopentyl and phenyl moieties of the groups R' and R" are unsubstituted or substituted by a single fluoro, chloro, methyl, methoxy or nitro substituent.

Compounds of the formula (I) containing one or more chiral centre may be used in enantiomerically or diastereoisomerically pure form, or in the form of a mixture of isomers. For the avoidance of doubt, the chemical structures depicted herein are intended to embrace all stereoisomers of the compounds shown, including racemic and non-racemic mixtures and pure enantiomers and/or diastereoisomers.

Preferred compounds of the invention are optically active isomers. Thus, for example, preferred compounds of formula (I) containing only one chiral centre include an R enantiomer in substantially pure form, an S enantiomer in substantially pure form and enantiomeric mixtures which contain an excess of the R enantiomer or an excess of the S enantiomer. For the avoidance of doubt, the compounds of the formula (I) can, if desired, be used in the form of solvates.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutical acceptable bases include alkali metal (e.g. sodium or potassium) and alkaline earth metal (e.g. calcium or magnesium) hydroxides and organic bases such as alkyl amines, aralkyl amines or heterocyclic amines.

Particularly preferred compounds of the invention include:
N-(2-Oxo-5-phenyl-2,3-dihydro-1H-benzo[e][1,4]diazepin-3-yl)-acetamide;
1,1-Diethyl-3-(2-oxo-5-phenyl-2,3-dihydro-1H-benzo[e][1,4]diazepin-3-yl)-urea;
N-(2-Oxo-5-phenyl-2,3-dihydro-1H-benzo[e][1,4]diazepin-3-yl)-propionamide;
N-(2-Oxo-5-phenyl-2,3-dihydro-1H-benzo[e][1,4]diazepin-3-yl)-butyramide;
N-(2-Oxo-5-phenyl-2,3-dihydro-1H-benzo[e][1,4]diazepin-3-yl)-isobutyramide;
2,2-Dimethyl-N-(2-Oxo-5-phenyl-2,3-dihydro-1H-benzo[e][1,4]diazepin-3-yl)-propionamide;
Cyclopentanecarboxylic acid (2-oxo-5-phenyl-2,3-dihydro-1H-benzo[e][1,4]diazepin-3-yl)-amide;
Cyclohexanecarboxylic acid 2-oxo-5-phenyl-2,3-dihydro-1H-benzo[e][1,4]diazepin-3-yl)-amide;
3-Methoxy N-(2-oxo-5-phenyl-2,3-dihydro-1H-benzo[e][1,4]diazepin-3-yl)-benzamide;
4-Methoxy N-(2-oxo-5-phenyl-2,3-dihydro-1H-benzo[e][1,4]diazepin-3-yl)-benzamide;
2-Methoxy N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)-3-trifluoromethyl-benzamide;
N-(2-Oxo-5-phenyl-2,3-dihydro-1H-benzo[e][1,4]diazepin-3-yl)-benzamide;
Thiophene-2-carboxylic acid (2-oxo-5-phenyl-2,3-dihydro-1H-benzo[e][1,4]diazepin-3-yl)-3-amide;
Furan-2-carboxylic acid (2-oxo-5-phenyl-2,3-dihydro-1H-benzo[e][1,4]diazepin-3-yl)-amide;
Piperidine-1-carboxylic acid (2-oxo-5-phenyl-2,3-dihydro-1H-benzo[e][1,4]diazepin-3-yl)-amide;
Morpholine-4-carboxylic acid (2-oxo-5-phenyl-2,3-dihydro-1H-benzo[e][1,4]diazepin-3-yl)-amide;
4-Nitro-N-(2-oxo-5-phenyl-2,3-dihydro-1H-benzo[e][1,4]diazepin-3-yl)-benzamide;
3-Nitro-N-(2-oxo-5-phenyl-2,3-dihydro-1H-benzo[e][1,4]diazepin-3-yl)-benzamide;
4-Methyl-piperazine-1-carboxylic acid -(2-oxo-5-phenyl-2,3-dihydro-1H-benzo[e][1,4]diazepin-3-yl)-amide;
3,4-Dichloro-N-(2-oxo-5-phenyl-2,3-dihydro-1H-benzo[e][1,4]diazepin-3-yl)-benzamide;
N-(2-oxo-5-phenyl-2,3-dihydro-1H-benzo[e][1,4]diazepin-3-yl)-2-trifluoromethyl-benzamide;
4-Bromo-N-(2-oxo-5-phenyl-2,3-dihydro-1H-benzo[e][1,4]diazepin-3-yl)-benzamide;
2-Methyl-N-(2-oxo-5-phenyl-2,3-dihydro-1H-benzo[e][1,4]diazepin-3-yl)-benzamide;
2-Chloro-N-(2-oxo-5-phenyl-2,3-dihydro-1H-benzo[e][1,4]diazepin-3-yl)-benzamide;
2-Nitro-N-(2-oxo-5-phenyl-2,3-dihydro-1H-benzo[e][1,4]diazepin-3-yl)-benzamide;
2-Methoxy-4-nitro-N-(2-oxo-5-phenyl-2,3-dihydro-1H-benzo[e][1,4]diazepin-3-yl)-benzamide;
(S)-2-Methoxy-4-nitro-N-(2-oxo-5-phenyl-2,3-dihydro-1H-benzo[e][1,4]diazepin-3-yl)-benzamide
Benzo[b]thiophene-3-carboxylic acid (2-oxo-5-phenyl-2,3-dihydro-1H-benzo[e][1,4]diazepin-3-yl)-amide;
2,3-Dihydro-benzofuran-5-carboxylic acid (2-oxo-5-phenyl-2,3dihydro-1H-benzo[e][1,4]diazepin-3-yl)-amide;
Isoxazole-5-carboxylic acid (2-oxo-5-phenyl-2,3-dihydro-1H-benzo[e][1,4]diazepin-3-yl)-amide;
Benzo[b]thiophene-2-carboxylic acid (2-oxo-5-phenyl-2,3-dihydro-1H-benzo[e][1,4]diazepin-3-yl)-amide;
Thiophen-3-carboxylic acid (2-oxo-5-phenyl-2,3-dihydro-1H-benzo[e][1,4]diazepin-3-yl)-amide;
N-(2-Oxo-5-phenyl-2,3-dihydro-1H-benzo[e][1,4]diazepin-3-yl)-isonicotinamide;
N-(2-Oxo-5-phenyl-2,3-dihydro-1H-benzo[e][1,4]diazepin-3-yl)-nicotinamide;
N-(2-Oxo-5-phenyl-2,3-dihydro-1H-benzo[e][1,4]diazepin-3-yl)-methanesulfonamide;
Propane-1-sulfonic acid-(2-oxo-5-phenyl-2,3-dihydro-1H-benzo[e][1,4]diazepin-3-yl)-amide;
Butane-1-sulfonic acid-(2-oxo-5-phenyl-2,3-dihydro-1H-benzo[e][1,4]diazepin-3-yl)-amide;
2-Bromo-N-(2-oxo-5-phenyl-2,3-dihydro-1H-benzo[e][1,4]diazepin-3-yl)-benzenesulfonamide;
3-Bromo-N-(2-oxo-5-phenyl-2,3-dihydro-1H-benzo[e][1,4]diazepin-3-yl)-benzenesulfonamide;
4-Bromo-N-2-oxo-5-phenyl-2,3-dihydro-1H-benzo[e][1,4]diazepin-3-yl)-benzenesulfonamide;
2-Fluoro-N-(2-oxo-5-phenyl-2,3-dihydro-1H-benzo[e][1,4]diazepin-3-yl)-benzenesulfonamide;
3-(2-Nitro-benzylamino)-5-phenyl-1,3-dihydro-benzo[e][1,4]diazepin-2-one;
3-(3-Nitro-benzylamino)-5-phenyl-1,3-dihydro-benzo[e][1,4]diazepin-2-one;
3-(4-Nitro-benzylamino)-5-phenyl-1,3-dihydro-benzo[e][1,4]diazepin-2-one;
3-(2-Methoxy-benzylamino)-5-phenyl-1,3-dihydro-benzo[e][1,4]diazepin-2-one;
3-(3-Methoxy-benzylamino)-5-phenyl-1,3-dihydro-benzo[e][1,4]diazepin-2-one;
5-Phenyl-3-2-trifluoromethyl-benzylamino)-1,3-dihydro-benzo[e][1,4]diazepin-2-one;
5-Phenyl-3-(3-trifluoromethyl-benzylamino)-1,3-dihydro-benzo[e][1,4]diazepin-2-one;
5-Phenyl-3-(4-trifluoromethyl-benzylamino)-1,3-dihydro-benzo[e][1,4]diazepin-2-one;
3-[(Furan-2-ylmethyl)-amino]-5-phenyl-1,3-dihydro-benzo[e][1,4]diazepin-2-one;
N-(7-Chloro-2-oxo-5-phenyl-2,3-dihydro-1H-benzo[e][1,4]diazepin-3-yl)-acetamide;
N-(7-Chloro-2-oxo-5-phenyl-2,3-dihydro-1H-benzo[e][1,4]diazepin-3-yl)-isobutyramide;
N-(7-Chloro-2-oxo-5-phenyl-2,3-dihydro-1H-benzo[e][1,4]diazepin-3-yl)-methanesulfonamide;
Furan-2-carboxylic acid (7-chloro-2-oxo-5-phenyl-2,3-dihydro-1H-benzo[e][1,4]diazepin-3-yl)-amide;
Thiophene-2-carboxylic acid (7-chloro-2-Oxo-5-phenyl-2,3-dihydro-1H-benzo[e][1,4]diazepin-3-yl)-amide;
Cyclohexanecarboxylic acid (7-Chloro-2-oxo-5-phenyl-2,3-dihydro-1H-benzo[e][1,4]diazepin-3-yl)-amide;
N-(7-Chloro-2-oxo-5-phenyl-2,3-dihydro-1H-benzo[e][1,4]diazepin-3-yl)-2-methoxy-benzamide;
N-(7-Chloro-2-oxo-5-phenyl-2,3-dihydro-1H-benzo[e][1,4]diazepin-3-yl)-4-methoxy-benzamide;
N-7-Chloro-2-oxo-5-phenyl-2,3-dihydro-1H-benzo[e][1,4]diazepin-3-yl)-2-nitro-benzamide;
2-(2-Methoxy-phenyl)N-(2-oxo-5-phenyl-2,3-dihydro-1H-benzo[e][1,4]diazepin-3-yl)-acetamide;
2-(3-Methoxy-phenyl)N-(2-oxo-5-phenyl-2,3-dihydro-1H-benzo[e][1,4]diazepin-3-yl)-acetamide;
2-(4-Methoxy-phenyl)N-(2-oxo-5-phenyl-2,3-dihydro-1H-benzo[e][1,4]diazepin-3-yl)-acetamide;
2-(4Nitro-phenyl)N-(2-oxo-5-phenyl-2,3-dihydro-1H-benzo[e][1,4]diazepin-3-yl)-acetamide;

2-(3-nitro-phenyl)N-(2-oxo-5-phenyl-2,3-dihydro-1H-benzo[e][1,4]diazepin-3-yl)-acetamide;
N-(2-Oxo-5-phenyl-2,3-dihydro-1H-benzo[e][1,4]diazepin-3-yl)-2-(2-trifluoromethyl-phenyl)-acetamide;
N-(2-Oxo-5-phenyl-2,3-dihydro-1H-benzo[e][1,4]diazepin-3-yl)-2-(3-trifluoromethyl-phenyl)-acetamide;
N-(2-Oxo-5-phenyl-2,3-dihydro-1H-benzo[e][1,4]diazepin-3-yl)-2-(4-trifluoromethyl-phenyl)-acetamide;
1-(2-Methoxy-phenyl)-3-(2-oxo-5-phenyl-2,3-dihydro-1H-benzo[e][1,4]diazepin-3-yl)-urea;
1-(2-Nitro-phenyl)-3-(2-oxo-5-phenyl-2,3dihydro-1H-benzo[e][1,4]diazepin-3-yl)-urea;
1-(2-Chloro-phenyl)-3-(2-oxo-5-phenyl-2,3-dihydro-1H-benzo[e][1,4]diazepin-3-yl)-urea;
1-(4-Chloro-phenyl)-3-(2-oxo-5-phenyl-2,3-dihydro-1H-benzo[e][1,4]diazepin-3-yl)-urea;
1-(2-oxo-5-phenyl-2,3-dihydro-1H-benzo[e][1,4]diazepin-3-yl)-3-p-tolyl-urea;
1-(2-Fluoro-phenyl)-3-(2-oxo-5-phenyl-2,3-dihydro-1H-benzo[e][1,4]diazepin-3-yl)-urea;
1-(4-Fluoro-phenyl)-3-(2-oxo-5-phenyl-2,3-dihydro-1H-benzo[e][1,4]diazepin-3-yl)-urea;
(S)-1-(2-Fluoro-phenyl)-3-2-oxo-5-phenyl-2,3dihydro-1H-benzo[e][1,4]diazepin-3-yl)-urea;
4-Methanesulfonyl-2-methoxy-N-(oxo-5-phenyl-2,3-dihydro-1H-benzo[e][1,4]diazepin-3-yl)-benzamide;
(S)-4-Methanesulfonyl-2-methoxy-N-(2-oxo-5-phenyl-2,3dihydro-1H-benzo[e][1,4]diazepin-3-yl)-benzamide;
5-Acetyl-2-ethoxy-N-(2-oxo-5-phenyl-2,3-dihydro-1H-benzo[e][1,4]diazepin-3-yl)-benzamide;
(S)-5-Acetyl-2-ethoxy-N-(2-oxo-5-phenyl-2,3-dihydro-1H-benzo[e][1,4]diazepin-3-yl)-benzamide;
6-Fluoro-4H-benzo[1,3]dioxine-8-carboxylic acid (2-oxo-5-phenyl-2,3-dihydro-1H-benzo[e][1,4]diazepin-3-yl)-amide;
(S)-6-Fluoro-4H-benzo[1,3]dioxine-8-carboxylic acid (2-oxo-5-phenyl-2,3-dihydro-1H-benzo[e][1,4]diazepin-3-yl)-amide;
(S)-2-Methoxy-N-(2-oxo-5-phenyl-2,3-dihydro-1H-benzo[e][1,4]diazepin-3-yl)-4-trifluoromethyl-benzamide;
2,4,5-Trifluoro-N-(2-oxo-5-phenyl-2,3-dihydro-1H-benzo[e][1,4]diazepin-3-yl)-benzamide;
(S)-2,4,5-Trifluoro-N-2-oxo-5-phenyl-2,3-dihydro-1H-benzo[e][1,4]diazepin-3-yl)-benzamide;
2-Hydroxy-N-(2-oxo-5-phenyl-2,3-dihydro-1H-benzo[e][1,4]diazepin-3-yl)-benzamide;
(S)-2-Hydroxy-N-(2-oxo-5-phenyl-2,3-dihydro-1H-benzo[e][1,4]diazepin-3-yl)-benzamide;
1H-Indole-7-carboxylic acid (2-oxo-5-phenyl-2,3-dihydro-1H-benzo[e][1,4]diazepin-3-yl)-amide;
(S)-1H-Indole-7-carboxylic acid (2-oxo-5-phenyl-2,3-dihydro-1H-benzo[e][1,4]diazepin-3-yl)-amide;
3-Methoxy-naphthalene-2-carboxylic acid (2-oxo-5-phenyl-2,3-dihydro-1H-benzo[e][1,4]diazepin-3-yl)-amide;
(S)-3-Methoxy-naphthalene-2-carboxylic acid (2-oxo-5-phenyl-2,3-dihydro-1H-benzo[e][1,4]diazepin-3-yl)-amide;
N-[7-Chloro-5-(2-fluoro-phenyl)-2-oxo-2,3-dihydro-1H-benzo[e][1,4]diazepine-3-yl]-4-methoxy-benzamide;
1-(2-Fluoro-benzyl)-3-(2-oxo-5-phenyl-2,3-dihydro-1H-benzo[e][1,4]diazepin-3-yl)-urea;
1-(4-Methoxy-benzyl)-3-(2-oxo-5-phenyl-2,3-dihydro-1H-benzo[e][1,4]diazepin-3-yl)-urea;
1-(3-Methyl-benzyl)-3-(2-oxo-5-phenyl-2,3-dihydro-1H-benzo[e][1,4]diazepin-3-yl)-urea;
1-(2-Oxo-5-phenyl-2,3dihydro-1H-benzo[e][1,4]diazepin-3-yl)-3-(4-trifluoromethyl-phenyl)-urea;
4-Chloro-2-methoxy-N-(2-oxo-5-phenyl-2,3-dihydro-1H-benzo[e][1,4]diazepin-3-yl)-benzamide;
4-Methoxy-3-nitro-N-2-oxo-5-phenyl-2,3-dihydro-1H-benzo[e][1,4]diazepin-3-yl)benzamide;
3-Methoxy-2-nitro-N-2-oxo-5-phenyl-2,3-dihydro-1H-benzo[e][1,4]diazepin-3-yl)-benzamide;
5-Chloro-2-methoxy-N-(2-oxo-5-phenyl-2,3-dihydro-1H-benzo[e][1,4]diazepin-3-yl)benzamide;
5-Fluoro-2-methoxy-N-(2-oxo-5-phenyl-2,3-dihydro-1H-benzo[e][1,4]diazepin-3-yl)-benzamide;
2-Methoxy-4-nitro-N-(2-oxo-5-phenyl-2,3-dihydro-1H-benzo[e][1,4]diazepin-3-yl)-benzamide;
5-Methoxy-2-nitro-N-2-oxo-5-phenyl-2,3-dihydro-1H-benzo[e][1,4]diazepin-3-yl)-benzamide;
3-Methoxy-4-nitro-N-(2-oxo-5-phenyl-2,3-dihydro-1H-benzo[e][1,4]diazepin-3-yl)-benzamide;
3-(2-Methoxy-phenyl)-N-(2-oxo-5-phenyl-2,3-dihydro-1H-benzo[e][1,4]diazepin-3-yl)propionamide;
3-(3-Methoxy-phenyl)-N-(2-oxo-5-phenyl-2,3-dihydro-1H-benzo[e][1,4]diazepin-3-yl)-propionamide;
3-(4-Methoxy-phenyl)-N-(2-oxo-5-phenyl-2,3-dihydro-1H-benzo[e][1,4]diazepin-3-yl)-propionamide;
N-[5-(3-Chloro-phenyl)-2-oxo-2,3-dihydro-1H-benzo[e][1,4]diazepin-3-yl]-2-methoxy-benzamide;
N-[5-(3-Chloro-phenyl)-2-oxo-5-phenyl-2,3-dihydro-1H-benzo[e][1,4]diazepin-3-yl]4-methoxy-benzamide;
N-[5-(3-Chloro-phenyl)-2-oxo-5-phenyl-2,3-dihydro-1H-benzo[e][1,4]diazepin-3-yl]-2-nitro-benzamide;
N-[5-(3-Chloro-phenyl)-2-oxo-5-phenyl-2,3-dihydro-1H-benzo[e][1,4]diazepin-3-yl]-4-nitro-benzamide;
4-Methoxy-N-[2-oxo-5-(4-trifluoromethyl-phenyl)-2,3-dihydro-1H-benzo[e][1,4]diazepin-3-yl]-benzamide;
2-Methoxy-N-[2-oxo-5-(3-trifluoromethyl-phenyl)-2,3-dihydro-1H-benzo[e][1,4]diazepin-3-yl]-benzamide;
4-Methoxy-N-[2-oxo-5-(3-trifluoromethyl-phenyl)-2,3-dihydro-1H-benzo[e][1,4]diazepin-3-yl]-benzamide;
2-Ethoxy-N-(2-oxo-5-phenyl-2,3-dihydro-1H-benzo[e][1,4]diazepin-3-yl)-benzamide;
2,4-Dimethoxy-N-2-oxo-5-phenyl-2,3-dihydro-1H-benzo[e][1,4]diazepin-3-yl)-benzamide;
2-Bromo-5-methoxy-N-(2-oxo-5-phenyl-2,3-dihydro-1H-benzo[e][1,4]diazepin-3-yl)benzamide;
2-Methoxy-N-[5-(3-methoxy-phenyl)-2-oxo-2,3dihydro-1H-benzo[e][1,4]diazepin-3-yl]-benzamide
N-[5-(3-Methoxy-phenyl)-2-oxo-5-phenyl-2,3dihydro-1H-benzo[e][1,4]diazepin-3-yl]-4-nitro-benzamide;
2-Methoxy-N-(8-methyl-2-oxo-5-phenyl-2,3-dihydro-1H-benzo[e][1,4]diazepin-3-yl)-benzamide;
2-Chloro-4-methanesulfonyl-N-(2-oxo-5-phenyl-2,3-dihydro-1H-benzo[e][1,4]diazepin-3-yl)-benzamide;
2-Dimethylamino-N-(2-oxo-5-phenyl-2,3-dihydro-1H-benzo[e][1,4]diazepin-3-yl)-benzamide;
(2-Oxo-5-phenyl-2,3-dihydro-1H-benzo[e][1,4]diazepin-3-yl)-carbamic acid benzyl ester;
1-(3,5-Dimethyl-phenyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(4-trifluoromethoxy-phenyl)-urea;
1-(4-Bromo-2-trifluoromethyl-phenyl)-3-(2-oxo-5-phenyl-2,3-dihydro-1H-benzo[e][1,4]diazepin-3-yl)-urea;
1-(4-Bromo-benzyl)-3-(2-oxo-5-phenyl-2,3-dihydro-1H-benzo[e][1,4]diazepin-3-yl)-urea;
1-(2,3-Dichloro-phenyl)-3-2-oxo-5-phenyl-2,3-dihydro-1H-benzo[e][1,4]diazepin-3-yl)-urea;
1-(2,6-Dimethyl-phenyl)-3-(2-oxo-5-phenyl-2,3-dihydro-1H-benzo[e][1,4]diazepin-3-yl)-urea;

1-(2-Chloro-6-methyl-phenyl)-3-(2-oxo-5-phenyl-2,3-dihydro-1H-benzo[e][1,4]diazepin-3-yl)-urea;
1-(4-Nitro-phenyl)-3-(2-oxo-5-phenyl-2,3-dihydro-1H-benzo[e][1,4]diazepin-3-yl)-urea;
1-(2-Methylsulfanyl-phenyl)-3-(2-oxo-5-phenyl-2,3-dihydro-1H-benzo[e][1,4]diazepin-3-yl)-urea;
1-(2,6-Dichloro-phenyl)-3-(2oxo-5-phenyl-2,3dihydro-1H-benzo[e][1,4]diazepin-3-yl)-urea;
5-tert-Butyl-2-methoxy-N-(2-oxo-5-phenyl-2,3-dihydro-1H-benzo[e][1,4]diazepin-3-yl)-benzamide;
2,5-Dimethoxy-N-(2-oxo-5-phenyl-2,3-dihydro-1H-benzo[e][1,4]diazepin-3-yl)-benzamide;
1-(2,6-Difluoro-phenyl)-3-(2-oxo-5-phenyl-2,3-dihydro-1H-benzo[e][1,4]diazepin-3-yl)-urea;
1-(3-Fluoro-phenyl)-3-(2-oxo-5-phenyl-2,3-dihydro-1H-benzo[e][1,4]diazepin-3-yl)-urea;
1-(3-Methoxy-phenyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(3-trifluoromethyl-phenyl)-urea;
1-(3-Chloro-phenyl)-3-(2-oxo-5-phenyl-2,3-dihydro-1H-benzo[e][1,4]diazepin-3-yl)-urea;
2-Methoxy-4-methylsulfanyl-N-(2-oxo-5-phenyl-2,3-dihydro-1H-benzo[e][1,4]diazepin-3-yl)-benzamide;
4-Methanesulfonyl-N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)terephthalamic acid methyl ester;
2-Fluoro-N-(2-oxo-5-phenyl-2,3-dihydro-1H-benzo[e][1,4]diazepin-3-yl)-benzamide;
2,6-Difluoro-N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)-2-propoxy-benzamide;
2-Iodo-N-(2-oxo-5-phenyl-2,3-dihydro-1H-benzo[e][1,4]diazepin-3-yl)-benzamide;
3-Methoxy-N-(2-oxo-5-phenyl-2,3-dihydro-1H-benzo[e][1,4]diazepin-3-yl)-terephthalamic acid methyl ester;
4-Amino-5-chloro-2-methoxy-N-(2-oxo-5-phenyl-2,3dihydro-1H-benzo[e][1,4]diazepin-3-yl)-benzamide;
1-(2-Oxo-5-phenyl-2,3-dihydro-1H-benzo[e][1,4]diazepin-3-yl)-3-m-tolyl-urea;
2-Methylsulfanyl-N-(2-oxo-5-phenyl-2,3-dihydro-1H-benzo[e][1,4]diazepin-3-yl)-benzamide;
2-Methoxy-N-(2-oxo-5-phenyl-2,3-dihydro-1H-benzo[e][1,4]diazepin-3-yl)-5-sulfamoyl-benzamide;
2-Hydroxy-N-(2-oxo-5-phenyl-2,3-dihydro-1H-benzo[e][1,4]diazepin-3-yl)-3-phenyl-propionamide
3-Hydroxy-N-(2-oxo-5-phenyl-2,3-dihydro-1H-benzo[e][1,4]diazepin-3-yl)-3-phenyl-propionamide
3-(2-Fluoro-phenyl)-1-methyl-1-(2-oxo-5-phenyl-2,3-dihydro-1H-benzo[e][1,4]diazepin-3-yl)-urea;
2-Methoxy-N-methyl-4-nitro-N-(2-oxo-5-phenyl-2,3-dihydro-1H-benzo[e][1,4]diazepin-3-yl)-benzamide;
1-tert-Butyl-3-(2-oxo-5-phenyl-2,3-dihydro-1H-benzo[e][1,4]diazepin-3-yl)-urea;
1-Cyclohexyl-3-(2-oxo-5-phenyl-2,3-dihydro-1H-benzo[e][1,4]diazepin-3-yl)-urea;
1-Ethyl-3-(2-oxo-5-phenyl-2,3-dihydro-1H-benzo[e][1,4]diazepin-3-yl)-urea;
1-Butyl-3-(2-oxo-5-phenyl-2,3-dihydro-1H-benzo[e][1,4]diazepin-3-yl)-urea;
4,5-Dimethyl-furan-2-carboxylic acid (2-oxo-5-phenyl-2,3-dihydro-1H-benzo[e][1,4]diazepin-3-yl)amide;
Piperidine-1-carboxylic acid (7-chloro-2-oxo-5-phenyl-2,3-dihydro-1H-benzo[e][1,4]diazepin-3-yl)-amide;
N-[5-(3-Chloro-phenyl)-2-oxo-5-phenyl-2,3-dihydro-1H-benzo[e][1,4]diazepin-3-yl]-acetamide;
N-[5-(3-Chloro-phenyl)-2-oxo-5-phenyl-2,3-dihydro-1H-benzo[e][1,4]diazepin-3-yl]-isobutyramide;
Furan-2-carboxylic acid [5-(3-chloro-phenyl)-2-oxo-5-phenyl-2,3-dihydro-1H-benzo[e][1,4]diazepin-3-yl]-amide;
Thiophene-2-carboxylic acid [5-3-chlorophenyl)-2-oxo-5-phenyl-2,3-dihydro-1H-benzo[e][1,4]diazepin-3-yl]-amide;
Cyclohexanecarboxylic acid [5-(3chloro-phenyl)-2-oxo-5-phenyl-2,3-dihydro-1H-benzo[e][1,4]diazepin-3-yl]-amide;
Piperidine-1-carboxylic acid [5-3-chloro-phenyl)-2-oxo-5-phenyl-2,3-dihydro-1H-benzo[e][1,4]diazepin-3-yl]-amide;
N-[5-(3-Chloro-phenyl)-2-oxo-5-phenyl-2,3-dihydro-1H-benzo[e][1,4]diazepin-3-yl]isonicotinamide;
5-Methyl-furan-2-carboxylic acid (2-oxo-5-phenyl-2,3-dihydro-1H-benzo[e][1,4]diazepin-3-yl)-amide;
Pyrazine-2-carboxylic acid (2-oxo-5-phenyl-2,3-dihydro-1H-benzo[e][1,4]diazepin-3-yl)-amide;
N-[5-(3-Methoxy-phenyl)-2-oxo-5-phenyl-2,3-dihydro-1H-benzo[e][1,4]diazepin-3-yl]-isobutyramide;
Thiophene-2-carboxylic acid [5-(3-methoxy-phenyl)-2-oxo-5-phenyl-2,3-dihydro-1H-benzo[e][1,4]diazepin-3-yl]-amide;
Cyclohexanecarboxylic acid [5-3-methoxy-phenyl)-2-oxo-5-phenyl-2,3-dihydro-1H-benzo[e][1,4]diazepin-3-yl]-amide;
Piperidine-1-carboxylic acid [5-(3-methoxy-phenyl)-2-oxo-5-phenyl-2,3-dihydro-1H-benzo[e][1,4]diazepin-3-yl]-amide;
Piperidine-4-carboxylic acid [5-(3-methoxy-phenyl)-2-oxo-5-phenyl-2,3-dihydro-1H-benzo[e][1,4]diazepin-3-yl]-amide;
Cyclohexanecarboxylic acid (8-chloro-2-oxo-5-phenyl-2,3-dihydro-1H-benzo[e][1,4]diazepin-3-yl)-amide;
Thiophene-2-carboxylic acid (8-methyl-2-oxo-5-phenyl-2,3-dihydro-1H-benzo[e][1,4]diazepin-3-yl)-amide;
1-(2-Oxo-5-phenyl-2,3-dihydro-1H-benzo[e][1,4]diazepin-3-yl)-3-thiophene-2-yl-urea;
1-(2-Oxo-5-phenyl-2,3-dihydro-1H-benzo[e][1,4]diazepin-3-yl)-3-thiophene-3-yl-urea;
Pyridine-2-carboxylic acid (2-oxo-5-phenyl-2,3-dihydro-1H-benzo[e][1,4]diazepin-3-yl)-amide;
1H-Pyrazole-4-carboxylic acid (2-oxo-5-phenyl-2,3-dihydro-1H-benzo[e][1,4]diazepin-3-yl)-amide;
6-Dimethylamino-N-(2-oxo-5-phenyl-2,3-dihydro-1H-benzo[e][1,4]diazepin-3-yl)-nicotinamide;
2-Ethoxy-naphthalene-1-carboxylic acid (2-oxo-5-phenyl-2,3-dihydro-1H-benzo[e][1,4]diazepin-3-yl)-amide;
9-Oxo-9H-fluorene-1-carboxylic acid (2-oxo-5-phenyl-2,3-dihydro-1H-benzo[e][1,4]diazepin-3-yl)-amide;
2-Oxo-2,3-dihydro-benzoimidazole-1-carboxylic acid (2-oxo-5-phenyl-2,3-dihydro-1H-benzo[e][1,4]diazepin-3-yl)-amide;
(2-Oxo-5-phenyl-2,3dihydro-1H-benzo[e][1,4]diazepin-3-yl)carbamic acid tert-butyl ester;
(S)-4,5-Dibromo-furan-2-carboxylic acid (2-oxo-5-phenyl-2,3-dihydro-1H-benzo[e][1,4]diazepin-3-yl)-amide;
(S)-Benzofuran-2-carboxylic acid (2-oxo-5-phenyl-2,3-dihydro-1H-benzo[e][1,4]diazepin-3-yl)-amide;
(2-Oxo-5-phenyl-2,3-dihydro-1H-benzo[e][1,4]diazepin-3-yl)-carbamic acid methyl ester;
(2-Oxo-5-phenyl-2,3-dihydro-1H-benzo[e][1,4]diazepin-3-yl)-carbamic acid ethyl ester;

(2-Oxo-5-phenyl-2,3-dihydro-1H-benzo[e][1,4]diazepin-3-yl)-carbamic acid isobutyl ester; and
2-Oxo-N-(2-oxo-5-phenyl-2,3-dihydro-1H-benzo[e][1,4]diazepin-3-yl)-2-thiophene-2-yl-acetamide, and pharmaceutically acceptable salts thereof.

Compounds of formula (I) may be prepared by reacting glyoxylic acid (HCO—C₂H), benzotriazole and an appropriate benzyl carbamate at reflux in toluene, under Dean-Stark conditions giving the key protected amino acid of formula (II)

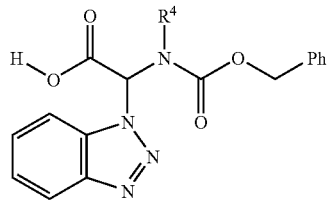
(II)

The thus obtained amino acid of formula (II) can then be reacted with a suitable chlorinating agent, such as oxalyl chloride, followed by reaction with a 2-aminobenzophenone of formula (III)

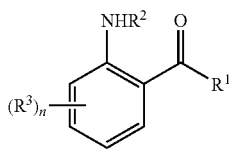
(III)

to give the intermediate amide of formula (IV)

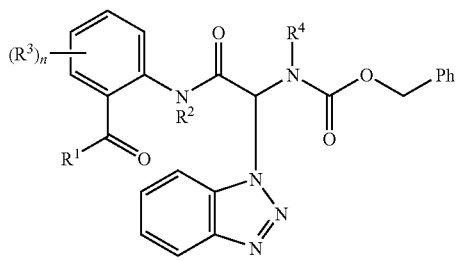
(IV)

which need not be characterized.

The compound of formula (IV) can then be subjected to ammonolysis followed by ring closure in acetic acid containing ammonium acetate to obtain the protected benzodiazepine of formula (V)

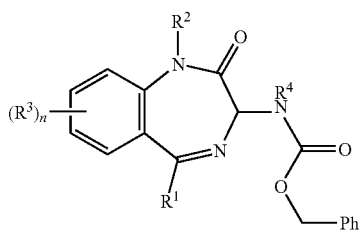
(V)

The compound of formula (V) can then be deprotected using hydrogen bromide in acetic acid to yield the deprotected amine of formula (VI).

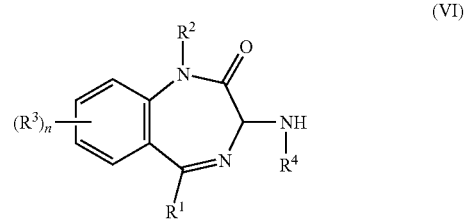
(VI)

Compounds of formula (I), in which $R^5$ is $XR^6$ and X is —CO— can be prepared by reacting a compound of formula (VI), as defined above, with an acid anhydride in a suitable solvent, preferably pyridine at ambient temperature, or with an acid chloride in a suitable solvent in the presence of a base, preferably in THF at ambient temperature with triethylamine present. Alternatively, the compounds can be produced by reaction of a compound of formula (VI) with an acid in a suitable solvent in the presence of a base and a coupling agent, preferably in THF at ambient temperature with triethylamine and O-benzotriazol-1-yl-N,N,N',N'-tetramethyluronium hexafluorophosphate (HBTU) present.

If the acid chloride used is an amino carbonyl chloride, the compound of formula (I) is a tertiary urea. In the case where $R^6$ is NH—R', such compounds may be prepared by the reaction of a compound of formula (VI) with an isocyanate. This reaction is preferably carried out in THF at ambient temperature. Alternatively, the isocyanate may be prepared in situ from the relevant amine and phosgene, in the presence of a base, usually triethylamine, again in THF.

Compounds of formula (I), in which $R^5$ is —$XR^6$ and X is —$S(O)_2$— may be prepared by the reaction of a compound of formula (VI) with a suitable sulfonyl chloride. Similarly, compounds of formula (I), in which $R^5$ is $XR^6$ and X is —S(O)— may be prepared by the reaction of a compound of formula (VI) with a suitable sulfinyl chloride.

Compounds of formula (I) in which $R^5$ is not $XR^6$ may be prepared by known methods. For example, a compound of formula (VI) can be reacted with a compound of formula $R^5$-L, wherein L is a leaving group such as a chlorine atom, a mesylate group or a triflate group. When $R^5$ is aryl or heteroaryl, L can be —$B(OH)_2$ and the reaction may take place in the presence of copper acetate. Such boronic acid coupling reactions will, of course, be familiar to those of skill in the art. Compounds wherein $R^5$ is aryl or heteroaryl may also be prepared by way of a Buchwald reaction or by reaction of a compound of formula (VI) with an appropriate fluoroaryl or fluoroheteroaryl compound. Compounds wherein $R^5$ is a heteroaryl group may also be prepared by reaction of a compound of formula (VI) with a suitable chloroheteroaryl or bromoheteroaryl compound. Compounds wherein $R^5$ is a carbocyclyl group may also be prepared by known methods, for example a compound wherein $R^5$ is cyclohexyl may be prepared by the reaction of a compound of formula (VI) with cyclohexanone in the presence of a reducing agent.

Compounds of formula (I) in which the $R^5$ group is aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- can also be prepared by the reaction of a compound of formula (VI) with an aldehyde in the presence of a reducing agent. Preferably, such reactions between compounds of formula (VI) and aldehydes are carried out in a mixture of dichloromethane and acetic acid in the presence of sodium (triacetoxy)borohydride at ambient temperature.

In the preparation of the benzodiazepine skeleton, commercially available aminobenzophenone compounds of formula (III) can be used where possible. Compounds of formula (III) which are not commercially available can be prepared by known methods, for example by reaction of a Weinreb type amide of formula (VII)

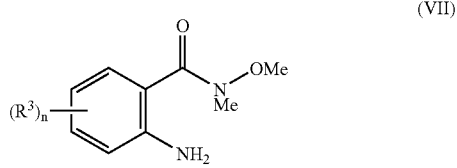

(VII)

with a group $R^1$-Li or a Grignard reagent such as $R^1$—MgBr. Preferably this reaction is carried out in THF at −100° C.

Compounds of formula (VII) are known compounds or can be prepared by analogy with known methods. For example, they can be prepared from the reaction of isatoic anhydrides of formula (VIII)

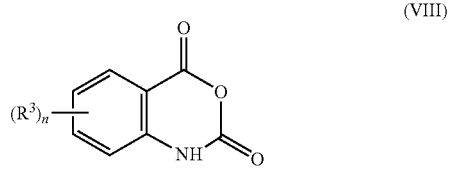

(VIII)

with N,O-dimethyl hydroxylamine under standard reaction conditions.

The starting materials of formula (II), (II), (VII), and (VIII) are known compounds, or may be prepared by analogy with known methods.

Further synthetic manipulation of the thus obtained compounds of formula (I) may be carried out by conventional methods to achieve further compounds of formula (I). The benzodiazepines of formula (I) can be salified by treatment with an appropriate acid or base.

Although the described route to the claimed compounds provides an adequate synthesis for laboratory scale preparations, an alternative route was sought which has potential as a manufacturing route. The same starting material (2-aminobenzophenone) (1) is used in both, however in the alternative route, the benzodiazepine ring system is formed by reaction initially with bromoacetyl bromide (or an equivalent reagent) followed by ring closure with ammonia. These reactions are carried out in a suitable solvent, such as dichloromethane, and at a suitable temperature which may range from −20 to 150° C. In order to protect the NH functionality, at this stage the unsubstituted benzodiazepine is reacted with a base, and an alkylating agent. For instance sodium hydride in DMF followed by addition of 4-methoxy-benzyl chloride gives rise to the intermediate (2) shown below. Further reaction of this material with a base (e.g. potassium tert-butoxide) in a suitable solvent (e.g. THF or DMF) followed by quenching with isoamyl nitrite (or an alternative similar reagent) furnishes the oxime intermediate (3) which may be converted into the racemic primary amine by methods which include the use of hydrogen and a suitable catalyst. This amine then undergoes a Dynamic Kinetic Resolution (DKR) procedure by which the racemic amine in the presence of a suitable optically active acid, and a suitable aldehyde gives rise to precipitation of the salt of the desired (S)-amine (4) in good yield and exceptionally high enantiomeric excess. A suitable acid for this conversion can be e.g. Camphorsulfonic acid, Boc-phenyl alanine or the like, and a suitable aldehyde may be a benzaldehyde such as 3,5-dichloro salicylaldehyde.

The optically amine thus formed may then be transformed into a desired derivative, such as an amide or urea. The amide formations may be carried out using a suitable carboxylic acid and a coupling reagent, or a carbonyl chloride or other suitable reagent, and the ureas prepared using either a suitable isocyanate, or alternatively reaction with phosgene followed by a suitable amine.

These derivatives thus formed may then have the protecting group removed. This may be carried out in the presence of a Lewis Acid, such as aluminium chloride, boron trifluoride, titanium tetrachloride, or the like. These reactions are carried out in a suitable inert solvent, such as dichloromethane. Reaction temperatures may range from −20 to 150° C., but are typically carried out at room temperature or below.

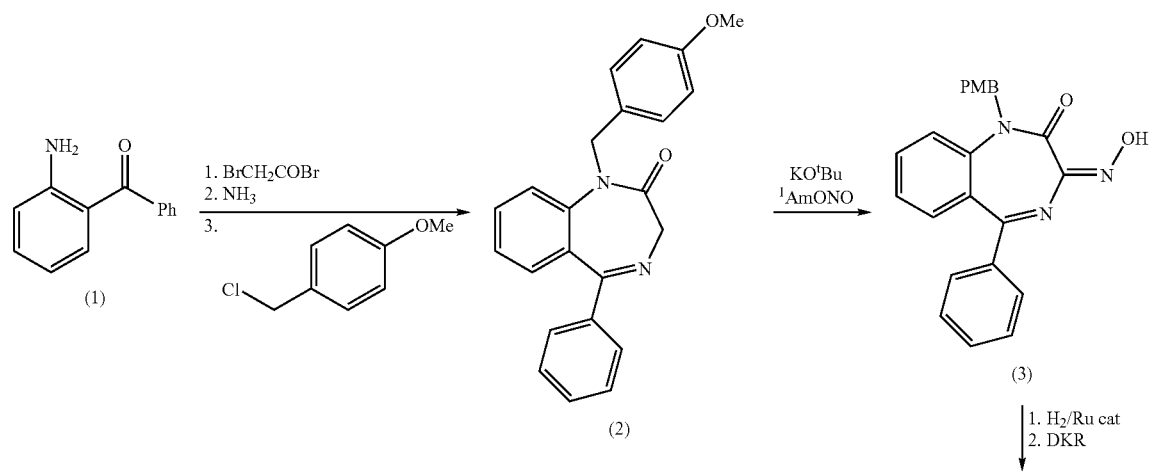

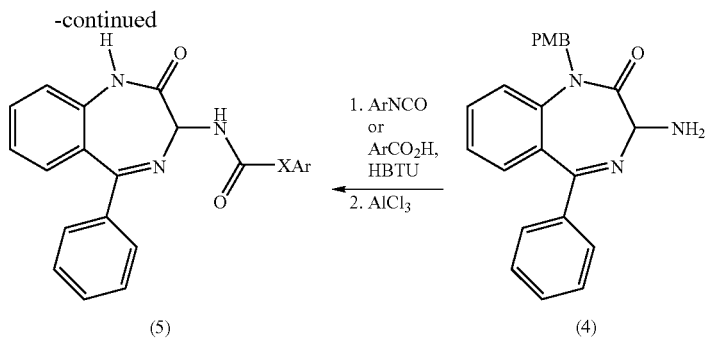

As explained above, the compounds of the invention are active against RSV. The present invention therefore provides a method for treating a patient suffering from or susceptible to an RSV infection, which method comprises administering to said patient an effective amount of a compound of formula (I) or a pharmaceutically acceptable salt thereof.

RSV is prevalent among children younger than two years of age. It is a particularly serious risk amongst any such children who suffer from chronic lung disease. Accordingly, the said medicament is typically for use in treating a patient who is a child under two years of age. Typically, said child suffers from chronic lung disease.

Further, anti-RSV prophylaxis is recommended for infants born at 32 weeks of gestation or earlier, until they reach 6 months of age. Accordingly, the said medicament is typically for use in preventing RSV infection in an infant less than 6 years of age, who was born after 32 weeks of gestation or less.

It has been shown that RSV infections are accompanied by inflammatory reactions (Noah et al, Clinical Immunology 2000, Vol 97, 43-49). The present invention also relates to a combination of a compound of formula (I), or a pharmaceutically acceptable salt thereof, with an anti-inflammatory compound and the use of such a combination in the treatment of RSV. Typically, said anti-inflammatory compound is a steroid, for example budesonide or fluticasone, a non-steroid, for example a leukotriene antagonist, phosphodiesterase 4 inhibitor or TNF alpha inhibitor or an interleukin 8 or interleukin 9 inhibitor.

Thus, in one embodiment, a compound of formula (I), or pharmaceutically acceptable salt thereof, is combined with a steroid antiinflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections.

It is a further surprising finding of the present invention that compounds of the invention are active against human metapneumovirus, measles, parainfluenza viruses and mumps. The present invention thus provides the use of a compound of formula (I), or a pharmaceutically acceptable salt thereof, in the manufacture of a medicament for use in the treatment of human metapneumovirus, measles, parainfluenza viruses and mumps. It is an additional surprising finding of the present invention that compounds of the invention are active against yellow fever virus (B5 strain), Dengue 2 virus and West Nile virus. The present invention thus provides the use of a compound of formula (I), or a pharmaceutically acceptable salt thereof, in the manufacture of a medicament for use in the treatment of yellow fever virus (B5 strain), Dengue 2 virus and West Nile virus.

The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In a preferred embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch;

lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

A therapeutically effective amount of a compound of the invention is administered to a patient A typical dose is from about 0.001 to 50 mg per kg of body weight, according to the activity of the specific compound, the age, weight and conditions of the subject to be treated, the type and severity of the disease and the frequency and route of administration. Preferably, daily dosage levels are from 5 mg to 2 g.

Certain benzodiazepine derivatives of the formula (I) are novel per se. The present invention includes these novel compounds and pharmaceutically acceptable salts thereof. The present invention therefore also provides compounds of formula (Ib) and pharmaceutically acceptable salts thereof

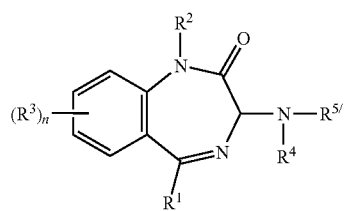

(Ib)

wherein:

$R^1$ represents $C_{1-6}$ alkyl, aryl or heteroaryl;

$R^2$ represents hydrogen, $C_{1-6}$ alkyl;

each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl) amino, di($C_{1-6}$ alkyl)amino, nitro, cyano, —$CO_2R'$, —CONR'R", —NH—CO—R', —S(O)R', —S(O)$_2$R', —NH—S(O)$_2$R', —S(O)NR'R" or —S(O)$_2$NR'R", wherein each R' and R" is the same or different and represents hydrogen or $C_{1-6}$ alkyl;

n is from 0 to 3;

$R^4$ represents hydrogen or $C_{1-6}$ alkyl;

$R^{5'}$ represents $C_{3-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-C(O)—C(O)—, heteroaryl-C(O)—C(O)—, carbocyclyl-C(O)—C(O)—, heterocyclyl-C(O)—C(O)— or —X', provided that when $R^{5'}$ is heteroaryl it is not 2-quinaldyl or 6-chloro-pyrazinyl, when $R^{5'}$ is heteroaryl-($C_{1-6}$ alkyl)- it is not 2-indolylmethyl, 2-(3-indolyl)ethyl or 2-furanylmethyl, when $R^{5'}$ is aryl it is not unsubstituted phenyl and when $R^{5'}$ is aryl-($C_{1-6}$ alkyl)- it is not unsubstituted phenyl-($C_{1-2}$ alkyl)- or 4-chlorophenyl-($C_{2-3}$ alkyl)-;

X' represents —CO—$R^{6'}$, —S(O)—$R^{6''}$ or —S(O)$_2$—$R^{6'''}$;

$R^6$ represents $C_1$ alkyl, hydroxy, $C_{1-6}$ alkoxy, $C_{1-6}$ alkylthio, aryl, heteroaryl, carbocyclyl, heterocyclyl, aryl-$C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)- or heterocyclyl-($C_{1-6}$ alkyl)-, provided that (a) when $R^{6'}$ is aryl it is not unsubstituted naphthyl, unsubstituted phenyl, mono-halophenyl, 4-methylphenyl, 4-methoxyphenyl, 4-hydroxyphenyl, 4-trifluoromethylphenyl, 4-nitrophenyl, 4-cyanophenyl, 4-n-propylphenyl, 4t-butylphenyl, 4-n-pentylphenyl, 4-dimethylaminophenyl, 4-methylthiophenyl, 3-trifluoromethylthiophenyl, 3,4-dimethoxyphenyl, 3,4-dichlorophenyl, 3,5-dichlorophenyl, 2,3,4,5,6-pentafluorophenyl, 4-chloro-2-aminophenyl or 4-1,1-dimethylethylphenyl, (b) when $R^{6'}$ is heteroaryl it is not 2-pyrrolyl, 2-pyrazinyl, 2-quinaldyl, 2-quinoxalinyl, 1-methylindonly, 2-methyl-indolyl, 2-benzofuranyl, 2-benzothienyl, 3-thienyl, 3-indolyl, unsubstituted 2-indolyl, 5-fluoroindol-2-yl, 5-chloroindol-2-yl, 5-bromoindol-2-yl, 5-hydroxyindol-2-yl or 5-methoxyindol-2-yl, (c) when $R^{6'}$ is aryl-($C_{1-6}$ alkyl)- it is not 4-thianaphthene-CH$_2$)—, unsubstituted phenyl-CH$_2$)—, 4-trifluoromethylphenyl-(CH$_2$)—, unsubstituted phenyl-(CH$_2$)$_3$—, monotrifluoromethylphenyl-CH$_2$)$_2$—, 3-methoxyphenyl-(CH$_2$)$_2$—, 4-chloro-2-aminophenyl-(CH$_2$)$_2$—, 2,4-dichlorophenyl-(CH$_2$)$_2$—, monochlorophenyl-(CH$_2$)$_2$—, 2,4-trifluoromethyl phenyl-(CH$_2$)$_2$—, 4-cyanophenyl-(CH$_2$)$_2$— or 3-cyanophenyl-(CH$_2$)$_2$—, (d) when $R^{6'}$ is heteroaryl-($C_{1-6}$ alkyl)- it is not indolyl-(CH$_2$)$_x$—, wherein x is 1, 2, 3, unsubstituted furanyl-(CH$_2$)$_2$—, unsubstituted thienyl-(CH$_2$)$_3$— (e) when $R^{6'}$ is carbocyclyl it is not cyclohexyl, (f) when $R^{6'}$ is carbocyclyl-($C_{1-6}$ alkyl)- it is not unsubstituted cyclohexyl-(CH$_2$)$_{1-3}$—, (g) when $R^{6'}$ is heterocyclyl it is not N-pyrrolidinyl or 2-dihydrobenzofuranyl, (h) when $R^{6'}$ is aryl-($C_{1-6}$ alkyl)-O— it is not unsubstituted phenyl-(CH$_2$)—O—, and (i) when R' is hydrogen, R" is not unsubstituted phenyl, 4-halophenyl, 3-halophenyl, methoxyphenyl, nitrophenyl, 2-chlorophenyl, 4-methylphenyl, dichlorophenyl, 3,5-dimethylphenyl, 3-methylphenyl, 3-cyanophenyl, 3-aminophenyl, 3-aminocarbonylphenyl, 3-benzoic acid, 3-benzoic acid ethyl ester, 6-amino-3-pyridyl, 5-(2-chloro)pyridyl, 5-2-methoxy)pyridyl, 5-indanyl, unsubstituted cyclohexyl, 1,1-dimethylethyl, unsubstituted phenyl-$CH_2$—, unsubstituted naphthyl or benzotriazol-3-yl and when R' is methyl, R" is not cyclopropylbenzene;

$R^{6\prime\prime}$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl($C_{1-6}$ alkyl)-, carbocyclyl-($C_{1-6}$ alkyl)-, heterocyclyl-($C_{1-6}$ alkyl)-, aryl-$C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-$C_{1-6}$ alkyl)-, carbocyclyl-$C_{1-6}$ alkyl)- or heterocyclyl-($C_{1-6}$ alkyl)-; and $R^{6\prime\prime\prime}$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-$C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-$C_{1-6}$ alkyl)-, heteroaryl-($C_{1-6}$ alkyl)-, carbocyclyl-($C_{1-6}$ alkyl)- or heterocyclyl-($C_{1-6}$ alkyl)-, provided that when $R^{6\prime\prime\prime}$ is aryl it is not 4-methylphenyl, provided that the compound of formula (Ib) is not N-(2-Oxo-5-phenyl-2,3-dihydro-1H-benzo[e][1,4]diazepin-3-yl)-acetamide.

Preferably, in the formula (Ib), each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl) amino, di($C_{1-6}$ alkyl)amino, nitro, cyano, —$CO_2R'$, —CONR'R", —NH—CO—R', —S(O)R', —S(O)$_2R'$, —NH—S(O)$_2R'$ or —S(O)NR'R", wherein each R' and R" is the same or different and represents hydrogen or $C_{1-6}$ alkyl;

$R^{5\prime}$ represents $C_{2-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —X', provided that when $R^{5\prime}$ is heteroaryl it is not 2-quinaldyl or 6-chloro-pyrazinyl and when $R^{5\prime}$ is heteroaryl-($C_{1-6}$ alkyl)- it is not 2-indolylmethyl or 2-(3-indolyl)ethyl;

X' represents —CO—$R^{6\prime}$, —S(O)—$R^{6\prime\prime}$ or —S(O)$_2$—$R^{6\prime\prime\prime}$;

$R^{6\prime}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$C_{1-6}$ alkyl)-, heteroaryl-($C_{1-6}$alkyl)-, carbocyclyl-($C_{1-6}$ alkyl)-, heterocyclyl-$C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)- or heteroamyl-($C_{1-6}$ alkyl)-, provided that (a) when $R^{6\prime}$ is aryl it is not unsubstituted naphthyl, unsubstituted phenyl, mono-halophenyl, 4-methylphenyl, 4-methoxyphenyl, 4-hydroxyphenyl, 4-trifluoromethylphenyl, 4-nitrophenyl, 4-cyanophenyl, 4-n-propylphenyl, 4-t-butylphenyl, 4-n-pentylphenyl, 4-dimethylaminophenyl, 4-methylthiophenyl, 3-trifluoromethylthiophenyl, 3,4-dimethoxyphenyl, 3,4-dichlorophenyl, 3,5-dichlorophenyl or 2,3,4,5,6-pentafluorophenyl, (b) when $R^{6\prime}$ is heteroaryl it is not 2-pyrrolyl, 2-pyrazinyl, 2-quinaldyl, 2-methyl-indolyl, 2-benzofuranyl, 2-benzothienyl, 3-thienyl, 3-indolyl, unsubstituted 2-indolyl, 5-fluoroindol-2-yl, 5-chloroindol-2-yl, 5-bromoindol-2-yl, 5-hydroxyindol-2-yl or 5-methoxyindol-2-yl, (c) when $R^{6\prime}$ is aryl-($C_{1-6}$ alkyl)- it is not 4-thianaphthene-($CH_2$)—, (d) when $R^{6\prime}$ is heteroaryl-($C_{1-6}$ alkyl)- it is not -indolyl-($CH_2$)$_x$—, wherein x is 1, 2, 3, and (e) when R' is hydrogen, R" is not 4-halophenyl, 3-methylphenyl, 3-cyanophenyl, 3-aminophenyl, 3-aminocarbonylphenyl, 3-benzoic acid, 3-benzoic acid ethyl ester, 6-amino-3-pyridyl, 5-(2-chloro)pyridyl, 5-2-methoxy)pyridyl, 5-indanyl or benzotriazol-3-yl;

$R^{6\prime\prime}$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-$C_{1-6}$ alkyl)- or heteroaryl-($C_{1-6}$ alkyl)-; and $R^{6\prime\prime\prime}$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)- or heteroaryl-($C_{1-6}$ alkyl)-, provided that when $R^{6\prime\prime\prime}$ is aryl it is not 4-methylphenyl.

Preferred $R^1$, $R^2$, $R^3$ and $R^4$ groups in the formula (Ib) include those preferred groups set out above as preferred $R^1$, $R^2$, $R^3$ and $R^4$ groups in the formula (I). Preferred compounds of formula (Ib) include the particularly preferred compounds of formula (I) named above.

Typically, in the formula (Ib), $R^2$ is hydrogen.

Preferred compounds of formula (Ib) are those in which:

$R^{5\prime}$ represents $C_{3-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl), -aryl-C(O)—C(O)—, heteroaryl-C(O)—C(O)—, carbocyclyl-C(O)—C(O)—, heterocyclyl-C(O)—C(O)— or —X', provided that when $R^{5\prime}$ is heteroaryl it is not quinaldyl or pyrazinyl, when $R^{5\prime}$ is heteroaryl-($C_{1-6}$ alkyl)- it is not indolyl-($CH_2$)$_x$—, wherein x is 1 or 2, or furanylmethyl, when $R^{5\prime}$ is aryl it is not phenyl and when $R^{5\prime}$ is aryl-($C_{1-6}$ alkyl)- it is not phenyl-($C_{1-3}$ alkyl)-;

X' represents —CO—$R^{6\prime}$, —S(O)—$R^{6\prime\prime}$ or —S(O)$_2$—$R^{6\prime\prime\prime}$;

$R^{6\prime}$ represents $C_1$alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-$C_{1-6}$ alkyl)- or heterocyclyl-($C_{1-6}$ alkyl)- provided that (a) when $R^{6\prime}$ is aryl it is not phenyl or naphthyl, (b) when $R^{6\prime}$ is heteroaryl it is not thienyl, pyrrolyl, pyrazinyl, quinaldyl, quinazolidinyl, indolyl, benzofuranyl or benzothienyl, (c) when $R^{6\prime}$ is aryl-($C_{1-6}$ alkyl)- it is not thianaphthene-($CH_2$)— or phenyl-($CH_2$)$_{1-3}$—, (d) when $R^{6\prime}$ is heteroaryl-($C_{1-6}$ alkyl)- it is not indolyl-($CH_2$)$_x$—, wherein x is 1, 2 or 3, thienyl-($CH_2$)$_3$— or furanyl- $(CH_2)_2$—, (e) when $R^{6'}$ is carbocyclyl it is not cyclohexyl, -, (f) when $R^{6'}$ is heterocyclyl it is not pyrrolidinyl or dihydrobenzofuranyl, (g) when $R^{6'}$ is carbocyclyl-$(C_{1-6}$ alkyl)- it is not cyclohexyl-$C_{1-3}$ alkyl)-, (h) when $R^{6'}$ is aryl-$(C_{1-6}$ alkyl)-O— it is not phenyl-$(CH_2)$—O— and (i) when R' is hydrogen, R" is not phenyl, pyridyl, indanyl, $C_4$ alkyl, cyclophenyl, naphthyl, phenyl-$CH_2$—, benzotriazolyl and when R' is methyl R" is not cyclopropylbenzene;

$R^{6'''}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$C_{1-6}$ alkyl)-, heteroaryl-$(C_{1-6}$ alkyl)-, carbocyclyl-$(C_{1-6}$ alkyl)-, heterocyclyl-$(C_{1-6}$ alkyl)-, aryl-$(C_{1-6}$ hydroxyalkyl)-, heteroaryl-$(C_{1-6}$ hydroxyalkyl)-, carbocyclyl-$(C_{1-6}$ hydroxyalkyl)-, heterocyclyl-$(C_{1-6}$ hydroxyalkyl)-, aryl-$C_{1-6}$ alkyl)-O—, heteroaryl-$(C_{1-6}$ alkyl)-O—, carbocyclyl-$(C_{1-6}$ alkyl)-O—, heterocyclyl-$(C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-$C_{1-6}$ alkyl)-, heteroaryl-$(C_{1-6}$ alkyl)-, carbocyclyl-$(C_{1-6}$ alkyl)- or heterocyclyl-$(C_{1-6}$ alkyl)-; and $R^{6''''}$ represents $C_{1-18}$ alkyl, hydroxy, $C_{1-6}$ alkoxy, $C_{1-6}$ alkylthio, aryl, heteroaryl, carbocyclyl, heterocyclyl, aryl-$(C_{1-6}$ alkyl)-, heteroaryl-$(C_{1-6}$ alkyl)-, carbocyclyl-$(C_{1-6}$ alkyl)-, heterocyclyl-$(C_{1-6}$ alkyl)-, aryl-$(C_{1-6}$ hydroxyalkyl)-, heteroaryl-$(C_{1-6}$ hydroxyalkyl)-, carbocyclyl-$(C_{1-6}$ hydroxyalkyl)-, heterocyclyl-$(C_{1-6}$ hydroxyalkyl)-, aryl-$(C_{1-6}$ alkyl)-O—, heteroaryl-$(C_{1-6}$ alkyl)-O—, carbocyclyl-$(C_{1-6}$ alkyl)-O—, heterocyclyl-$(C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-$(C_{1-6}$ alkyl)-, heteroaryl-$(C_{1-6}$ alkyl)-, carbocyclyl-$(C_{1-6}$ alkyl)- or heterocyclyl-$(C_{1-6}$ alkyl)-, provided that when $R^{6''''}$ is aryl it is not methylphenyl.

Examples of preferred compounds of formula (Ib) are compounds defined above as preferred compounds of formula (Ib) wherein:

$R^{5'}$ represents $C_{2-6}$ alkyl, aryl, heteroaryl, carbocyclyl, heterocyclyl, aryl-$(C_{1-6}$ alkyl)-, heteroaryl-$(C_{1-6}$ alkyl)-, carbocyclyl-$(C_{1-6}$ alkyl)-; heterocyclyl-$C_{1-6}$ alkyl)- or —X', provided that when $R^{5'}$ is heteroaryl it is not quinaldyl or pyrazinyl and when $R^{5'}$ is heteroaryl-$(C_{1-6}$ alkyl)- it is not indolyl-$(CH_2)_x$—, wherein x is 1 or 2;

$R^{6'}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$(C_{1-6}$ alkyl)-, heteroaryl-$(C_{1-6}$ alkyl)-, carbocyclyl-$(C_{1-6}$ alkyl)-, heterocyclyl-$(C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-$(C_{1-6}$ alkyl)- or heteroaryl-$C_{1-6}$ alkyl)-, provided that (a) when $R^{6'}$ is aryl it is not phenyl or naphthyl, (b) when $R^{6'}$ is heteroaryl it is not thienyl, pyrrolyl, pyrazinyl, quinaldyl, indolyl, benzofuranyl or benzothienyl, (c) when $R^{6'}$ is aryl-$(C_{1-6}$ alkyl)- it is not thianaphthene-$(CH_2)$—, (d), when $R^{6'}$ is heteroaryl-$(C_{1-6}$ alkyl)- it is not indolyl-$CH_2)_x$—, wherein x is 1, 2, 3, and (e) when R' is hydrogen, R" is not phenyl, pyridyl, indanyl or benzotriazolyl;

$R^{6''}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$(C_{1-6}$ alkyl)-, heteroaryl-$(C_{1-6}$ alkyl)-, carbocyclyl-$(C_{1-6}$ alkyl)-, heterocyclyl-$(C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-$(C_{1-6}$ alkyl)- or heteroaryl-$(C_{1-6}$ alkyl)-; and $R^{6'''}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$(C_{1-6}$ alkyl)-, heteroaryl-$(C_{1-6}$ alkyl)-, carbocyclyl-$C_{1-6}$ alkyl)-, heterocyclyl-$(C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-$(C_{1-6}$ alkyl)- or heteroaryl-$(C_{1-6}$ alkyl)-, provided that when $R^{6'''}$ is aryl it is not methylphenyl.

Further preferred compounds of formula (Ib) are those wherein:

$R^{5'}$ is $C_{3-6}$ alkyl $C_{3-6}$ cycloalkyl, heterocyclyl, $C_{3-6}$ cycloalkyl-$C_{1-6}$ alkyl), aryl-C(O)—C(O)—, heteroaryl-C(O)—C(O)—, carbocyclyl-C(O)—C(O)—, heterocyclyl-C(O)—C(O)— or —X';

X' is —CO—$R^{6'}$, —S(O)—$R^{6'''}$ or —S(O)$_2$—$R^{6''''}$;

$R^{6'}$ is $C_1$ alkyl, hydroxy, $C_{1-6}$ alkoxy, $C_{1-6}$ alkylthio, heterocyclyl-$(C_{1-6}$ alkyl)-, aryl-$(C_{1-6}$ hydroxyalkyl)-, heteroaryl-$(C_{1-6}$ hydroxyalkyl)-, carbocyclyl-$(C_{1-6}$ hydroxyalkyl)-, heterocyclyl-$(C_{1-6}$ hydroxyalkyl)-, heteroaryl-$(C_{1-6}$ alkyl)-O—, carbocyclyl-$(C_{1-6}$ alkyl)-O—, heterocyclyl-$(C_{1-6}$ alkyl)-O— or —NR'R" wherein each R' and R" is the same or different and represents hydrogen, $C_{1-6}$ alkyl, $C_{3-6}$ cycloalkyl, heterocyclyl, carbocyclyl-$(C_{1-6}$ alkyl)- or heterocyclyl-$(C_{1-6}$ alkyl)-;

$R^{6''}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$(C_{1-6}$ alkyl)-, heteroaryl-$(C_{1-6}$ alkyl)-, carbocyclyl-$(C_{1-6}$ alkyl)-, heterocyclyl-$(C_{1-6}$ alkyl)-, aryl-$(C_{1-6}$ hydroxyalkyl)-, heteroaryl-$(C_{1-6}$ hydroxyalkyl)-, carbocyclyl-$(C_{1-6}$ hydroxyalkyl)-, heterocyclyl-$(C_{1-6}$ hydroxyalkyl)-, aryl-$(C_{1-6}$ alkyl)-O—, heteroaryl-$(C_{1-6}$ alkyl)-O—, carbocyclyl-$(C_{1-6}$ alkyl)-O—, heterocyclyl-$(C_{1-6}$ alkyl)-O— or —NR'R" wherein each R' and R" is the same or different and represents hydrogen, $C_{1-3}$ alkyl, heterocyclyl, heteroaryl, heteroaryl-$(C_{1-6}$ alkyl)-, carbocyclyl-$(C_{1-6}$ alkyl)- or heterocyclyl-$(C_{1-6}$ alkyl)-; and $R^{6'''}$ is $C_{1-6}$ alkyl, hydroxy, $C_{1-6}$ alkoxy, $C_{1-6}$ alkylthio, $C_{3-6}$ cycloalkyl, heterocyclyl, $C_{3-6}$ cycloalkyl-$(C_{1-6}$ alkyl)-, heterocyclyl-$(C_{1-6}$ alkyl)-, aryl-$(C_{1-6}$ hydroxyalkyl)-, heteroaryl-$(C_{1-6}$ hydroxyalkyl)-, carbocyclyl-$(C_{1-6}$ hydroxyalkyl)-, heterocyclyl-$(C_{1-6}$ hydroxyalkyl)-, aryl-$(C_{1-6}$ alkyl)-O—, heteroaryl-$(C_{1-6}$ allyl)-O—, carbocyclyl-$(C_{1-6}$ alkyl)-O—, heterocyclyl-$(C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-$(C_{1-6}$ alkyl)-, heteroaryl-$(C_{1-6}$ alkyl), carbocyclyl-$(C_{1-6}$ alkyl)- or heterocyclyl-$(C_{1-6}$ alkyl)-.

Examples of further preferred compounds of formula (Ib) are compounds as defined as further preferred compounds of formula (Ib) wherein:

$R^{5'}$ is $C_{2-6}$ alkyl, $C_{3-6}$ cycloalkyl, heterocyclyl, $C_{3-6}$ cycloalkyl-$(C_{1-6}$ alkyl), heterocyclyl-$(C_{1-6}$ alkyl) or —X';

X' is —CO—$R^{6'}$, —S(O)—$R^{6'''}$ or —S(O)$_2$—$R^{6''''}$;

$R^{6'}$ is $C_{1-6}$ alkyl, hydroxy, $C_{1-6}$ alkoxy, $C_{1-6}$ alkylthio, $C_{3-6}$ cycloalkyl, heterocyclyl, $C_{3-6}$ cycloalkyl-$(C_{1-6}$ alkyl)-, heterocyclyl-$(C_{1-6}$ alkyl)- or —NR'R" wherein each R' and R" is the same or different and represents hydrogen, $C_{1-6}$ alkyl, $C_{3-6}$ cycloalkyl or heterocyclyl;

$R^{6'''}$ represents $C_{1-6}$ alkyl, hydroxy, $C_{1-6}$ alkoxy, $C_{1-6}$ alkylthio, aryl, heteroaryl, carbocyclyl, heterocyclyl, aryl-$(C_{1-6}$ alkyl)-, heteroaryl-$(C_{1-6}$ alkyl)-, carbocyclyl-$(C_{1-6}$ alkyl)-, heterocyclyl-$(C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)- or heteroaryl-$C_{1-6}$ alkyl)-; and $R^{6'''}$ is $C_{1-6}$ alkyl, hydroxy, $C_{1-6}$ alkoxy, $C_{1-6}$ alkylthio, $C_{3-6}$ cycloalkyl, heterocyclyl, $C_{3-6}$ cycloalkyl-($C_{1-6}$ alkyl)-, heterocyclyl-($C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)- or heteroaryl-($C_{1-6}$ alkyl)-.

Preferably, in said further preferred compounds of formula (Ib), the cycloalkyl, heterocyclyl and carbocyclyl moieties in the groups $R^{5'}$, $R^{6'}$, $R^{6''}$ and $R^{6'''}$ are unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano, More preferably, in said further preferred compounds of formula (Ib), the cycloalkyl, heterocyclyl, carbocyclyl, aryl and heteroaryl moieties in the groups and R" are unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano.

Preferably, in said further preferred compounds of formula (Ib), the cycloalkyl, heterocyclyl and carbocyclyl moieties in the groups $R^{5'}$, $R^{6'}$, $R^{6''}$ and $R^{6'''}$ are unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano, More preferably, in said further preferred compounds of formula (Ib), the cycloalkyl, heterocyclyl, carbocyclyl, aryl and heteroaryl moieties in the groups R' and R" are unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano.

Particularly preferred novel compounds of the invention are compounds of formula (Ic) are pharmaceutically acceptable salts thereof

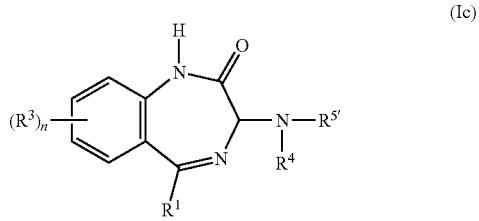

(Ic)

wherein:
$R^1$ is phenyl or methyl;
$R^3$ is methyl or chlorine;
n is 0 or 1;
$R^4$ is hydrogen or methyl;
$R^{5'}$ is phenyl-$CH_2$— thienyl-C(O)—C(O)— or —X';
X' is —CO—$R^{6'}$, —CONR'R", —S(O)$_2R^{6'''}$ or —S(O)$_2$—$NR_{40}R_{41}$; and
$R^{6'}$ is $C_1$ alkyl, $C_{1-4}$ alkoxy, benzodioxinyl, 9H-fluoren-9-onyl, furanyl, oxazolyl, isoxazolyl, pyrazolyl, pyridyl, cyclopentyl, piperazinyl, piperidinyl, morpholinyl, phenyl-$CH_2$—CH(OH)—, phenyl-CH(OH)—$CH_2$—, phenyl-($C_2$ alkyl)-O— or 1H-benzo[d]imidazol-2(3H)-only;

$R^{6'''}$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2CH$(OH)—, phenyl-CH(OH)—$CH_2$—, phenyl-($C_{1-2}$ alkyl)-O— or 1H-benzo[d]imidazol-2(3H)-only;

each R' and R" is the same or different and represents hydrogen, $C_{1-4}$ alkyl, phenyl, thienyl, cyclohexyl, cyclopentyl or phenyl-($CH_2$)—; and each $R_{.}$ and $R_{..}$ is the same or different and represents hydrogen, $C_{1-4}$ alkyl, phenyl, thienyl, cyclohexyl, cyclopentyl or phenyl-($CH_2$)—, wherein:

the phenyl moiety in the group $R^1$ being unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent;

the aryl moieties in the groups $R^{5'}$, $R^{6'}$ and $R^{6'''}$ being unsubstituted or substituted by 1, 2 or 3 substituents selected from fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-6}$ haloalkyl, $C_{1-4}$ haloalkoxy, amino, mono($C_{1-4}$ alkyl)amino, di($C_{1-4}$ alkyl)amino, nitro, —$CO_2$R', —$S(O)_2$R' and —$S(O)_2NH_2$, wherein R' represents $C_{1-2}$ alkyl;

the heteroaryl moieties in the groups $R^{5'}$, $R^{6'}$ and $R^{6'''}$ being unsubstituted or substituted by 1 or 2 substituents selected from fluorine, chlorine, bromine, $C_{1-2}$ alkyl, $C_{1-2}$ haloalkyl and di($C_{1-2}$ alkyl)amino;

the heterocyclyl and carbocyclyl moieties in the $R^{6'''}$ group being unsubstituted or substituted by 1 or 2 substituents selected from fluorine, chlorine, bromine, $C_{1-4}$ alkyl, $C_{1-4}$ alkoxy, $C_{1-4}$ haloalkyl and nitro;

the aryl, heteroaryl and carbocyclyl moieties in the R' and R" being unsubstituted or substituted by one or two substituents selected from fluorine, chlorine, bromine, $C_{1-2}$ alkyl, $C_{1-2}$ alkoxy, $C_{1-2}$ alkylthio, $C_{1-2}$ haloalkyl and nitro; and the aryl, heteroaryl and carbocyclyl moieties in the $R_{.}$ and $R_{..}$ being unsubstituted or substituted by one or two substituents selected from fluorine, chlorine, bromine, $C_{1-2}$ alkyl, $C_{1-2}$ alkoxy, $C_{1-2}$ alkylthio, $C_{1-2}$ haloalkyl and nitro, provided that the compound of formula (Ic) is not N-(2-Oxo-5-phenyl-2,3-dihydro-1H-benzo[e][1,4]diazepin-3-yl)-acetamide.

Examples of particularly preferred novel compounds of the present invention are compounds of formula (Ic') and pharmaceutically acceptable salts thereof

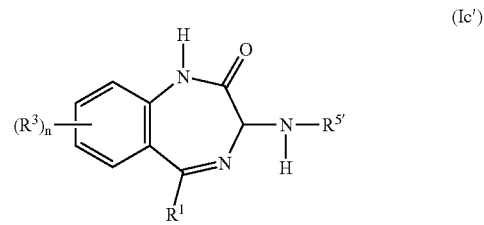

(Ic')

wherein:
$R^1$ is phenyl or methyl;
$R^3$ is chlorine;
n is 0 or 1;
$R^{5'}$ is phenyl-$CH_2$—, furanyl-$CH_2$— or —X';

X' is —CO—R⁶ᵗ, —CO—NR'R", —S(O)₂—R⁶ᵗᵗᵗ or —S(O)₂—NR.R..;

R⁶ᵗ is C₁₋₄ alkyl, 2-thienyl, furanyl, pyridyl, cyclopentyl, cyclohexyl, 3-benzothienyl, dihydrobenzofuranyl, isoxazolyl, piperidinyl, for example N-piperidinyl, morpholinyl, for example N-morpholinyl, piperazinyl, for example N-piperazinyl;

R⁶ᵗᵗᵗ is C₁₋₄ alkyl, phenyl, thienyl, furanyl, pyridyl, cyclopentyl, cyclohexyl, benzothienyl, dihydrobenzofuranyl, isoxazolyl, piperidinyl, for example N-piperidinyl, morpholinyl, for example N-morpholinyl or piperazinyl, for example N-piperazinyl;

each R' and R" is the same or different and represents hydrogen, C₁₋₄ alkyl, cyclohexyl, cyclopentyl, phenyl or phenyl-CH₂—, and each R. and R.. is the same or different and represents hydrogen, C₁₋₄ alkyl, cyclohexyl, cyclopentyl, phenyl or phenyl-CH₂— the phenyl, thienyl, furanyl, pyridyl, cyclopentyl, cyclohexyl, benzothienyl, dihydrobenzofuranyl, isoxazolyl, piperidinyl, morpholinyl and piperazinyl moieties in the groups R⁵ and R⁶ᵗ being unsubstituted or substituted by 1 or 2 substituents selected from fluorine, chlorine, bromine, C₁₋₄ alkyl, C₁₋₄ alkoxy, C₁₋₄ haloalkyl and nitro, the thienyl, furanyl, pyridyl, cyclopentyl, cyclohexyl, benzothienyl, dihydrobenzofuranyl, isoxazolyl, piperidinyl, morpholinyl and piperazinyl moieties in the group R⁶ᵗᵗᵗ being unsubstituted or substituted by 1 or 2 substituents selected from fluorine, chlorine, bromine, C₁₋₄ alkyl, C₁₋₄ alkoxy, C₁₋₄ haloalkyl and nitro, the phenyl moiety in the group Ie being unsubstituted or substituted by 1 or 2 substituents selected from fluorine, chlorine, bromine, C₂₋₄ alkyl, C₁₋₄ alkoxy, C₁₋₄ haloalkyl and nitro, the cyclohexyl and cyclopentyl moieties in the groups R' and R" being unsubstituted or substituted by a single fluoro, chloro, methyl, methoxy or nitro substituent the phenyl moiety in the groups R' and R" being unsubstituted or substituted by a single methoxy or nitro substituent, and the phenyl, cyclohexyl and cyclopentyl moieties in the groups R. and R.. being unsubstituted or substituted by a single fluoro, chloro, methyl, methoxy or nitro substituent.

Further preferred novel compounds of the present invention are compounds of formula (Ic), and pharmaceutically acceptable salts thereof, where:

R⁵ᵗ is —X';

X' is —CO—R⁶ᵗ, —CO—NR'R", —S(O)₂—R⁶ᵗᵗᵗ or —S(O)₂—NR.R..;

R⁶ᵗ is C₁₋₄ alkyl, pyridyl, cyclopentyl, cyclohexyl, dihydrobenzofuranyl, isoxazolyl, piperidinyl, for example N-piperidinyl, morpholinyl, for example N-morpholinyl, piperazinyl, for example N-piperazinyl;

R⁶ᵗᵗᵗ is C₁₋₄ alkyl, pyridyl, cyclopentyl, cyclohexyl, dihydrobenzofuranyl, isoxazolyl, piperidinyl, for example N-piperidinyl, morpholinyl, for example N-morpholinyl, piperazinyl, for example N-piperazinyl;

each R' and R" is the same or different and represents hydrogen, C₁₋₄ alkyl, cyclohexyl or cyclopentyl; and each R. and R.. is the same or different and represents hydrogen, C₁₋₄ alkyl, cyclohexyl, cyclopentyl, phenyl or phenyl-CH₂—, the pyridyl, cyclopentyl, cyclohexyl, dihydrobenzofuranyl, isoxazolyl, piperidinyl, morpholinyl, piperazinyl moieties in the groups R⁶ᵗ and R⁶ᵗᵗᵗ being unsubstituted or substituted by 1 or 2 substituents selected from fluorine, chlorine, bromine, C₁₋₄ alkyl, C₁₋₄ alkoxy, C₁₋₄ haloalkyl and nitro, and the phenyl, cyclohexyl and cyclopentyl moieties in the groups R', R", R. and R.. being unsubstituted or substituted by a single fluoro, chloro, methyl, methoxy or nitro substituent.

Further preferred novel compounds of the present invention are compounds of formula (Id) and pharmaceutically acceptable salts thereof

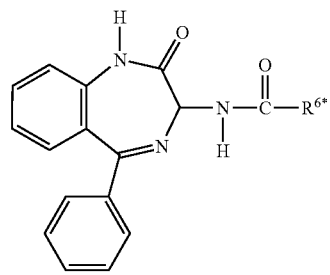

(Id)

wherein R⁶* is an aryl group which is unsubstituted or substituted by 1, 2 or 3 substituents selected from halogen, C₁₋₆ alkyl, C₂₋₇ acyl, hydroxy, C₁₋₆ alkoxy, C₁₋₆ alkylthio, C₁₋₆ haloalkyl, C₁₋₆ haloalkoxy, nitro, cyano, carbamoyl, mono(C₁₋₆ alkyl)carbamoyl, di(C₁₋₆ alkyl)carbamoyl, amino, mono(C₁₋₆ alkyl)amino, di(C₁₋₆ allyl)amino, —CO₂R', —CONR'R", —S(O)R', —S(O)₂R', —S(O)NR'R", —S(O)₂NR'R" —NH—S(O)₂R' or —NH—CO—R', wherein each R' and R" is the same or different and represents hydrogen or C₁₋₆ alkyl, provided that R⁶* is not a 4-chlorophenyl group.

Typically, in the compounds of formula (Id) R⁶* is a phenyl group which is unsubstituted or substituted by 1, 2 or 3 substituents selected from halogen, C₁₋₆ alkyl, C₂₋₇ acyl, hydroxy, C₁₋₆ alkoxy, C₁₋₆ alkylthio, C₁₋₆ haloalkyl, C₁₋₆ haloalkoxy, amino, mono(C₁₋₆ alkyl)amino, di(C₁₋₆ alkyl) amino, nitro, cyano, —CO₂R', —S(O)R', —S(O)₂R' and —S(O)₂NR'R", wherein each R' and R" is the same or different and represents hydrogen or C₁₋₄ alkyl, provided that R⁶* is not a 4-halophenyl group.

Preferably, in compounds of formula (Id), R⁶* is a phenyl group which is unsubstituted or substituted by 1, 2 or 3 substituents selected from fluorine, chlorine, bromine, iodine, C₁₋₄ alkyl, C₂₋₄ acyl, hydroxy, C₁₋₄ alkoxy, C₁₋₄ alkylthio, C₁₋₄ haloalkyl, C₁₋₄ haloalkoxy, amino, mono(C₁₋₄ alkyl)amino, di(C₁₋₄ alkyl)amino, nitro, —CO₂R', —S(O)₂R' and —S(O)₂NH₂, wherein R' represents C₁₋₂ alkyl, provided that R⁶* is not a monohalophenyl group.

More preferably, in compounds of formula (Id), R⁶* is a phenyl group which is unsubstituted or substituted by 1 or 2 substituents selected from C₁₋₂ alkyl, C₁₋₂ alkoxy, C₁₋₂ alkylthio, C₁₋₂ haloalkyl, C₁₋₂ haloalkoxy and nitro.

Further preferred novel compounds of the present invention are compounds of formula (Ie) and pharmaceutically acceptable salts thereof

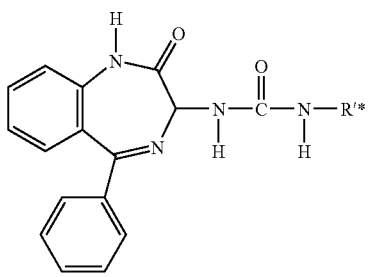

(Ie)

wherein R'* is an aryl group which is unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro.

Preferably, in compounds of formula (Ie), R'* is a phenyl group which is unsubstituted or substituted by one or two substituents selected from fluorine, chlorine, bromine, $C_{1-2}$ alkyl, $C_{1-2}$ alkoxy, $C_{1-2}$ alkylthio, $C_{1-2}$ haloalkyl and nitro.

More preferably, in compounds of formula (Ie), R'* is a phenyl group which is unsubstituted or substituted by a single fluorine, chlorine or bromine substituent.

The present invention also relates to the novel compounds, as defined above, or a pharmaceutically acceptable salt thereof, for use in a method of treating the human or animal body. The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

The following Examples illustrate the invention. They do not however, limit the invention in any way. In this regard, it is important to understand that the particular assays used in the Examples section are designed only to provide an indication of anti-RSV activity. There are many assays available to determine the activity of given compounds against RSV, and a negative result in any one particular assay is therefore not determinative.

EXAMPLES

In this section, all temperatures are in ° C. Flash column chromatography was carried out using Merck 9385 silica. Solid phase extraction (SPE) chromatography was carried out using Jones Chromatography (Si) cartridges under 15 mmHg vacuum with stepped gradient elution. Thin layer chromatography (TLC) was carried out on plastic plates.

LC-MS Conditions

Samples were run on a MicroMass ZMD, using electrospray with simultaneous positive-negative ion detection.

Column: YMC-PACK FL-ODS AQ, 50×4.6 mm I.D S-5 μm.

Gradient: 95:5 to 5:95 v/v $H_2O/CH_3CN$+0.05% Formic Acid over 4.0 min, hold 3 min, return to 95:5 v/v $H_2O/CH_3CN$+0.05% Formic Acid over 0.2 min and hold at 95:5 v/v $H_2O/CH_3CN$+0.05% Formic Acid over 3 min.

Detection: PDA 250-340 nm.

Flow rate: 1.5 ml/min

Preparation Intermediate 1

Benzotriazol-1-yl-benzyloxycarbonylamino-acetic acid

A mixture of glyoxylic acid monohydrate (4.60 g), benzotriazole (5.95 g) and benzyl carbamate (7.55 g) was heated to reflux in toluene (100 ml) for 18 h, under Dean-Stark conditions. The mixture was then allowed to cool to room temperature, and the resulting precipitate collected by filtration. This was then recrystallised from diethyl ether giving an off-white solid (11.66 g)

$^1$H NMR (d6 DMSO, δ) 5.07 (q+s, 3H), 7.25 (d, 1H), 7.3-7.63 (m, 6H), 7.92-8.10 (m, 2H), 9.32 (d, 1H).

LC/MS Found ES−=325 RT=4.68 min

Preparation Intermediate 2

(2-Oxo-5-phenyl-2,3-dihydro-1H-benzo[e][1,4]diazepin-3-yl)-carbamic acid benzyl ester A cold (0° C.) solution of Intermediate 1 (11.6 g) in dry THF (100 ml) under nitrogen was stirred, and was treated dropwise with a solution of oxalyl chloride (4.4 g) in dry dichloromethane (50 ml), followed by dry dimethylformamide (2 ml). This resulting mixture was stirred for 2 h, and was then treated with a solution of 2-(amino-phenyl)-phenyl-methanone (6.1 g) and N-methylmorpholine (7.07 g) in dry THF (50 ml) over 30 minutes. The reaction mixture was then allowed to warm to room temperature and was then filtered to remove inorganic salts. The mother liquors were then treated with 7M ammonia in methanol (100 ml) and stirring continued for 18 h. The solvents were then evaporated and the residue partitioned between ethyl acetate and 1M sodium hydroxide. The dried extracts were evaporated, and the crude oil dissolved in acetic acid (200 ml) containing ammonium acetate (13.4 g). This mixture was then stirred at room temperature for 18 h. The solvents were then evaporated and the residue was suspended in ethyl acetate:diethyl ether (1:3) (200 ml). 1M sodium hydroxide was added until pH8 was reached, and then the mixture was cooled to 0-5° C. and the resulting solid collected by filtration (6.94 g)

$^1$H NMR (d6 DMSO, δ) 5.05 (s, 1H), 5.09 (m, 2H), 7.25-7.69 (m, 14H), 8.38 (d, 1H), 10.85 (s, 1H).

LC/MS Found ES+=386 RT=5.46 min

Preparation Intermediate 3

3-Amino-5-phenyl-1,3-dihydro-benzo[e][1,4]diazepin-2-one

Intermediate 2 (1.07 g) was dissolved in 48% hydrobromic acid in acetic acid (30 ml) and was heated to 70° C. for 30 mins. The mixture was then allowed to cool, and was diluted with diethyl ether (30 ml). This led to the formation of a yellow solid which was collected by filtration. This material was then partitioned between ethyl acetate and 1M potassium carbonate solution. The extracts were dried, and then evaporated giving an oil which was triturated with diethyl ether giving an off-white solid (0.35 g)

$^1$H NMR (d6 DMSO, δ) 4.25 (s, 1H), 7.17-7.66 (m, 9H), 10.65 (brs, 1H).

LC/MS RT=3.23 min, but with no associated molecular ion.

Preparation Intermediate 4

[Benzotriazol-1-yl(2-benzoyl-4-chloro-phenylcarbamoyl)-methyl]-carbamic acid benzyl ester The acid chloride of Intermediate 1 was prepared as previously described from 5 g of Intermediate 1. This was added to a stirred solution of (2-amino-5-chloro-phenyl)-phenyl-methanone (3.48 g) and N-methylmorpholine (3.1 g) in THF (40 ml) at 0° C. After addition the mixture was allowed to warm to room temperature, and was stirred for 1 h. The precipitate was removed by filtration, and the solvent evaporated giving a gummy solid, which was used without purification or characterisation.

Preparation Intermediate 5

(7-Chloro-2-oxo-5-phenyl-2,3-dihydro-1H-benzo[e][1,4]diazepin-3-yl)-carbamic acid benzyl ester A solution of Intermediate 4 in 7M ammonia in methanol (100 ml) was stirred at room temperature for 5 h. The solvent was evaporated, and the residue partitioned between ethyl acetate, and 1M sodium hydroxide. The dried organic layer was evaporated, and the residue dissolved in acetic acid (200 ml) containing ammonium acetate (5.8 g). The resulting mixture was stirred at room temperature for 18 h, and then the solvent was evaporated. The residue was dissolved in water and ethyl acetate, and the pH was adjusted to ca. 8 with sodium hydroxide. The dried organic extracts were evaporated, and the residue triturated with diethyl ether giving a beige solid (3.27 g).

LC/MS Found ES+=420, 422 ($C_{23}H_{13}ClN_3O_3$=419.5)

Preparation Intermediate 6

3-Amino-7-chloro-5-phenyl-1,3-dihydro-benzo[e][1,4]diazepin-2-one

A solution of Intermediate 5 (3.25 g) in 45% hydrogen bromide in acetic acid (85 ml) was heated to 70° C. for 2 h. The mixture was then allowed to cool, and was diluted with diethyl ether. The hydrobromide salt of the title compound was obtained by filtration and dried, giving a bright yellow solid (2.7 g)

NMR ($\delta$, d6 DMSO) 5.18 (d, 1H), 7.32 (d, 1H), 7.40 (d, 1H), 7.47-7.53 (m, 5H), 7.77 (dd, 1H), 9.07 (brs, 2H), 11.41 (s, 1H).

Preparation Intermediate 7

[(2-Oxo-5-phenyl-2,3-dihydro-1H-benzo[e][1,4]diazepin-3-ylcarbamoyl)-phenyl-methyl]-carbamic acid tert-butyl ester.

A solution of Intermediate 3 (34.9 g), (S)-2-tert-Butoxycarbonylamino-3-phenyl-propionic acid (55.3 g), triethylamine (100 ml) and O-benzotriazol-1-yl-N,N,N',N'-tetramethyluronium hexafluorophosphate (116 g) in dichloromethane (1000 ml) was stirred at room temperature for 18 h. under nitrogen. The solvent was then evaporated and the residue partitioned between 10%. citric acid solution and ethyl acetate. The organic phase was further washed with 2M sodium hydroxide, water and brine before being dried (MgSO$_4$). The organic phase was evaporated giving an oil which was used crude in the following step.

LC/MS RT=5.98 min, Found ES+=498

$^1$H NMR (DMSO, $\delta$) 1.29 (s, 9H), 2.72-2.84 (m, 1H), 3.05-3.18 (m, 1H), 4.32-4.44 (m, 1H), 5.20-5.25 (m, 1H), 6.97-7.05 (m, 1H), 7.16-7.68 (m, 14H), 9.17-9.21 (d, 1H), 10.90 (s, 1H).

Preparation Intermediate 8

2-Amino-N-(2-oxo-5-phenyl-2,3-dihydro-1H-benzo[e][1,4]diazepin-3-yl)-2-phenyl-acetamide.

Intermediate 7 (81.94 g) was added in a single portion to a cooled (−10° C.) solution of HCl (34 g) in ethyl acetate (1 L). The reaction was stirred at this temperature for 1 hour, before being warmed to 20° C. and stirred for a further 2 hours. The reaction was then cooled to 0° C. and water (300 mL) added at a rate that maintained a temperature below 10° C. The aqueous layer was then washed with ethyl acetate (2×150 mL) and the aqueous layer returned to the reaction flask. The reaction was again cooled to 0° C. and concentrated aqueous ammonia added at a rate that maintained the temperature below 5° C. until pH 9.0 had been achieved. The reaction was then washed with ethyl acetate (5×150 mL) and the combined organic extracts washed with brine (100 mL), dried with magnesium sulphate and the solvent evaporated producing a yellow oil. The yellow oil was then stirred rapidly with a 5% solution of methanol in ethyl acetate until a thick white precipitate formed. The precipitate was filtered and the mother liquor again evaporated. The residual gum was again stirred with 5% methanol in ethyl acetate until a thick precipitate had formed. This sequence was repeated several times. On each occasion the precipitate was analysed to assess the diastereomeric excess by TLC (SiO$_2$, DCM:EtOH:NH$_3$, 200:8:1). Pure or mostly pure batches of each diastereomer were kept aside and mixtures returned to the precipitation procedure at the evaporation stage after first dissolving in a mixture of 5% methanol in dichloromethane. The combined batches that contained pure or mainly pure required diastereomer ($R_f$=0.25, higher spot) were stirred as a slurry in 5% methanol in ethyl acetate for 10 minutes and filtered to produce the required diastereomer (>99% d.e.), pure sample as a white powder (26.1 g).

LC/MS RT=3.83 min. Found ES+=399

$^1$H NMR (CDCl$_3$, $\delta$) 1.36 (bs, 2H), 2.72 (dd, 1H), 3.24 (dd, 1H), 3.63 (dd, 1H), 5.46 (d, 1H), 7.44-7.03 (m, 14H), 8.43 (s, 1H), 8.79 (d, 1H).

Preparation Intermediate 9

N-(2-Oxo-5-phenyl-2,3-dihydro-1H-benzo[e][1,4]diazepin-3-yl)-2-phenyl-2-(3-phenyl-thioureido)-acetamide A solution of Intermediate 8 (26.1 g) in dichloromethane (500 ml) was treated with isothiocyanato-benzene (14.7 g) and the mixture left to stir at room temperature for 18 h. The solvent and excess reagent was removed by evaporation and the residue redissolved in dichloromethane and then diluted with petrol giving a colourless solid which was collected by filtration (36.1 g).

LC/MS Found ES−=532 RT=5.47min $^1$H NMR (CDCl$_3$, $\delta$) 3.83-5.0 (m, 2H), 5.58-6.87 (m, 2H), 6.68 (d, 1H), 6.89-7.40 (m, 19H), 7.56 (d, 1H), 8.20 (bs, 1H), 9.52 (bs, 1H).

Preparation Intermediate 10

(S)-3-Amino-5-phenyl-1,3-dihydro-benzo[e][1,4]diazepin-2-one

Intermediate 9 (24 g) was heated to 50 C. and was then treated with trifluoroacetic acid (64 ml). The mixture was stirred rapidly for 40 mins and was then evaporated to dryness, giving a yellow oil. This material was purified by silica gel chromatography. Elution with dichloromethane:methanol:acetic acid:water, 90:10:1:1 gave the acetate salt of the amine as a pale yellow foam (13.1 g).

LC/MS RT=3.64 min Found ES+=252

$^1$H NMR (CDCl$_3$, $\delta$) 2.17 (s, 3H), 4.68 (brs, 1H), 6.98-7.47 (m, 9H), 9.56 (brs, 1H), 10.68 (brs, 1H).

The free base of this material may be isolated as follows. 0.5 g of this material was dissolved in dichloromethane (1 ml) and was basified by the addition of 0.880 ammonia (1 ml) giving a colourless precipitate which was collected by filtration and dried (380 mg).

Example 1

N-(2-Oxo-5-phenyl-2,3-dihydro-1H-benzo([e][1,4] diazepin-3-yl)-acetamide

A solution of Intermediate 3 (300 mg) in pyridine (5 ml) was treated with acetic anhydride (183 mg). The mixture was stirred at room temperature for 1.5 h and was then evaporated. The residue was partitioned between water and dichloromethane. The dried extract was evaporated and the residue triturated with petroleum ether giving a colourless solid (231 mg)

LC/MS RT=3.82 min Found ES-=292

NMR (δ, d6 DMSO) 1.99 (s, 3H), 5.25 (d, 1H), 7.21-7.66 (m, 9H), 9.06 (s, 1H), 10.81 (s, 1H).

Example 2

1,1-Diethyl-3-(2-oxo-5-phenyl-2,3-dihydro-1H-benzo[e][1,4]diazepin-3-yl)-urea

A solution of Intermediate 3 (100 mg) in dichloromethane: dimethylformamide (9:1; 2 ml) containing diisopropylethylamine (62 mg) was treated with diethylcarbamoyl chloride (0.05 ml). The resulting mixture was stirred under nitrogen at room temperature for 18 h, and was then partitioned between water and dichloromethane. The organic extract was evaporated and the residue was purified on a silica gel SPE cartridge. Elution with 10% methanol in ethyl acetate gave a colourless solid (34 mg).

LC/MS RT=4.37 min Found ES+=351

$^1$H NMR (d6 DMSO, δ) 1.11 (t, 6H), 2.50 (br, 4H), 5.20 (d, 1H), 6.83 (d, 1H), 7.20-7.66 (m, 9H), 10.78 (brs, 1H).

Example 3

N-(2-Oxo-5-phenyl-2,3-dihydro-1H-benzo[e][1,4] diazepin-3-yl)-propionamide

This material was prepared as described for Example 2 except that propionyl chloride (0.035 ml) was used. The title compound was a colourless solid (11 mg)

LC/MS RT=4.03 min Found ES+=308

$^1$H NMR (d6 DMSO, δ) 1.03 (t, 3H), 2.31 (q, 2H), 5.26 (d, 1H), 7.20-7.67 (m, 9H), 8.94 (d, 1H), 10.80 (s, 1H).

Example 4

N-(2-Oxo-5-phenyl-2,3-dihydro-1H-benzo[e][1,4] diazepin-3-yl)-butyramide

This material was prepared as described for Example 2 except that butyryl chloride (0.041 ml) was used. The title compound was a colourless solid (31 mg)

LC/MS RT=4.31 min Found ES+=320

$^1$H NMR (d6 DMSO, δ) 0.90 (brt, 3H), 1.55 (br, 2H), 2.27 (brq, 2H), 5.26 (brd, 1H), 7.20-7.70 (m, 9H), 8.95 (brd, 1H), 10.80 (s, 1H).

Example 5

N-2-Oxo-5-phenyl-2,3-dihydro-1H-benzo[e][1,4] diazepin-3-yl)-isobutyramide

This material was prepared as described for Example 2 except that isobutryl chloride (41 ml) was used. The title compound was a colourless solid (35 mg).

LC/MS RT=4.30 min Found ES+=322

$^1$H NMR (d6 DMSO, δ) 1.03 (d, 6H), 2.72 (septet, 1H), 5.23 (d, 1H), 7.20-7.68 (m, 9H), 8.90 (d, 1H), 10.77 (brs, 1H).

Example 6

2,2-Dimethyl-N-2-Oxo-5-phenyl-2,3-dihydro-1H-benzo[e][1,4]diazepin-3-yl)-propionamide This material was prepared as described for Example 2 except that 2,2-dimethylpropionyl chloride (0.049 ml) was used. The title compound was a colourless solid (22 mg)

LC/MS RT=4.74 min Found ES+=336

$^1$H NMR (d6 DMSO, δ) 1.20 (s, 9H), 5.23 (d, 1H), 7.20-7.68 (m, 9H), 8.22 (d, 1H), 10.80 (br, 1H).

Example 7

Cyclopentanecarboxylic acid (2-oxo-5-phenyl-2,3-dihydro-1H-benzo[e][1,4]diazepin-3-yl)-amide This material was prepared as described for Example 2 except that cyclopentanecarbonyl chloride (0.048 ml) was used. The title compound was a colourless solid (40 mg).

LC/MS RT=4.81 min Found ES+=348

$^1$H NMR (d6 DMSO, δ) 1.48-1.90 (m, 8H), 2.89 (m, 1H), 5.24 (d, 1H), 7.20-7.68 (m, 9H), 8.90 (d, 1H), 10.77 (brs, 1H).

Example 8

Cyclohexanecarboxylic acid 2-oxo-5-phenyl-2,3-dihydro-1H-benzo[e][1,4]diazepin-3-yl)-amide This material was prepared as described for Example 2 except that cyclohexanecarbonyl chloride (0.053 ml) was used. The title compound was a colourless solid (57 mg).

LC/MS RT=5.54 min Found ES+=362

$^1$H-NMR (d6 DMSO, δ) 1.10-1.43 (5H), 1.60-1.82 (m, 5H), 2.44 (m, 1H), 5.22 (d, 1H), 7.20-7.67 (m, 9H), 8.81 (d, 1H), 10.75 (s, 1H).

Example 9

3-Methoxy N-(2-oxo-5-phenyl-2,3-dihydro-1H-benzo[e][1,4]diazepin-3-yl)-benzamide This material was prepared as described for Example 1 except that 3-methoxy-benzoyl chloride (0.056 ml) was used. The title compound was a colourless solid (23 mg).

LC/MS RT=5.10 min Found ES+=386

$^1$H NMR (d6 DMSO, δ) 3.84 (s, 3H), 5.51 (d, 1H), 7.11-7.71 (m, 13H), 9.51 (d, 1H), 10.87 (s, 1H).

Example 10

4-Methoxy N-(2-oxo-5-phenyl-2,3-dihydro-1H-benzo[e][1,4]diazepin-3-yl)-benzamide

This material was prepared as described for Example 2 except that 4methoxy-benzoyl chloride (68 mg) was used. The title compound was a colourless solid (60 mg).

LC/MS RT=5.00min Found ES+=386

$^1$H NMR (d6 DMSO, δ) 3.83 (s, 3H), 5.50 (d, 1H), 7.02 (d, 2H), 7.21-7.79 (m, 9H), 8.02 (d, 2H), 9.28 (d, 1H), 10.85 (s, 1H).

Example 11

2-Methoxy N-(2-oxo-5-phenyl-2,3-dihydro-1H-benzo[e][1,4]diazepin-3-yl)-benzamide

This material was prepared as described for Example 2 except that 2-methoxy-benzoyl chloride (0.059 ml) was used. The title compound was a colourless solid (69 mg).

LC/MS RT=5.12 min Found ES+=386

$^1$H NMR (d6 DMSO, δ) 4.05 (s, 3H), 5.44 (d, 1H), 7.11 (t, 1H), 7.24-7.70 (m, 11H), 7.97 (dd, 1H), 9.50 (d, 1H), 10.97 (s, 1H).

Example 12

N-2-Oxo-5-phenyl-2,3-dihydro-1H-benzo[e][1,4]diazepin-3-yl)-3-trifluoromethyl-benzamide

This material was prepared as described for Example 2 except that 3-trifluoromethyl-benzoyl chloride (0.06 ml) was used. The title compound was a colourless solid (88 mg).

LC/MS RT=5.27 min Found ES+=424

$^1$H NMR (d6 DMSO, δ) 5.41 (d, 1H), 7.22-7.82 (m, 13H), 9.71 (d, 1H), 10.86 (brs, 1H).

Example 13

N-(2-Oxo-5-phenyl-2,3-dihydro-1H-benzo[e][1,4]diazepin-3-yl)-benzamide

This material was prepared as described for Example 2 except that benzoyl chloride (0.046 ml) was used. The title compound was a colourless solid (41 mg).

LC/MS RT=4.96 min Found ES+=356

$^1$H NMR (d6 DMSO, δ) 5.51 (d, 1H), 7.22-7.70 (m, 12H), 8.03 (m, 2H), 9.44 (d, 1H), 10.87 (s, 1H).

Example 14

Thiophene-2-carboxylic acid (2-oxo-5-phenyl-2,3-dihydro-1H-benzo[e][1,4]diazepin-3-yl)-3-amide

This material was prepared as described for Example 2 except that thiophene-2-carbonyl chloride (0.043 ml) was used. The title compound was a colourless solid (81 mg).

LC/MS RT=4.87 min Found ES+=362

$^1$H NMR (d6 DMSO, δ) 5.46 (d, 1H), 7.19-7.82 (m, 11H), 8.20 (m, 1H), 9.57 (d, 1H), 10.88 (s, 1H).

Example 15

Furan-2-carboxylic acid (2-oxo-5-phenyl-2,3-dihydro-1H-benzo[e][1,4]diazepin-3-yl)-amide

This material was prepared as described for Example 2 except that furan-2-carbonyl chloride (0.039 ml) was used. The title compound was a colourless solid (17 mg).

LC/MS RT=4.53 min Found ES+=346

$^1$H NMR (d6 DMSO, δ) 5.42 (d, 1H), 6.68 (m, 1H), 7.24-7.70 (m, 10H), 7.90 (m, 1H), 9.02 (d, 1H), 10.95 (s, 1H).

Example 16

Piperidine-1-carboxylic acid (2-oxo-5-phenyl-2,3-dihydro-1H-benzo[e][1,4]diazepin-3-yl)-amide

This material was prepared as described for Example 2 except that piperidine-1-carbonyl chloride (0.049 ml) was used. The title compound was a colourless solid (34 mg).

LC/MS RT=4.47 min Found ES+=363

$^1$H NMR (d6 DMSO, δ) 1.40-1.62 (m, 6H), 3.36-3.42 (m, 4H), 5.21 (d, 1H), 7.20-7.67 (m, 10H), 10.76 (s, 1H).

Example 17

Morpholine-4-carboxylic acid (2-oxo-5-phenyl-2,3-dihydro-1H-benzo[e][1,4]diazepin-3-yl)-amide

This material was prepared as described for Example 2 except that morpholine-4-carbonyl chloride (0.046 ml) was used. The title compound was a colourless solid (22 mg).

LC/MS RT=3.88 min Found ES+=365

$^1$H NMR (d6 DMSO, δ) 3.36-3.42 (m, 4H), 3.55-3.62 (m, 4H), 5.21 (d, 1H), 7.22-7.67 (m, 10H), 10.80 (s, 1H).

Example 18

4-Nitro-N-(2-oxo-5-phenyl-2,3-dihydro-1H-benzo[e][1,4]diazepin-3-yl)-benzamide

This material was prepared as described for Example 2 except that 4-nitro-benzoyl chloride (74 mg) was used. The title compound was a colourless solid (90 mg).

LC/MS RT=5.25 min Found ES+=401

$^1$H NMR (d6 DMSO, δ) 5.50 (d, 1H), 7.23-7.70 (m, 9H), 8.25 (d, 2H), 8.33 (d, 2H), 9.94 (d, 1H), 10.92 (s, 1H).

Example 19

3-Nitro-N-(2-oxo-5-phenyl-2,3-dihydro-1H-benzo[e][1,4]diazepin-3-yl)benzamide

This material was prepared as described for Example 2 except that 3-nitro-benzoyl chloride (74 mg) was used. The title compound was a colourless solid (94 g).

LC/MS RT=5.25 min Found ES+=401

$^1$H NMR (d6 DMSO, δ) 5.51 (d, 1H), 7.22-7.85 (m, 10H), 8.40-8.48 (m, 2H), 8.86 (m, 1H), 10.06 (d, 1H), 10.91 (s, 1H).

Example 20

4-Methyl-piperazine-1-carboxylic acid-(2-oxo-5-phenyl-2,3-dihydro-1H-benzo[e][1,4]diazepin-3-yl)-amide This material was prepared as described for Example 2 except that 4-methyl-1-piperazinecarbonyl chloride (79 mg) was used. The title compound was a colourless solid (35 mg).

LC/MS RT=3.29 min Found ES−=376

$^1$H NMR (d6 DMSO, δ) 2.19 (s, 3H), 2.28 (m, 4H), 3.40 (m, 4H), 5.19 (d, 1H), 7.19-7.65 (m, 10H), 10.75 (s, 1H).

Example 21

3,4-Dichloro-N-(2-oxo-5-phenyl-2,3-dihydro-1H-benzo[e][1,4]diazepin-3-yl)-benzamide This material was prepared as described for Example 2 except that 3,4-dichloro-benzoyl chloride (83 mg) was used. The title compound was a colourless solid (42 mg).

LC/MS RT=3.29 min Found ES+=424, 426

$^1$NMR (d6 DMSO, δ) 5.48 (d, 1H), 7.22-7.70 (m, 9H), 7.78 (d, 1H), 7.98 (dd, 1H), 8.31 (d, 1H), 9.82 (d, 1H), 10.91 (s, 1H).

Example 22

N-(2-oxo-5-phenyl-2,3-dihydro-1H-benzo[e][1,4]diazepin-3-yl)-2-trifluoromethyl-benzamide This material was prepared as described for Example 2 except that 2-trifluoromethyl-benzoyl chloride (83 mg) was used. The title compound was a colourless solid (90 mg).

LC/MS RT=5.47 min Found ES+=424

$^1$H NMR (d6 DMSO, δ) 5.41 (d, 1H), 7.25-7.83 (m, 13H), 9.81 (d, 1H), 10.93 (s, 1H).

Example 23

4-Bromo-N-2-oxo-5-phenyl-2,3-dihydro-1H-benzo[e][1,4]diazepin-3-yl)-benzamide

This material was prepared as described for Example 2 except that 4-bromo-benzoyl chloride (87 mg) was used. The title compound was a colourless solid (159 mg).

LC/MS RT=5.76 min Found ES+=434, 436

$^1$H NMR (d6 DMSO, δ) 5.5 (d, 1H), 7.23-7.68 (m, 9H), 7.72 (d, 2H), 7.98 (d, 2H), 9.7 (d, 1H), 10.94 (s, 1H).

Example 24

2-Methyl-N-(2-oxo-5-phenyl-2,3-dihydro-1H-benzo[e][1,4]diazepin-3-yl)-benzamide

This material was prepared as described for Example 2 except that 2-methyl-benzoyl chloride (62 mg) was used. The title compound was a colourless solid (113 mg).

LC/MS RT=5.29 min Found ES+=370

$^1$H NMR (d6 DMSO, δ) 2.42 (s, 3H), 5.45 (d, 1H), 7.23-7.55 (m, 12H), 7.65 (dt, 1H), 9.39 (d, 1H), 10.90 (s, 1H).

Example 25

2-Chloro-N-(2-oxo-5-phenyl-2,3-dihydro-1H-benzo[e][1,4]diazepin-3-yl)-benzamide

This material was prepared as described for Example 2 except that 2-chloro-benzoyl chloride (70 mg) was used. The title compound was a colourless solid (108 mg).

LC/MS RT=5.28 min Found ES+=390, 392

$^1$NMR (d6 DMSO, δ) 5.43 (d, 1H), 7.26-7.7 (m, 13H), 9.71 (d, 1H), 10.94 (s, 1H).

Example 26

2-Nitro-N-(2-oxo-5-phenyl-2,3-dihydro-1H-benzo[e][1,4]diazepin-3-yl)-benzamide

This material was prepared as described for Example 2 except that 2-nitro-benzoyl chloride (74 mg) was used. The title compound was a colourless solid (50 mg).

LC/MS RT=4.94 min Found ES+=401

$^1$NMR (d6 DMSO, δ) 5.42 (d, 1H), 7.25-7.89 (m, 12H), 8.07 (d, 1H), 10.05 (d, 1H), 10.96 (s, 1H).

Example 27a

2-Methoxy-4-nitro-N-(2-oxo-5-phenyl-2,3-dihydro-1H-benzo[e][1,4]diazepin-3-yl)-benzamide A mixture of Intermediate 3 (40 mg), 2-methoxy-4-nitro-benzoic acid (47 mg), triethylamine (0.07 ml) and O-benzotriazol-1-yl-N,N,N',N'-tetramethyluronium hexafluorophosphate (121 mg) in dry tetrahydrofuran (3 ml) was stirred at 20° C. for 18 h under a nitrogen atmosphere. The mixture was then partitioned between potassium carbonate solution and dichloromethane. The organic phase was passed through a hydrophobic frit and evaporated. The residue was purified on a silica gel SPE cartridge. Elution with dichloromethane, then with dichloromethane:ethanol:0.880 ammonia; 400 then 200:8:1 gave an oil which was triturated with diethyl ether giving the title compound as a colourless solid (51 mg).

LC/MS RT=5.28 min Found ES+=431

$^1$H NMR (CDCl$_3$, δ) 4.09 (s, 3H), 5.69 (d, 1H), 7.08-7.49 (m, 9H), 7.80-7.86 (m, 2H), 8.27 (s, 1H), 8.31 (s, 1H), 9.52 (d, 1H).

Example 27b (S)-2-Methoxy-4-nitro-N-(2-oxo-5-phenyl-2,3-dihydro-1H-benzo[e][1,4]diazepin-3-yl)-benzamide This material was prepared as described for Example 27 except that Intermediate 10 was used in place of Intermediate 3. The title compound was obtained as a colourless solid (37 mg).

$^1$H NMR (DMSO, δ) 4.13 (s, 3H), 5.44 (d, 1H), 7.29-7.70 (m, 9H), 7.97-8.10 (m, 3H), 9.63 (d, 1H), 11.05 (s, 1H).

Example 28

Benzo[b]thiophene-3-carboxylic acid (2oxo-5-phenyl-2,3-dihydro-1H-benzo[e][1,4]diazepin-3-yl)-amide This material was prepared as described for Example 2 except that benzo[b]thiopehene-3-carbonyl chloride (39 mg) was used. The title compound was a colourless solid (60 mg).

LC/MS RT=5.85 min Found ES+=412
$^1$H NMR (d6 DMSO, δ) 5.57 (d, 1H), 7.27-7.71 (m, 11H), 8.06 (m, 1H), 8.47 (m, 1H), 8.83 (s, 1H), 9.57 (d, 1H), 10.95 (s, 1H).

Example 29

2,3-Dihydro-benzofuran-5-carboxylic acid (2-oxo-5-phenyl-2,3-dihydro-1H-benzo[e][1,4]diazepin-3-yl)-amide This material was prepared as described for Example 2 except that 2,3-dihydro-benzofuran-5-carbonyl chloride (36 mg) was used. The title compound was a colourless solid (75 mg).
LC/MS RT=5.16 min Found ES+=398
$^1$H NMR (d6 DMSO, δ) 3.24 (t, 2H), 4.61 (t, 2H), 5.48 (d, 1H), 6.84 (d, 1H), 7.22-7.95 (m, 11H), 9.25 (d, 1H), 10.89 (s, 1H).

Example 30

Isoxazole-5-carboxylic acid (2-oxo-5-phenyl-2,3-dihydro-1H-benzo[e][1,4]diazepin-3-yl)-amide This material was prepared as described for Example 2 except that isoxazole-5-carbonyl chloride (26 mg) was used. The title compound was a colourless solid (22 mg).
LC/MS RT=4.58 min Found ES+=347
$^1$H NMR (d6 DMSO, δ) 5.47 (d, 1H), 7.23-7.72 (m, 10H), 8.80 (d, 1H), 9.98 (d, 1H), 11.03 (s, 1H).

Example 31

Benzo[b]thiophene-2-carboxylic acid (2-oxo-5-phenyl-2,3-dihydro-1H-benzo[e][1,4]diazepin-3-yl)-amide This material was prepared as described for Example 2 except that benzo[b]thiophene-2-carbonyl chloride (39 mg) was used. The title compound was a colourless solid (33 mg).
LC/MS RT=5.90 min Found ES+=412
$^1$H NMR (d6 DMSO, δ) 5.49 (d, 1H), 7.25-7.72 (m, 11H), 7.95-8.07 (m, 2H), 8.56 (s, 1H), 9.92 (d, 1H), 10.96 (s, 1H).

Example 32

Thiophen-3-carboxylic acid (2-oxo-5-phenyl-2,3-dihydro-1H-benzo[e][1,4]diazepin-3-yl)-amide This material was prepared as described for Example 2 except that thiophene-3-carbonyl chloride (29 mg) was used. The title compound was a colourless solid (30 mg).
LC/MS RT=4.96 min Found ES+=362
$^1$H NMR (d6 DMSO, δ) 5.47 (d, 1H), 7.23-7.70 (m, 11H), 8.48 (m,1H), 9.40 (d, 1H), 10.91 (s, 1H).

Example 33

N-(2-Oxo-5-phenyl-2,3-dihydro-1H-benzo[e][1,4]diazepin-3-yl)-isonicotinamide

This material was prepared as described for Example 2 except that isonicotinoyl chloride, hydrochloride (71 mg) was used as well as an extra equivalent of triethylamine. The title compound was a colourless solid (22 mg).
LC/MS RT=3.98 min Found ES+=357
$^1$H NMR (d6 DMSO, δ) 5.50 (d, 1H), 7.24-7.70 (m, 9H), 7.93 (d, 2H), 8.76 (d, 2H), 9.89 (d, 1H), 10.91 (s, 1H).

Example 34

N-(2-Oxo-5-phenyl-2,3-dihydro-1H-benzo[e][1,4]diazepin-3-yl)-nicotinamide

This material was prepared as described for Example 2 except that nicotinoyl chloride, hydrochloride was used as well as an extra equivalent of triethylamine. The title compound was a colourless solid (16 mg).
LC/MS RT=3.90 min Found ES+=357
$^1$H NMR (d6 DMSO, δ) 5.51 (d, 1H), 7.23-7.70 (m, 10H), 8.37 (ddd, 1H), 8.75 (dd, 1H), 9.15 (d, 1H), 9.90 (d, 1H), 10.93 (s, 1H).

Example 35

N-(2-Oxo-5-phenyl-2,3-dihydro-1H-benzo[e][1,4]diazepin-3-yl)-methanesulfonamide

This material was prepared as described for Example 2 except that methanesulfonyl chloride (0.03 ml) was used. The title compound was a colourless solid (40 mg).
LC/MS RT=4.20 min Found ES+=330
$^1$H NMR (d6 DMSO, δ) 3.13 (s, 3H), 4.81 (brd, 1H), 7.22-7.70 (m, 9H), 8.43 (brd, 1H), 10.95 (brs, 1H).

Example 36

Propane-1-sulfonic acid-(2-oxo-5-phenyl-2,3-dihydro-1H-benzo[e][1,4]diazepin-3-yl)-amide This material was prepared as described for Example 2 except that propane-1-sulfonyl chloride (0.054 ml) was used. The title compound was a colourless solid (56 mg).
LC/MS RT=4.79 min Found ES+=358
$^1$H NMR (d6 DMSO, δ) 1.03 (t, 3H), 1.84 (m, 2H), 3.14 (t, 2H), 4.79 (d, 1H), 7.23-7.69 (m, 9H), 8.49 (d, 1H), 10.94 (s, 1H).

Example 37

Butane-1-sulfonic acid-(2-oxo-5-phenyl-2,3-dihydro-1H-benzo[e][1,4]diazepin-3-yl)-amide This material was prepared as described for Example 2 except that butane-1-sulfonyl chloride (0.062 ml) was used. The title compound was a colourless solid (30 mg).
LC/MS RT=5.18 min Found ES+=372
$^1$H NMR (d6 DMSO, δ) 0.93 (t, 3H), 1.44 (m, 2H), 1.80 (m, 2H), 3.14 (t, 2H), 4.78 (brd, 1H), 7.21-7.68 (m, 9H), 8.47 (brd, 1H), 10.94 (brs, 1H).

Example 38

2-Bromo-N-(2-oxo-5-phenyl-2,3-dihydro-1H-benzo[e][1,4]diazepin-3-yl)-benzenesulfonamide This material was prepared as described for Example 2 except that 2-bromo-benzenesulfonyl chloride (122 mg) was used. The title compound was a colourless solid (137 mg).

LC/MS RT=5.53 min Found ES+=470, 472

$^1$H NMR (d6 DMSO, δ) 4.95 (s, 1H), 7.03-7.71 (m, 12H), 7.88 (m, 1H), 8.22 (m, 1H), 8.70 (br, 1H), 11.04 (s, 1H).

Example 39

3-Bromo-N-(2-oxo-5-phenyl-2,3-dihydro-1H-benzo[e][1,4]diazepin-3-yl)-benzenesulfonamide This material was prepared as described for Example 2 except that 3-bromo-benzenesulfonyl chloride (122 mg) was used. The title compound was a colourless solid (90 mg).

LC/MS RT=5.63 min Found ES+=470, 472

$^1$H NMR (d6 DMSO, δ) 4.81 (s, 1H), 6.89 (m, 2H), 7.20-7.70 (m, 9H), 7.82 (m, 1H), 7.94 (m, 1H), 9.3 (br, 1H), 10.97 (s, 1H).

Example 40

4-Bromo-N-(2-oxo-5-phenyl-2,3-dihydro-1H-benzo[e][1,4]diazepin-3-yl)-benzenesulfonamide This material was prepared as described for Example 2 except that 4-bromo-benzenesulfonyl chloride (122 mg) was used. The title compound was a colourless solid (130 mg).

LC/MS RT=5.66 min Found ES+=470, 472

$^1$H NMR (d6 DMSO, δ) 4.80 (brd, 1H), 6.75 (m, 2H), 7.20-7.70 (m, 7H), 7.78-7.91 (m, 4H), 9.40 (brd, 1H), 10.95 (s, 1H).

Example 41

2-Fluoro-N-(2-oxo-5-phenyl-2,3-dihydro-1H-benzo[e][1,4]diazepin-3-yl)-benzenesulfonamide This material was prepared as described for Example 1 except that 2-fluoro-benzenesulfonyl chloride (93 mg) was used. The title compound was a colourless solid (140 mg).

LC/MS RT=5.26 min Found ES+=410

$^1$H NMR (d6 DMSO, δ) 4.94 (d, 1H), 7.07 (m, 2H), 7.23-7.97 (m,11H), 9.36 (d, 1H), 10.97 (s, 1H).

Example 42

3-2-Nitro-benzylamino)-5-phenyl-1,3-dihydro-benzo[e][1,4]diazepin-2-one

A solution of Intermediate 3 (50 mg) and sodium (triacetoxy)borohydride (106 mg) in dichloromethane (6 ml) and acetic acid (1 ml) was treated with 2-nitro-benzaldehyde (45 mg). The resulting mixture was stirred under nitrogen for 18 h. Saturated sodium bicarbonate solution was carefully added, and the mixture extracted with dichloromethane. The organic layer was passed through a hydrophobic frit, and evaporated. The residue was then purified on a silica gel SPE cartridge. Gradient elution with 10-18% ethyl acetate in petrol gave the title compound as a colourless solid (33 mg).

LC/MS RT=4.83 min Found ES+=387

$^1$H NMR (d6 DMSO, δ) 3.4 (br, 1H), 4.17 (brs, 1H), 4.31 (q, 2H), 7.15-7.95 (m, 13H), 10.74 (s, 1H).

Example 43

3-3-Nitro-benzylamino)-5-phenyl-1,3-dihydro-benzo[e][1,4]diazepin-2-one

This material was prepared as described for Example 42 except that 3-nitro-benzaldehyde (45 mg) was used. The title compound was a colourless solid (32 mg).

LC/MS RT=4.95 min Found ES+=387

$^1$H NMR (d6 DMSO, δ) 3.45 (br, 1H), 4.16 (brs, 1H), 4.23 (brm, 2H), 7.15-7.63 (m, 10H), 7.85 (d, 1H), 8.08 (dd, 1H), 8.30 (s, 1H), 10.76 (s, 1H).

Example 44

3-4-Nitro-benzylamino)-5-phenyl-1,3-dihydro-benzo[e][1,4]diazepin-2-one

This material was prepared as described for Example 42 except that 4nitro-benzaldehyde (45 mg) was used. The title compound was a colourless solid (33 mg).

LC/MS RT=4.88 min Found ES+=387

$^1$H NMR (d6 DMSO, δ) 3.42 (br, 1H), 4.11-4.30 (brm, 3H), 7.16-7.63 (m, 9H), 7.70 (d, 2H), 8.20 (d, 2H), 10.77 (s, 1H).

Example 45

3-(2-Methoxy-benzylamino)-5-phenyl-1,3-dihydro-benzo[e][1,4]diazepin-2-one

This material was prepared as described for Example 42 except that 2-methoxy-benzaldehyde (41 mg) was used. The title compound was a colourless solid (48 mg).

LC/MS RT=4.95 min Found ES+=372

$^1$H NMR (d6 DMSO, δ) 3.73 (s, 3H), 3.97 (q, 2H), 4.17 (s, 1H), 6.85-6.96 (m, 2H), 7.15-7.63 (m, 11H), 10.72 (s, 1H).

Example 46

3-(3-Methoxy-benzylamino)-5-phenyl-1,3-dihydro-benzo[e][1,4]diazepin-2-one

This material was prepared as described for Example 42 except that 3-methoxy-benzaldehyde (41 mg) was used. The title compound was a colourless solid (43 g).

LC/MS RT=5.03 min Found ES+=372

$^1$H NMR (d6 DMSO, δ) 3.71 (s, 3H), 3.81-4.18 (m, 3H), 6.74 (m, 1H), 6.80-6.86 (m, 2H), 7.15-7.64 (m, 10H), 10.74 (s, 1H).

Example 47

5-Phenyl-3-(2-trifluoromethyl-benzylamino-1,3-dihydro-benzo[e][1,4]diazepin-2-one This material was prepared as described for Example 42 except that 2-trifluoromethyl-benzaldehyde (52 mg) was used. The title compound was a colourless solid (29 mg).

LC/MS RT=5.02 min Found ES+=410

$^1$H NMR (d6 DMSO, δ) 4.18 (s, 1H), 4.23 (brs, 2H), 7.15-7.70 (m, 12H), 7.91 (d, 1H), 10.76 (s, 1H).

Example 48

5-Phenyl-3-(3-trifluoromethyl-benzylamino)-1,3-dihydro-benzo[e][1,4]diazepin-2-one This material was prepared as described for Example 42 except that 3-trifluoromethyl-benzaldehyde (52 mg) was used. The title compound was a colourless solid (34 mg).
LC/MS RT=5.28 min Found ES−=408
$^1$H NMR (d6 DMSO, δ) 4.12 (q, 2H), 4.18 (s, 1H), 7.15-7.78 (m, 13H), 10.74 (s, 1H).

Example 49

5-Phenyl-3-(4-trifluoromethyl-benzylamino)-1,3-dihydro-benzo[e][1,4]diazepin-2-one This material was prepared as described for Example 42 except that 4-trifluoromethyl-benzaldehyde (52 mg) was used. The title compound was a colourless solid (25 mg).
LC/MS RT=5.27 min Found ES−=408
$^1$H NMR (d6 DMSO, δ) 4.13 (q, 2H), 4.20 (s, 1H), 7.15-7.70 (m, 13H), 10.76 (s, 1H).

Example 50

3-[(Furan-2-ylmethyl)-amino]-5-phenyl-1,3-dihydro-benzo[e][1,4]diazepin-2-one

This material was prepared as described for Example 42 except that 2-furaldehyde (29 mg) was used. The title compound was a colourless solid (56 mg).
LC/MS RT=4.07 min Found ES+=332
$^1$H NMR (d6 DMSO, δ) 3.05 (m, 1H), 3.80-4.13 (m, 2H), 4.18 (d, 1H), 6.19 (brs, 1H), 6.32 (brs, 1H), 7.15-7.65 (m, 10H).

Example 51

N-(7-Chloro-2-oxo-5-phenyl-2,3-dihydro-1H-benzo[e][1,4]diazepin-3-yl)-acetamide

This material was prepared as described for Example 1 except that Intermediate 6 (57 mg) was used. The title compound was a colourless solid (17 mg).
LC/MS RT=4.21 min Found ES+=328, 330
$^1$H NMR (d6 DMSO, δ) 3.34 (s, 3H), 5.26 (d, 1H), 7.28-7.31 (m, 2H), 7.31-7.58 (m, 5H), 7.71 (dd, 1H), 9.14 (d, 1H), 10.96 (s, 1H).

Example 52

N-(7-Chloro-2-oxo-5-phenyl-2,3-dihydro-1H-benzo[e][1,4]diazepin-3-yl)-isobutyramide This material was prepared as described for Example 2 except that Intermediate 6 and isobutyl chloride (0.021 ml) was used. The title compound was a colourless solid (49 mg).
LC/MS RT=4.78 min Found ES+=356, 358
$^1$H NMR (d6 DMSO, δ) 1.04 (d, 6H), 2.72 (septet, 1H), 5.27 (d, 1H), 7.29-7.55 (m, 7H), 7.71 (dd, 1H), 9.00 (d, 1H), 10.92 (s, 1H).

Example 53

N-(7-Chloro-2-oxo-5-phenyl-2,3-dihydro-1H-benzo[e][1,4]diazepin-3-yl)-methanesulfonamide This material was prepared as described for Example 2 except that Intermediate 6 and methanesulfonyl chloride (0.015 ml) were used. The title compound was a colourless solid (18 mg).
LC/MS RT=4.61 min Found ES+=364, 366
$^1$H NMR (d6 DMSO, δ) 3.13 (s, 3H), 4.85 (brd, 1H), 7.29-7.58 (m, 7H), 7.71 (dd, 1H), 8.46 (brd, 1H), 11.04 (brs, 1H).

Example 54

Furan-2-carboxylic acid (7-chloro-2-oxo-5-phenyl-2,3-dihydro-1H-benzo[e][1,4]diazepin-3-yl)-amide This material was prepared as described for Example 2 except that Intermediate 6 and 2-furancarbonyl chloride (0.020 ml) were used. The title compound was a colourless solid (50 mg).
LC/MS RT=5.07 min Found ES+=380, 382
$^1$H NMR (d6 DMSO, δ) 5.45 (d, 1H), 6.68 (m, 1H), 7.28-7.70 (m, 7H), 7.73 (dd, 1H), 7.91 (m, 1H), 9.15 (d, 1H), 11.07 (s, 1H).

Example 55

Thiophene-2-carboxylic acid (7-chloro-2-oxo-5-phenyl-2,3-dihydro-1H-benzo[e][1,4]diazepin-3-yl)-amide This material was prepared as described for Example 2 except that Intermediate 6 and 2-thiophenecarbonyl chloride (0.021 ml) were used. The title compound was a colourless solid (49 mg).
LC/MS RT=5.40 min Found ES+=396, 398
$^1$H NMR (d6 DMSO, δ) 5.49 (d, 1H), 7.22-7.83 (m, 10H), 8.21 (dd, 1H), 9.67 (d, 1H), 11.04 (s, 1H).

Example 56

Cyclohexanecarboxylic acid (7-Chloro-2-oxo-5-phenyl-2,3-dihydro-1H-benzo[e][1,4]diazepin-3-yl)-amide This material was prepared as described for Example 2 except that Intermediate 6 and cyclohexanecarbonyl chloride (0.027) were used. The title compound was a colourless solid (52 mg).
LC/MS RT=5.61 min Found ES+=396, 398
$^1$H NMR (d6 DMSO, δ) 1.2-1.33 (m, 5H), 1.60-1.83 (m, 5H), 2.45 (m, 1H), 5.25 (d, 1H), 7.27-7.73 (m, 8H), 8.93 (d, 1H), 10.92 (s, 1H).

Example 57

N-(7-Chloro-2-oxo-5-phenyl-2,3-dihydro-1H-benzo[e][1,4]diazepin-3-yl)-2-methoxy-benzamide This material was prepared as described for Example 2 except that Intermediate 6 and 2-methoxy-benzoyl chloride (0.030 ml) were used. The title compound was a colourless solid (55 mg).

LC/MS RT=5.58 min Found ES+=420, 422
¹H NMR (d6 DMSO, δ) 4.05 (s, 3H), 5.47 (d, 1H), 7.12 (t, 1H), 7.25-7.61 (m, 9H), 7.72 (dd, 1H), 7.98 (dd, 1H), 9.54 (d, 1H), 11.14 (s, 1H).

Example 58

N-(7-Chloro-2-oxo-5-phenyl-2,3-dihydro-1H-benzo[e][1,4]diazepin-3-yl)4-methoxy-benzamide This material was prepared as described for Example 2 except that Intermediate 6 and 4-methoxy-benzoyl chloride (0.027 ml) were used. The title compound was a colourless solid (61 mg).
LC/MS RT=5.48 min Found ES+=420, 422
¹H NMR (d6 DMSO, δ) 3.84 (s, 3H), 5.53 (d, 1H), 7.03 (d, 2H), 7.31-7.59 (m, 8H), 8.04 (d, 2H), 9.39 (d, 1H), 11.01 (s, 1H).

Example 59

N-(7-Chloro-2-oxo-5-phenyl-2,3-dihydro-1H-benzo[e][1,4]diazepin-3-yl)-2-nitro-benzamide This material was prepared as described for Example 2 except that Intermediate 6 and 2-nitro-benzoyl chloride (0.027) were used. The title compound was a colourless solid (61 mg).
LC/MS RT=5.25 min Found ES+=435, 437
¹H NMR (d6 DMSO, δ) 5.45 (d, 1H), 7.36-7.88 (m, 11H), 8.07 (*d, 1H), 10.03 (d, 1H), 11.03 (s, 1H).

Example 60

2-2-Methoxy-phenyl)-N-2-oxo-5-phenyl-2,3-dihydro-1H-benzo[e][1,4]diazepin-3-yl)-acetamide This material was prepared as described for Example 2 except that (2-methoxy-phenyl)-acetyl chloride (33 mg) was used. The title compound was a colourless solid (13 mg).
LC/MS RT=4.98 min Found ES+=400
¹H NMR (d6 DMSO, δ) 3.63 (s, 2H), 3.79 (s, 3H), 5.25 (d, 1H), 6.89-6.99 (m, 2H), 7.20-7.33 (m, 5H), 7.45-7.68 (m, 6H), 9.01 (d, 1H), 10.87 (s, 1H).

Example 61

2-3-Methoxy-phenyl)-N-2-oxo-5-phenyl-2,3-dihydro-1H-benzo[e][1,4]diazepin-3-yl)-acetamide This material was prepared as described for Example 2 except that (3-methoxy-phenyl)-acetyl chloride (33 mg) was used. The title compound was a colourless solid (12 mg).
LC/MS RT=4.95 min Found ES+=400
¹H NMR (d6 DMSO, δ) 3.62 (m, 2H), 3.75 (s, 3H), 5.23 (d, 1H), 6.78-6.96 (m, 3H), 7.19-7.70 (m, 10H), 9.33 (d, 1H), 10.86 (s, 1H).

Example 62

2-(4-Methoxy-phenyl)-N-(2-oxo-5-phenyl-2,3-dihydro-1H-benzo[e][1,4]diazepin-3-yl)-acetamide This material was prepared as described for Example 2 except that (4-methoxy-phenyl)-acetyl chloride (33 mg) was used. The title compound was a colourless solid (20 mg).
LC/MS RT=4.86 min Found ES+=400
¹H NMR (d6 DMSO, δ) 3.58 (s, 2H), 3.73 (s, 3H), 5.22 (d, 1H), 6.87 (d, 2H), 7.23-7.71 (m, 11H), 9.25 (d, 1H), 10.85 (s, 1H).

Example 63

2-(4-Nitro-phenyl)-N-(2-oxo-5-phenyl-2,3-dihydro-1H-benzo[e][1,4]diazepin-3-yl)-acetamide This material was prepared as described for Example 2 except that (4nitro-phenyl)-acetyl chloride (36 mg) was used. The title compound was a colourless solid (18 mg).
LC/MS RT=5.03 min Found ES+=415
¹H NMR (d6 DMSO, δ) 3.86 (s, 2H), 5.24 (d, 1H), 7.24-7.70 (m, 11H), 8.19 (d, 2H), 9.53 (d, 1H), 10.88 (s, 1H).

Example 64

2-(3-Nitro-phenyl)-N-(2-oxo-5-phenyl-2,3-dihydro-1H-benzo[e][1,4]diazepin-3-yl)-acetamide This material was prepared as described for Example 2 except that (3-nitro-phenyl)-acetyl chloride (36 mg) was used. The title compound was a colourless solid (25 mg).
LC/MS RT=5.02 min Found ES+=415
¹H NMR (d6 DMSO, δ) 3.86 (s, 2H), 5.24 (d, 1H), 7.24-7.67 (m, 10H), 7.89 (d, 1H), 8.12 (dd, 1H), 8.26 (s, 1H), 9.53 (d, 1H), 10.89 (s, 1H).

Example 65

N-(2-Oxo-5-phenyl-2,3-dihydro-1H-benzo[e][1,4]diazepin-3-yl)-2-2-trifluoromethyl-phenyl)-acetamide This material was prepared as described for Example 2 except that (2-trifluoromethyl-phenyl)-acetyl chloride (41 mg) was used. The title compound was a colourless solid (9 mg).
LC/MS RT=5.43 min Found ES+=438
¹H NMR (d6 DMSO, δ) 3.92 (s, 2H), 5.26 (d, 1H), 7.24-7.70 (m, 13H), 9.41 (d, 1H), 10.87 (s, 1H).

Example 66

N-(2-Oxo-5-phenyl-2,3-dihydro-1H-benzo[e][1,4]diazepin-3-yl)-2-(3-trifluoromethyl-phenyl)-acetamide This material was prepared as described for Example 2 except that 3-trifluoromethyl-phenyl)-acetyl chloride (41 mg) was used. The title compound was a colourless solid (20 mg).
LC/MS RT=5.56 min Found ES+=438
¹H NM (d6 DMSO, δ) 3.80 (s, 2H), 5.24 (d, 1H), 7.24-7.75 (m, 13H), 9.49 (d, 1H), 10.89 (s, 1H).

Example 67

N-(2-Oxo-5-phenyl-2,3-dihydro-1H-benzo[e][1,4]diazepin-3-yl)-2-4-trifluoromethyl-phenyl)-acetamide This material was prepared as described for Example 2 except that (4-trifluoromethyl-phenyl)-acetyl chloride (41 mg) was used. The title compound was a colourless solid (13 mg).

LC/MS RT=5.57 min Found ES+=438
¹H NMR (d6 DMSO, δ) 3.79 (s, 2H), 5.23 (d, 1H), 7.24-7.70 (m, 13H), 9.48 (d, 1H), 10.87 (s, 1H).

Example 68

1-(2-Methoxy-phenyl)-3-(2-oxo-5-phenyl-2,3-dihydro-1H-benzo[e][1,4]diazepin-3-yl)-urea A solution of 2-methoxy-aniline (37 mg) in dry dichloromethane (3 ml) was treated with triethylamine (0.04 ml) followed by 20% phosgene in toluene (0.08 ml). The mixture was stirred at room temperature for 1 h, and then Intermediate 3 (37 mg) was then added, and the stirring continued for 18 h. The mixture was partitioned between water and ethyl acetate. The organic layer was passed through a hydrophobic frit and evaporated and the residue was purified on a silica gel SPE cartridge. Gradient elution with 0-5% methanol in dichloromethane gave the title compound as a colourless solid (24 mg).
LC/MS RT=5.05 min Found ES+=401
¹H NMR (d6 DMSO, δ) 3.86 (s, 3H), 5.21 (d, 1H), 6.78-7.02 (m, 3H), 7.23-7.70 (m, 9H), 7.98 (m 1H), 8.26 (d, 1H), 8.60 (s, 1H), 10.89 (s, 1H).

Example 69

1-(2-Nitro-phenyl)-3-(2-oxo-5-phenyl-2,3dihydro-1H-benzo[e][1,4]diazepin-3-yl)-urea This material was prepared as described for Example 68 except that 2-nitro-aniline (21 mg) was used. The title compound was a yellow solid (23 mg).
LC/MS RT=5.30 min Found ES+=416
¹H NMR (d6 DMSO, δ) 5.19 (d, 1H), 7.15-7.70 (m, 11H), 8.05 (dd, 1H), 8.17 (d, 1H), 8.82 (d, 1H), 9.68 (s, 1H), 10.95 (s, 1H).

Example 70

1-(2-Chloro-phenyl)-3-(2-oxo-5-phenyl-2,3dihydro-1H-benzo[e][1,4]diazepin-3-yl)-urea This material was prepared as described for Example 68 except that 2-chloro-aniline (0.017 ml) was used. The title compound was a colourless solid (21 mg).
LC/MS RT=5.34 min Found ES+=405
¹H NMR (d6 DMSO, δ) 5.21 (d, 1H), 6.94-7.70 (m, 12H), 8.08 (m, 1H), 8.47 (d, 1H), 8.57 (s, 1H), 10.93 (s, 1H).

Example 71

1-(4-Chloro-phenyl)-3-(2-oxo-5-phenyl-2,3-dihydro-1H-benzo[e][1,4]diazepin-3-yl)-urea A mixture of Intermediate 3 (30 mg) and 4-chloro-1-isocyanato-benzene (0.01 ml) in dry THF (4 ml) was treated with triethylamine (0.05 ml). The mixture was stirred at room temperature for 18 h, and was then partitioned between water and dichloromethane. The organic layer was passed through a hydrophobic frit, and was then evaporated. The residue was triturated with petroleum ether giving the title compound as a beige solid (34 mg).
LC/MS RT=5.45 min Found ES+=405
¹H NMR (d6 DMSO, δ) 5.17 (d, 1H), 7.25-7.70 (m, 14H), 9.18 (s, 1H), 10.95 (s, 1H).

Example 72

1-(2-oxo-5-phenyl-2,3-dihydro-1H-benzo[e][1,4]diazepin-3-yl)-3-p-tolyl-urea

This material was prepared as described for Example 71 except that 1-isocyanato-4 methyl-benzene (0.011 ml) was used. The title compound was an off-white solid (32 mg).
LC/MS RT=5.18 min Found ES+=385
¹H NMR (d6 DMSO, δ) 2.22 (s, 3H), 5.19 (d, 1H), 7.05 (d, 2H), 7.23-7.70 (m, 12H), 8.92 (s, 1H), 10.92 (s, 1H).

Example 73a 1-(2-Fluoro-phenyl)-3-(2-oxo-5-phenyl-2,3-dihydro-1H-benzo[e][1,4]diazepin-3-yl)-urea This material was prepared as described for Example 71 except that 2-fluoro-1-isocyanato-benzene (0.010 ml) was used. The title compound was a beige solid (29 mg).
LC/MS RT=5.09 min Found ES+=389
¹H NMR (d6 DMSO, δ) 5.21 (d, 1H), 6.90-7.70 (m, 12H), 8.07 (m, 2H), 8.93 (s, 1H), 10.94 (s, 1H).

Example 73b (S)-1-(2-Fluoro-phenyl)-3-(2-oxo-5-phenyl-2,3-dihydro-1H-benzo[e][1,4]diazepin-3-yl)-urea This material was prepared as described for Example 73 except that Intermediate 10 was used. The title compound was a colourless solid (33 mg).
¹H NMR (DMSO, δ) 5.24 (d, 1H), 6.90-7.75 (m, 12H), 8.11-8.17 (m, 2H), 8.95 (d, 1H), 10.95 (s, 1H).

Example 74

1-(4-Fluoro-phenyl)-3-(2-oxo-5-phenyl-2,3dihydro-1H-benzo[e][1,4]diazepin-3-yl)-urea This material was prepared as described for Example 71 except that 4-fluoro-1-isocyanato-benzene (0.010 ml) was used. The title compound was an off-white solid (26 mg).
LC/MS RT=5.02 min Found ES+=389
¹H NMR (d6 DMSO, δ) 5.18 (d, 1H), 7.08 (t, 2H), 7.25-7.70 (m, 12H), 9.07 (s, 1H), 10.94 (s, 1H).

Example 75a

4-Methanesulfonyl-2-methoxy-N-(2-oxo-5-phenyl-2,3-dihydro-1H-benzo[e][1,4]diazepin-3-yl)-benzamide This material was prepared as described for Example 27 except that 4-methanesulfonyl-2-methoxy-benzoic acid (69 mg) was used. The title compound was a colourless solid (54 mg).
¹H NMR (DMSO, δ) 3.33 (s, 3H), 4.13 (s, 3H), 5.44 (d, 1H), 7.33-7.71 (m, 11H), 8.10 (d, 1H), 9.61 (d, 1H), 11.06 (s, 1H).

Example 75b (S)-4-Methanesulfonyl-2-methoxy-N-(2-oxo-5-phenyl-2,3-dihydro-1H-benzo[e][1,4]diazepin-3-yl)-benzamide This material was prepared as described for Example 76b except that 4-methanesulfonyl-2-methoxy-benzoic acid (46 mg) was used. The title compound was a colourless solid (55 mg).
$^1$H NMR (DMSO, δ) 3.33 (s, 3H), 4.13 (s, 3H), 5.44 (d, 1H), 7.33-7.71 (m, 11H), 8.10 (d, 1H), 9.61 (d, 1H), 11.06 (s, 1H).

Example 76a

5-Acetyl-2-ethoxy-N-(2-oxo-5-phenyl-2,3-dihydro-1H-benzo[e][1,4]diazepin-3-yl)-benzamide This material was prepared as described for Example 27 except that 5-acetyl-2-ethoxy-benzoic acid (41 mg) was used. The title compound was a colourless solid (45 mg).
$^1$H NMR (DMSO, δ) 1.59 (t, 3H), 2.59 (s, 3H), 4.42 (q, 2H), 5.44 (d, 1H), 7.30-7.54 (m, 10H), 8.17 (ddd, 1H), 8.58 (d, 1H), 9.71 (d, 1H), 11.07 (s, 1H).

Example 76b (S)-5-Acetyl-2-ethoxy-N-(2-oxo-5-phenyl-2,3-dihydro-1H-benzo[e][1,4]diazepin-3-yl)-benzamide This material was prepared as described for Example 76b except that 5-acetyl-2-ethoxy-benzoic acid (83 mg) was used. The title compound was a colourless solid (108 mg).
$^1$H NMR (DMSO, δ) 1.59 (t, 3H), 2.59 (s, 3H), 4.42 (q, 2H), 5.44 (d, 1H), 7.30-7.54 (m, 10H), 8.17 (ddd, 1H), 8.58 (d, 1H), 9.71 (d, 1H), 11.07 (s, 1H).

Example 77a

6-Fluoro-4H-benzo[1,3]dioxine-8-carboxylic acid (2-oxo-5-phenyl-2,3-dihydro-1H-benzo[e][1,4]diazepin-3-yl)-benzamide This material was prepared as described for Example 27 except that 6-fluoro-4H-benzo[1,3]dioxine-8-carboxylic acid (36.2 mg) was used. The title compound was a colourless solid (40 mg).
$^1$H NMR (DMSO, δ) 5.02 (s, 2H), 5.42 (d, 1H), 5.54 (s, 2H), 7.26-7.70 (m, 12H), 9.37 (d, 1H), 11.06 (s, 1H).

Example 77b (S)-6-Fluoro-4H-benzo[1,3]dioxine-8-carboxylic acid (2-oxo-5-phenyl-2,3-dihydro-1H-benzo[e][1,4]diazepin-3-yl)-amide This material was prepared as described for Example 76b except that 6-fluoro-4H-benzo[1,3]dioxine-8-carboxylic acid (86 mg) was used. The title compound was a colourless solid (65 mg)
$^1$H NMR (DMSO, δ) 5.02 (s, 2H), 5.42 (d, 1H), 5.54 (s, 2H), 7.26-7.70 (m, 12H), 9.37 (d, 1H), 11.06 (s, 1H).

Example 78

(S)-2-Methoxy-N-(2-oxo-5-phenyl-2,3-dihydro-1H-benzo[e][1,4]diazepin-3-yl)-4-trifluoromethyl-benzamide This material was prepared as described for Example 76b except that 2-methoxy-4-trifluoromethyl-benzoic acid (26 mg) was used. The title compound was a colourless solid (32 mg).
$^1$H NMR (DMSO, δ) 4.12 (s, 3H), 5.44 (d, 1H), 7.30-7.68 (m, 11H), 8.09 (d, 1H), 9.59 (d, 1H), 11.06 (s, 1H).

Example 79a 2,4,5-Trifluoro-N-(2-oxo-5-phenyl-2,3-dihydro-1H-benzo[e][1,4]diazepin-3-yl)-benzamide This material was prepared as described for Example 27 except that 2,4,5-trifluoro-benzoic acid (39 mg) was used. The title compound was a colourless solid (56 mg).
$^1$H NMR (DMSO, δ) 5.42 (d, 1H), 7.29-7.85 (m, 11H), 9.43-9.47 (m, 1H), 11.02 (s, 1H).

Example 79b (S)-2,4,5-Trifluoro-N-(2-oxo-5-phenyl-2,3-dihydro-1H-benzo[e][1,4]diazepin-3-yl)-benzamide This material was prepared as described for Example 75b except that 2,4,5-trifluoro-benzoic acid (70 mg) was used. The title compound was a colourless solid (74 mg).
$^1$H NMR (DMSO, δ) 5.42 (d, 1H), 7.29-7.85 (m, 11H), 9.43-9.47 (m, 1H), 11.02 (s, 1H).

Example 80a

2-Hydroxy-N-(2-oxo-5-phenyl-2,3-dihydro-1H-benzo[e][1,4]diazepin-3-yl)-benzamide This material was prepared as described for Example 27 except that 2-hydroxy-benzoic acid (30 mg) was used. The title compound was a colourless solid (40 mg).
$^1$H NMR (DMSO, δ) 5.47 (d, 1H), 6.92 (t, 1H), 7.00 (d, 1H), 7.34-7.66 (m, 10H), 8.01 (dd, 1H), 10.07 (brs, 1H), 11.01 (s, 1H).

Example 80b (S)-2-Hydroxy-N-(2-oxo-5-phenyl-2,3-dihydro-1H-benzo[e][1,4]diazepin-3-yl)-benzamide This material was prepared as described for Example 75b except that 2-hydroxy-benzoic acid (55 mg) was used. The title compound was a colourless solid (63 mg).
$^1$H NMR (DMSO, δ) 5.48 (d, 1H), 6.95(t, 1H), 7.04(d, 1H), 7.28-7.70 (m, 10H), 8.06 (dd, 1H), 9.94 (d, 1H), 11.02 (s, 1H), 11.74 (brs, 1H).

Example 81a

1H-Indole-7-carboxylic acid (2-oxo-5-phenyl-2,3-dihydro-1H-benzo[e][1,4]diazepin-3-yl)-amide This material was prepared as described for Example 27 except that 1H-indole-7-carboxylic acid (35 mg) was used. The title compound was a colourless solid (49 mg).

¹H NMR (DMSO, δ) 5.65 (d, 1H), 6.54 (m, 1H), 7.17-8.10 (m, 13H), 9.56 (d, 1H).

Example 81b (S)-1H-Indole-7-carboxylic acid (2-oxo-5-phenyl-2,3-dihydro-1H-benzo[e][1,4]diazepin-3-yl)-amide This material was prepared as described for Example 75b except that 1H-indole-7-carboxylic acid (64 mg) was used. The title compound was a colourless solid (69 mg).

¹H NMR (DMSO, δ) 5.65 (d, 1H), 6.54 (m, 1H), 7.17-8.10 (m, 13H), 9.56 (d, 1H).

Example 82a

3-Methoxy-naphthalene-2-carboxylic acid (2-oxo-5-phenyl-2,3-dihydro-1H-benzo[e][1,4]diazepin-3-yl)-amide This material was prepared as described for Example 27 except that 3-methoxy-naphthalene-2-carboxylic acid (40 mg) was used. The title compound was a colourless solid (73 mg).

¹H NMR (DMSO, δ) 4.15 (s, 3H), 5.51 (d, 1H), 7.37-7.63 (m, 12H), 7.95 (d, 1H), 8.03 (d, 1H), 8.58 (s, 1H), 9.69 (d, 1H), 11.05 (s, 1H).

Example 82b (S)-3-Methoxy-naphthalene-2-carboxylic acid (2-oxo-5-phenyl-2,3-dihydro-1H-benzo[e][1,4]diazepin-3-yl)-amide This material was prepared as described for Example 75b except that 3-methoxy-naphthalene-2-carboxylic acid (80 mg) was used. The title compound was a colourless solid (113 mg).

¹H NMR (DMSO, δ) 4.15 (s, 3H), 5.51 (d, 1H), 7.31-7.68 (m, 12H), 7.95 (d, 1H), 8.03 (d, 1H), 8.58 (s, 1H), 9.71 (d, 1H), 11.08 (s, 1H).

Using analogous procedures to those outlined above, the following compounds were also prepared:

Example 83

N-[7-Chloro-5-(2-fluoro-phenyl)-2-oxo-2,3-dihydro-1H-benzo[e][1,4]diazepine-3-yl]-4-methoxy-benzamide

Example 84

1-(2-Fluoro-benzyl)-3-(2-oxo-5-phenyl-2,3-dihydro-1H-benzo[e][1,4]diazepin-3-yl)-urea

Example 85

1-(4-Methoxy-benzyl)-3-(2-oxo-5-phenyl-2,3-dihydro-1H-benzo[e][1,4]diazepin-3-yl)-urea

Example 86

1-(3-Methyl-benzyl)-3-(2-oxo-5-phenyl-2,3-dihydro-1H-benzo[e][1,4]diazepin-3-yl)-urea

Example 87

1-(2-Oxo-5-phenyl-2,3-dihydro-1H-benzo[e][1,4]diazepin-3-yl)-3-(4-trifluoromethyl-phenyl)-urea

Example 88

4-Chloro-2-methoxy-N-(2-oxo-5-phenyl-2,3-dihydro-1H-benzo[e][1,4]diazepin-3-yl)-benzamide

Example 89

4-Methoxy-3-nitro-N-(2-oxo-5-phenyl-2,3-dihydro-1H-benzo[e][1,4]diazepin-3-yl)benzamide

Example 90

3-Methoxy-2-nitro-N-(2-oxo-5-phenyl-2,3-dihydro-1H-benzo[e][1,4]diazepin-3-yl)-benzamide

Example 91

5-Chloro-2-methoxy-N-(2-oxo-5-phenyl-2,3-dihydro-1H-benzo[e][1,4]diazepin-3-yl)benzamide

Example 92

5-Fluoro-2-methoxy-N-(2-oxo-5-phenyl-2,3-dihydro-1H-benzo[e][1,4]diazepin-3-yl)-benzamide

Example 93

2-Methoxy-4-nitro-N-(2-oxo-5-phenyl-2,3-dihydro-1H-benzo[e][1,4]diazepin-3-yl)-benzamide

Example 94

5-Methoxy-2-nitro-N-(2-oxo-5-phenyl-2,3-dihydro-1H-benzo[e][1,4]diazepin-3-yl)-benzamide

Example 95

3-Methoxy-4-nitro-N-(2-oxo-5-phenyl-2,3-dihydro-1H-benzo[e][1,4]diazepin-3-yl)-benzamide

Example 96

3-2-Methoxy-phenyl)-N-(2-oxo-5-phenyl-2,3-dihydro-1H-benzo[e][1,4]diazepin-3-yl)propionamide

Example 97

3-(3-Methoxy-phenyl)-N-(2-oxo-5-phenyl-2,3-dihydro-1H-benzo [e][1,4]diazepin-3-yl)-propionamide

Example 98

3-(4-Methoxy-phenyl)-N-(2-oxo-5-phenyl-2,3-dihydro-1H-benzo[e][1,4]diazepin-3-yl)-propionamide

Example 99

N-[5-(3-Chloro-phenyl)-2-oxo-2,3-dihydro-1H-benzo[e][1,4]diazepin-3-yl]-2-methoxy-benzamide

Example 100

N-[5-(3-Chloro-phenyl)-2-oxo-5-phenyl-2,3-dihydro-1H-benzo[e][1,4]diazepin-3-yl]-4-methoxy-benzamide

Example 101

N-[5-(3-Chloro-phenyl)-2-oxo-5-phenyl-2,3-dihydro-1 H-benzo[e][1,4]diazepin-3-yl]-2-nitro-benzamide

Example 102

N-[5-(3-Chloro-phenyl)-2-oxo-5-phenyl-2,3-dihydro-1H-benzo[e][1,4]diazepin-3-yl]-4-nitro-benzamide

Example 103

4-Methoxy-N-[2-oxo-5-(4-trifluoromethyl-phenyl)-2,3-dihydro-1 H-benzo[e][1,4]diazepin-3-yl]-benzamide

Example 104

2-Methoxy-N-[2-oxo-5-(3-trifluoromethyl-phenyl)-2,3-dihydro-1H-benzo[e][1,4]diazepin-3-yl]-benzamide

Example 105

4-Methoxy-N-[2-oxo-5-(3-trifluoromethyl-phenyl)-2,3-dihydro-1H-benzo[e][1,4]diazepin-3-yl]-benzamide

Example 106

2-Ethoxy-N-(2-oxo-5-phenyl-2,3-dihydro-1H-benzo[e][1,4]diazepin-3-yl)-benzamide

Example 107

2,4-Dimethoxy-N-(2-oxo-5-phenyl-2,3-dihydro-1H-benzo[e][1,4]diazepin-3-yl)-benzamide

Example 108

2-Bromo-5-methoxy-N-(2-oxo-5-phenyl-2,3-dihydro-1H-benzo[e][1,4]diazepin-3-yl)-benzamide

Example 109

2-Methoxy-N-[5-(3-methoxy-phenyl)-2-oxo-2,3-dihydro-1H-benzo[e][1, 4]diazepin-3-yl]-benzamide

Example 110

N-[5-(3-Methoxy-phenyl)-2-oxo-5-phenyl-2,3-dihydro-1H-benzo[e][1,4]diazepin-3-yl]-nitro-benzamide

Example 111

2-Methoxy-N-(8-methyl-2-oxo-5-phenyl-2,3-dihydro-1H-benzo[e][1,4]diazepin-3-yl)-benzamide

Example 112

2-Chloro-4-methanesulfonyl-N-(2-oxo-5-phenyl-2,3-dihydro-1H-benzo[e][1,4]diazepin-3-yl)-benzamide

Example 113

2-Dimethylamino-N-(2-oxo-5-phenyl-2,3-dihydro-1H-benzo[e][1,4]diazepin-3-yl)-benzamide

Example 114

(2-Oxo-5-phenyl-2,3-dihydro-1H-benzo[e][1,4]diazepin-3-yl)-carbamic acid benzyl ester

Example 115

1-(3,5-Dimethyl-phenyl)-3-(2-oxo-5-phenyl-2,3-dihydro-1H-benzo [e][1,4]diazepin-3-yl)-urea

Example 116

1-(2-Oxo-5-phenyl-2,3-dihydro-1H-benzo[e][1,4]diazepin-3-yl)-3-(4-trifluoromethoxy-phenyl)-urea

Example 117

1-(4-Bromo-2-trifluoromethyl-phenyl)-3-(2-oxo-5-phenyl-2,3-dihydro-1H-benzo[e][1,4]diazepin-3-yl)-urea

Example 118

1-(4-Bromo-benzyl)-3-(2-oxo-5-phenyl-2,3-dihydro-1H-benzo[e][1,4]diazepin-3-yl)-urea

Example 119

1-(2,3-Dichloro-phenyl)-3-(2-oxo-5-phenyl-2,3-dihydro-1H-benzo[e][1,4]diazepin-3-yl)-urea

Example 120

1-(2,6-Dimethyl-phenyl)-3-(2-oxo-5-phenyl-2,3-dihydro-1H-benzo[e][1,4]diazepin-3-yl)-urea

Example 121

1-(2-Chloro-6-methyl-phenyl)-3-(2-oxo-5-phenyl-2,3-dihydro-1H-benzo[e][1,4]diazepin-3-yl)-urea

Example 122

1-(4-Nitro-phenyl)-3-(2-oxo-5-phenyl-2,3-dihydro-1H-benzo[e][1,4]diazepin-3-yl)-urea

Example 123

1-(2-Methylsulfanyl-phenyl)-3-(2-oxo-5-phenyl-2,3-dihydro-1H-benzo[e][1,4]diazepin-3-yl)-urea

Example 124

1-(2,6-Dichloro-phenyl)-3-(2-oxo-5-phenyl-2,3-dihydro-1H-benzo[e][1,4]diazepin-3-yl)-urea

Example 125

5-tert-Butyl-2-methoxy-N-(2-oxo-5-phenyl-2,3-dihydro-1H-benzo[e][1,4]diazepin-3-yl)-benzamide

Example 126

2,5-Dimethoxy-N-(2-oxo-5-phenyl-2,3-dihydro-1H-benzo[e][1,4]diazepin-3-yl)-benzamide

Example 127

1-(2,6-Difluoro-phenyl)-3-(2-oxo-5-phenyl-2,3-dihydro-1H-benzo[e][1,4]diazepin-3-yl)-urea

Example 128

1-(3-Fluoro-phenyl)-3-(2-oxo-5-phenyl-2,3-dihydro-1H-benzo[e][1,4]diazepin-3-yl)-urea

Example 129

1-(3-Methoxy-phenyl)-3-(2-oxo-5-phenyl-2,3-dihydro-1H-benzo[e][1,4]diazepin-3-yl)-urea

Example 130

1-(2-Oxo-5-phenyl-2,3-dihydro-1H-benzo[e][1,4]diazepin-3-yl)-3-(3-trifluoromethyl-phenyl)-urea

Example 131

1-(3-Chloro-phenyl)-3-(2-oxo-5-phenyl-2,3-dihydro-1H-benzo[e][1,4]diazepin-3-yl)-urea

Example 132

2-Methoxy-4-methylsulfanyl-N-(2-oxo-5-phenyl-2,3-dihydro-1H-benzo[e][1,4]diazepin-3-yl)-benzamide

Example 133

4-Methanesulfonyl-N-(2-oxo-5-phenyl-2,3-dihydro-1H-benzo[e][1,4]diazepin-3-yl)-benzamide

Example 134

N-(2-Oxo-5-phenyl-2,3-dihydro-1H-benzo[e][1,4]diazepin-3-yl)terephthalamic acid methyl ester

Example 135

2-Fluoro-N-(2-oxo-5-phenyl-2,3-dihydro-1H-benzo[e][1,4]diazepin-3-yl)-benzamide

Example 136

2,6-Difluoro-N_(2-oxo-5-phenyl-2,3-dihydro-1H-benzo[e][1,4]diazepin-3-yl)-benzamide

Example 137

N-(2-Oxo-5-phenyl-2,3-dihydro-1H-benzo[e][1,4]diazepin-3-yl)-2-propoxy-benzamide

Example 138

2-Iodo-N-(2-oxo-5-phenyl-2,3-dihydro-1H-benzo[e][1,4]diazepin-3-yl)-benzamide

Example 139

3-Methoxy-N-(2-oxo-5-phenyl-2,3-dihydro-1H-benzo[e][1,4]diazepin-3-yl)-terephthalamic acid methyl ester

Example 140

4-Amino-5-chloro-2-methoxy-N-(2-oxo-5-phenyl-2,3-dihydro-1H-benzo[e][1,4]diazepin-3-yl)-benzamide

Example 141

1-(2-Oxo-5-phenyl-2,3-dihydro-1H-benzo[e][1,4]diazepin-3-yl)-3-m-tolyl-urea

Example 142

2-Methylsulfanyl-N-(2-oxo-5-phenyl-2,3-dihydro-1H-benzo[e][1,4]diazepin-3-yl)-benzamide

Example 143

2-Methoxy-N-(2-oxo-5-phenyl-2,3-dihydro-1H-benzo[e][1,4]diazepin-3-yl)-5-sulfamoyl-benzamide

Example 144

2-Hydroxy-N-(2-oxo-5-phenyl-2,3-dihydro-1H-benzo[e][1,4]diazepin-3-yl)3-phenyl-propionamide

Example 145

3-Hydroxy-N-(2-oxo-5-phenyl-2,3-dihydro-1H-benzo[e][1,4]diazepin-3-yl)-3-phenyl-propionamide

Example 146

3-(2-Fluoro-phenyl)-1-methyl-1-(2-oxo-5-phenyl-2,3-dihydro-1H-benzo[e][1,4]diazepin-3-yl)-urea

Example 147

2-Methoxy-N-methyl-4-nitro-N-(2-oxo-5-phenyl-2,3-dihydro-1H-benzo[e][1,4]diazepin-3-yl)-benzamide

Example 148

1-tert-Butyl-3-(2-oxo-5-phenyl-2,3-dihydro-1H-benzo[e][1,4]diazepin-3-yl)-urea

Example 149

1-Cyclohexyl-3-(2-oxo-5-phenyl-2,3-dihydro-1H-benzo[e][1,4]diazepin-3-yl)-urea

Example 150

1-Ethyl-3-(2-oxo-5-phenyl-2,3-dihydro-1H-benzo[e][1,4]diazepin-3-yl)-urea

Example 151

1-Butyl-3-(2-oxo-5-phenyl-2,3-dihydro-1H-benzo[e][1,4]diazepin-3-yl)-urea

Example 152

4,5-Dimethyl-furan-2-carboxylic acid (2-oxo-5-phenyl-2,3-dihydro-1H-benzo[e][1,4]diazepin-3-yl) amide

Example 153

Piperidine-1-carboxylic acid (7-chloro-2-oxo-5-phenyl-2,3-dihydro-1H-benzo[e][1,4]diazepin-3-yl)-amide

Example 154

N-[5-(3-Chloro-phenyl)-2-oxo-5-phenyl-2,3-dihydro-1H-benzo[e][1,4]diazepin-3-yl]-acetamide

Example 155

N-[5-(3-Chloro-phenyl)-2-oxo-5-phenyl-2,3-dihydro-1H-benzo[e][1,4]diazepin-3-yl]-isobutyramide

Example 156

Furan-2-carboxylic acid [5-(3-chloro-phenyl)-2-oxo-5-phenyl-2,3-dihydro-1H-benzo[e][1,4]diazepin-3-yl]-amide

Example 157

Thiophene-2-carboxylic acid [5-(3-chloro-phenyl)-2-oxo-5-phenyl-2,3-dihydro-1H-benzo[e][1,4]diazepin-3-yl]-amide

Example 158

Cyclohexanecarboxylic acid [5-(3chloro-phenyl)-2-oxo-5-phenyl-2,3-dihydro-1H-benzo[e][1,4]diazepin-3-yl]-amide

Example 159

Piperidine-1-carboxylic acid [5-(3-chloro-phenyl)-2-oxo-5-phenyl-2,3-dihydro-1H-benzo[e][1,4]diazepin-3-yl]-amide

Example 160

N-[5-(3-Chloro-phenyl)-2-oxo-5-phenyl-2,3-dihydro-1H-benzo[e][1,4]diazepin-3-yl]isonicotinamide

Example 161

5-Methyl-furan-2-carboxylic acid (2-oxo-5-phenyl-2,3-dihydro-1H-benzo[e][1,4]diazepin-3-yl)-amide

Example 162

Pyrazine-2-carboxylic acid (2-oxo-5-phenyl-2,3-dihydro-1H-benzo[e][1,4]diazepin-3-yl)-amide

Example 163

N-[5-(3-Methoxy-phenyl)-2-oxo-5-phenyl-2,3-dihydro-1H-benzo[e][1,4]diazepin-3-yl]-isobutyramide

Example 164

Thiophene-2-carboxylic acid [5-(3-methoxy-phenyl)-2-oxo-5-phenyl-2,3-dihydro-1H-benzo[e][1,4]diazepin-3-yl]-amide

Example 165

Cyclohexanecarboxylic acid [5-(3-methoxy-phenyl)-2-oxo-5-phenyl-2,3-dihydro-1H-benzo[e][1,4]diazepin-3-yl]-amide

Example 166

Piperidine-1-carboxylic acid [5-(3-methoxy-phenyl)-2-oxo-5-phenyl-2,3-dihydro-1H-benzo[e][1,4]diazepin-3-yl]-amide

Example 167

Piperidine-4-carboxylic acid [5-(3-methoxy-phenyl)-2-oxo-5-phenyl-2,3-dihydro-1H-benzo[e][1,4]diazepin-3-yl]-amide

Example 168

Cyclohexanecarboxylic acid (8-chloro-2-oxo-5-phenyl-2,3-dihydro-1H-benzo[e][1,4]diazepin-3-yl)-amide

Example 169

Thiophene-2-carboxylic acid (8-methyl-2-oxo-5-phenyl-2,3-dihydro-1H-benzo[e][1,4]diazepin-3-yl)-amide

Example 170

1-(2-Oxo-5-phenyl-2,3-dihydro-1H-benzo[e][1,4]diazepin-3-yl)-3-thiophene-2-yl-urea

Example 171

1-(2-Oxo-5-phenyl-2,3-dihydro-1H-benzo[e][1,4]
diazepin-3-yl)-3-thiophene-3-yl-urea

Example 172

Pyridine-2-carboxylic acid (2-oxo-5-phenyl-2,3-
dihydro-1H-benzo[e][1,4]diazepin-3-yl)-amide

Example 173

1H-Pyrazole-4-carboxylic acid (2-oxo-5-phenyl-2,3-
dihydro-1H-benzo[e][1,4]diazepin-3-yl)-amide

Example 174

6-Dimethylamino-N-(2-oxo-5-phenyl-2,3-dihydro-
1H-benzo[e][1,4]diazepin-3-yl)-nicotinamide

Example 175

2-Ethoxy-naphthalene-1-carboxylic acid (2-oxo-5-
phenyl-2,3-dihydro-1H-benzo[e][1,4]diazepin-3-yl)-
amide

Example 176

9-Oxo-9H-fluorene-1-carboxylic acid (2-oxo-5-phe-
nyl-2,3-dihydro-1H-benzo[e][1,4]diazepin-3-yl)-
amide

Example 177

2-Oxo-2,3-dihydro-benzoimidazole-1-carboxylic
acid (2-oxo-5-phenyl-2,3-dihydro-1H-benzo[e][1,4]
diazepin-3-yl)-amide

Example 178

(2-Oxo-5-phenyl-2,3-dihydro-1H-benzo[e][1,4]diaz-
epin-3-yl)carbamic acid tert-butyl ester

Example 179

(S)-4,5-Dibromo-furan-2-carboxylic acid (2-oxo-5-
phenyl-2,3-dihydro-1H-benzo[e][1,4]diazepin-3-yl)-
amide

Example 180

(S)-Benzofuran-2-carboxylic acid (2-oxo-5-phenyl-
2,3-dihydro-1H-benzo[e][1,4]diazepin-3-yl)-amide

Example 181

(2-Oxo-5-phenyl-2,3-dihydro-1H-benzo[e][1,4]diaz-
epin-3-yl)-carbamic acid methyl ester

Example 182

(2-Oxo-5-phenyl-2,3-dihydro-1H-benzo[e][1,4]diaz-
epin-3-yl)-carbamic acid ethyl ester

Example 183

(2-Oxo-5-phenyl-2,3-dihydro-1H-benzo[e][1,4]diaz-
epin-3-yl)-carbamic acid isobutyl ester

Example 184

2-Oxo-N-(2-oxo-5-phenyl-2,3-dihydro-1H-benzo[e]
[1,4]diazepin-3-yl)-2-thiophene-2-yl-acetamide

Activity Example 1

Examples 1 to 74 and 83 to 124 were tested using the following protocol.

XTT Assay Protocol

The inner 60 wells of 96 well tissue culture plates were seeded with Vero cells at $3\times10^4$ cells/well ($1\times10^4$ cells/well for toxicity studies) in 100 or 150 µl of medium and incubated at 37° C. overnight or until nearing confluency. For primary screen, 25 µl compounds were added directly to 100 µl medium in single wells to duplicate plates. A third plate was prepared for simultaneous toxicity investigation.

For follow-up investigation, 70 µl of compound in duplicate wells were added directly to culture medium at 3.2× final concentration and ½ log serially diluted down columns of plate. A duplicate plate was prepared for simultaneous toxicity investigation.

Cells were infected with 25 µl RSV to give m.o.i.≈0.2. Some 100 µl of sterile distilled water were added to the outer wells of the plate and incubated at 33° C. for 6 days. Some 0.25 µl/ml PMS were added to stock ITT solution, final conc. 25 µM PMS. Then 25 µl warmed XTT/PMS solution were added to each well and incubated for 5 hours at 37° C. Plates were shaken (DynaTech Vari-Shaker) vigorously for 10 mins and allowed to cool for 15 mins before sealing. Absorbance at 450 nM was measured and data analysed using Microsoft Excel software.

Maximum $OD_{450nm}$ reading (uninfected, untreated control cells) corresponded to 100% inhibition. Minimum $OD_{450nm}$ readings (infected control cells) corresponded to 0% inhibition. Log 10 concentration was plotted against $OD_{450nm}$ and $IC_{50}$ (Table 1) values were calculated from either reading 50% value from graph or using regression analysis.

Examples 75 to 82 and 125 to 184 were tested according to the protocol described below.

XTT Assay Protocol

The inner 60 wells of 96 well tissue culture plates were seeded with Hep-2 cells at $4\times10^4$ cells/well for compound activity and toxicity studies in 100 µl of medium and incubated at 37° C. overnight or until nearing confluency.

Cells were infected with 25 µl RSV previously tritrated to give 80% cell kill. To each well 25 µM of test compound were added. The final DMSO concentration was 0.5%. Some 200 µl of sterile distilled water were added to the outer wells of the plate and incubated at 37° C. for 6 days. Some 0.25 µl/ml PMS were added to stock XT solution, final conc. 25 µM PMS. Then 25 µl warmed XTT/PMS solution were added to each well and incubated for 1 hour at 37° C.

Maximum $OD_{450nm}$ reading (uninfected, untreated control cells) corresponded to 100% inhibition. Minimum $OD_{450nm}$ readings (infected control cells) corresponded to 0% inhibition. Log 10 concentration was plotted against $OD_{450nm}$ and IC$_{50}$ values were calculated from either reading 50% value from graph or using regression analysis.

The LC-MS data for Examples 75a to 184 is also shown in Table 2.

TABLE 1

| Example | XTT IC50 (uM) | TD50 (2d) | TD50 (6d) |
|---|---|---|---|
| 1 | | | |
| 2 | 4 | | |
| 3 | 2.5 | | |
| 4 | 5 | | |
| 5 | 2.5 | | |
| 6 | 6 | | |
| 7 | 2 | | |
| 8 | 2 | | |
| 9 | 2 | 70 | 100 |
| 10 | 1.5 | | |
| 11 | 0.5 | 100 | |
| 12 | 2.5 | | |
| 13 | 1.5 | 100 | |
| 14 | 1.5 | 100 | |
| 15 | 1 | | |
| 16 | 2 | | |
| 17 | 5 | | |
| 18 | 2 | | |
| 19 | 2 | 100 | 100 |
| 20 | 25 | | |
| 21 | 6 | 100 | 100 |
| 22 | 4 | | |
| 23 | 5 | | |
| 24 | 3 | | |
| 25 | 2 | | |
| 26 | 2 | | |
| 27a | 0.3 | 100 | |
| 27b | <0.3 | | >100 |
| 28 | 5 | | |
| 29 | 2 | | |
| 30 | 3 | | |
| 31 | 5 | | |
| 32 | 2 | | |
| 33 | 2.5 | | |
| 34 | 3 | | |
| 35 | 6 | | |
| 36 | 15 | | |
| 37 | 15 | | |
| 38 | 6 | 50 | 40 |
| 39 | 10 | 60 | 50 |
| 40 | 10 | 50 | 15 |
| 41 | 10 | 100 | 100 |
| 42 | 20 | | |
| 43 | 30 | | |
| 44 | 10 | | |
| 45 | 20 | | |
| 46 | 30 | | |
| 47 | 30 | 100 | 50 |
| 48 | | 100 | 50 |
| 49 | 50 | 100 | 100 |
| 50 | 50 | | |
| 51 | 5 | | |
| 52 | 3 | | |
| 53 | 5 | | |
| 54 | 1.5 | | 30 |
| 55 | 3 | | 30 |
| 56 | 5 | | |
| 57 | 0.7 | | |
| 58 | 1.2 | | 30 |
| 59 | 5 | | |
| 60 | 5 | | |
| 61 | 3 | | |
| 62 | 1.5 | | |
| 63 | 1.7 | | |
| 64 | 1 | | |
| 65 | 2 | | 100 |
| 66 | 1.5 | | 30 |
| 67 | 1.5 | | 100 |
| 68 | 1 | | |
| 69 | 1.5 | | |
| 70 | 1.5 | | 100 |
| 71 | 3 | | 50 |

TABLE 1-continued

| Example | XTT IC50 (uM) | TD50 (2d) | TD50 (6d) |
|---|---|---|---|
| 72 | 1.5 | | 100 |
| 73a | 1 | | 100 |
| 73b | 0.7 | | >50 |
| 74 | 1.5 | | 100 |

TABLE 2

| Example No | LC-MS data RT/min | LC-MS data ES | XTT IC50 (uM) | TC50 (2d) | TC50 (6d) |
|---|---|---|---|---|---|
| 75a | 4.82 | ES + 464.33 | 2.4 | | |
| 75b | 4.83 | ES + 464 | 0.6 | | >50 |
| 76a | 5.2 | 492 | 3.5 | | 64 |
| 76b | 4.81 | ES + 442.49 | 1.2 | | >50 |
| 77a | 5.28 | ES + 432 | 4.6 | | >50 |
| 77b | 4.85 | ES + 432.46 | 0.5 | | 33.2 |
| 78 | 5.62 | ES + 454 | 2.7 | | 32.5 |
| 79a | | | 8 | | 65 |
| 79b | 5.03 | ES + 410.44 | 5.8 | | >50 |
| 80a | | | 8.7 | | 33 |
| 80b | 4.83 | ES + 372.50 | 2 | | >50 |
| 81a | 5.39 | ES + 395.46 | 8.4 | | 63 |
| 81b | 5.01 | ES + 395.46 | 1.2 | | 35.6 |
| 82a | | | 6.7 | | >50 |
| 82b | 5.21 | ES + 436.49 | 1.5 | | >50 |
| 83 | 5.37 | 438.44, 436.39 | 6 | >100 | 32 |
| 84 | 4.74 | ES + 403.54 | 2 | >100 | >100 |
| 85 | 4.6 | ES + 415.54 | 4 | >100 | >100 |
| 86 | 4.95 | ES + 399.59 | 3 | >100 | 100 |
| 87 | 5.68 | ES + 439.51 | 4 | 50 | 50 |
| 88 | 5.64 | ES + 420, 422 | 0.3 | 100 | 40 |
| 89 | 5.19 | ES + 431 | 0.8 | >100 | >100 |
| 90 | 5.11 | ES + 431 | 0.5 | 100 | 100 |
| 91 | 5.65 | ES + 420, 422 | 0.3 | 100 | 100 |
| 92 | 5.32 | ES + 404 | <0.3 | 100 | 100 |
| 93 | 5.44 | ES + 431 | <0.3 | 100 | >100 |
| 94 | 4.91 | ES + 431 | 1.5 | >100 | >100 |
| 95 | 5.51 | ES + 431 | 1.5 | 100 | >100 |
| 96 | 5.3 | ES + 414.54 | 5 | >100 | >100 |
| 97 | 5.14 | ES + 414.55 | 5 | >100 | >100 |
| 98 | 5.17 | ES + 414.54 | 5 | >100 | >100 |
| 99 | 5.69 | ES + 420.49 | 1 | 100 | >100 |
| 100 | 5.58 | ES + 420.48 | 4 | >100 | 100 |
| 101 | 5.36 | ES + 435.45 | 2.5 | 100 | 100 |
| 102 | 5.79 | ES + 435.46 | 7 | >100 | >100 |
| 103 | 5.69 | ES + 454.47 | 7 | >100 | 30 |
| 104 | 5.69 | ES + 454.48 | 5 | >100 | >100 |
| 105 | 5.6 | ES 454.49 | 9 | >100 | >100 |
| 106 | 5.7 | ES + 400 | 0.7 | >100 | >100 |
| 107 | 5.33 | ES − 414 | <0.3 | 60 | 60 |
| 108 | 5.32 | ES + 464, 466 | 2 | >100 | >100 |
| 109 | 509 | ES + 416.54 | 2 | 50 | 50 |
| 110 | 5.21 | ES + 431.53 | 5 | >100 | >100 |
| 111 | 5.29 | ES + 400.49 | 3 | >100 | >100 |
| 112 | 4.87 | ES + 468 | 1.5 | >100 | >100 |
| 113 | 4.69 | ES + 399 | 1.5 | >100 | >100 |
| 114 | 5.37 | ES + 386 | 5 | >100 | 60 |
| 115 | 5.32 | ES + 399.50 | 1.5 | >100 | 60 |
| 116 | 5.49 | ES + 455.45 | 2 | 20 | 20 |
| 117 | 5.67 | ES + 517.33, 519.33 | 6 | 60 | 100 |
| 118 | 5.14 | ES + 463.41, 465.41 | 2 | >100 | 100 |
| 119 | 5.54 | ES + 439.40 | 2 | >100 | 30 |
| 120 | 4.98 | ES + 399.55 | 6 | >100 | 60 |
| 121 | 5.02 | ES + 416.49 | 4 | 60 | 60 |
| 122 | 5.2 | ES + 416.49 | 0.4 | 60 | 20 |
| 123 | 5.2 | 417.48 | 2 | >100 | 100 |
| 124 | 5.02 | ES439.41 | 5 | 70 | 60 |
| 125 | 5.84 | ES + 442.54 | 6.1 | | >50 |
| 126 | 4.61 | ES + 416.44 | 5.4 | | >50 |
| 127 | 4.35 | ES + 407.44 | 9.4 | | >50 |
| 128 | 4.65 | ES + 389.46 | 6.1 | | >50 |
| 129 | 4.53 | ES + 401.47 | 4.9 | | >50 |
| 130 | 4.95 | ES − 437.35 | 9.7 | | 39.5 |

TABLE 2-continued

| Example No | LC-MS data RT/min | ES | XTT IC50 (uM) | TC50 (2d) | TC50 (6d) |
|---|---|---|---|---|---|
| 131 | 4.82 | ES + 405.44 | 9.6 | | >50 |
| 132 | 5.39 | ES + 389 | 6.3 | | >50 |
| 133 | 4.26 | ES + 432 | 6.2 | | 77.2 |
| 134 | 4.77 | ES + 414 | 6.5 | | 77.1 |
| 135 | 5.2 | ES + 374.42 | 9.5 | | >50 |
| 136 | 5.07 | ES + 392.42 | 8.7 | | >50 |
| 137 | 5.65 | ES + 414.46 | 8.3 | | >50 |
| 138 | 5.25 | 482 | 8.3 | | 51 |
| 139 | 4.99 | ES + 400 | 9.2 | | 98 |
| 140 | 5.03 | ES + 435.45 | 2.5 | | 68 |
| 141 | 4.82 | ES + 412.50 | 4.3 | | >50 |
| 142 | 4.78 | ES + 402.50 | 9.4 | | >50 |
| 143 | 4.3 | ES − 463 | 3.8 | >50 | |
| 144 | 4.54 | ES + 400 | 5.5 | >50 | |
| 145 | 4.39 | ES + 400 | 1.9 | >50 | |
| 146 | 5.08 | ES − 401 | 9.5 | >50 | |
| 147 | 5.02 | ES + 445 | 15.9 | >50 | |
| 148 | 4.56 | ES − 349.57 | 5 | >100 | >100 |
| 149 | 4.76 | ES + 377.57 | 1.5 | >100 | >100 |
| 150 | 3.87 | ES + 345.55 | 2 | >100 | >100 |
| 151 | 4.43 | ES + 351.58 | 1.5 | >100 | >100 |
| 152 | 5.17 | ES + 374 | 0.3 | >100 | 100 |
| 153 | 5.01 | ES + 397.52 | 5 | >100 | >100 |
| 154 | 4.31 | ES + 328.49 | 3 | >100 | >100 |
| 155 | 4.95 | ES + 356.51 | 6 | >100 | >100 |
| 156 | 5.17 | ES + 380.46 | 1.5 | 100 | 100 |
| 157 | 5.51 | ES + 396.45 | 5 | >100 | 100 |
| 158 | 5.74 | ES + 396.53 | 2 | 100 | >100 |
| 159 | 5.15 | ES + 397.52 | 2 | >100 | >100 |
| 160 | 4.44 | ES + 391.48 | 10 | >100 | >100 |
| 161 | 5.52 | ES + 414 | 2 | 100 | 60 |
| 162 | 4.43 | ES + 358 | 2 | >100 | >100 |
| 163 | 4.67 | ES + 352.51 | 5 | >100 | >100 |
| 164 | 5 | ES + 392.56 | 4 | 100 | 100 |
| 165 | 5.14 | ES + 392.56 | 2 | >100 | >100 |
| 166 | 4.77 | ES + 393.57 | 5 | >100 | >100 |
| 167 | 4.42 | 387.52 | 9 | >100 | >100 |
| 168 | 5.43 | ES + 396.53 | 5 | >100 | >100 |
| 169 | 5.18 | ES + 376.44 | 5 | 50 | 30 |
| 170 | 4.42 | ES + 377.40 | 3.4 | | >50 |
| 171 | 4.43 | ES + 377.40 | 4.8 | | >50 |
| 172 | 4.61 | ES + 357 | 6.4 | | 137.8 |
| 173 | 4.66 | ES + 346 | 8.3 | | 95 |
| 174 | 4.06 | ES + 400.46 | 6.9 | | 60 |
| 175 | 5.5 | ES + 450.50 | 8.2 | | >50 |
| 176 | 5.82 | ES + 458.46 | 4.3 | | 99 |
| 177 | 5.17 | ES + 412.50 | 4.3 | | >50 |
| 178 | | | 4.3 | | >50 |
| 179 | 5.17 | ES + 504.20 | 3.9 | | >50 |
| 180 | 5.01 | ES + 396.46 | 2.6 | | 37.1 |
| 181 | 4.23 | ES + 310.55 | 9.6 | | >50 |
| 182 | 4.47 | ES + 324.46 | 10 | | >50 |
| 183 | 4.89 | ES + 352.48 | 9.88 | | >50 |
| 184 | 5 | 390 | 9.5 | | >50 |

What is claimed is:

1. A compound of formula (Ic), or a pharmaceutically acceptable salt thereof,

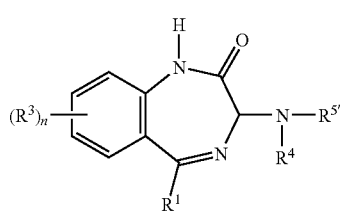

(Ic)

wherein:

$R^1$ is phenyl;

$R^3$ is methyl or chlorine;

n is 0 or 1;

$R^4$ is hydrogen or methyl;

$R^{5\prime}$ is —X';

X' is —CONR'R" and each R'R" is the same or different and represents hydrogen, $C_{1-4}$ alkyl, phenyl, thienyl, cyclohexyl, cyclopentyl or phenyl-$(CH_2)$—;

wherein:

the phenyl moiety in the group $R^1$ being unsubstituted or substituted by a single $C_{1-2}$ alkyl, $C_{1-2}$ alkoxy, $C_{1-2}$ alkylthio, $C_{1-2}$ haloalkyl or $C_{1-2}$ haloalkoxy substituent;

the phenyl, thienyl, cyclohexyl, cyclopentyl or phenyl-$(CH_2)$— moieties in the R' and R" being unsubstituted or substituted by one or two substituents selected from fluorine, chlorine, bromine, and nitro.

2. A compound of formula (Ie) or pharmaceutically acceptable salts thereof

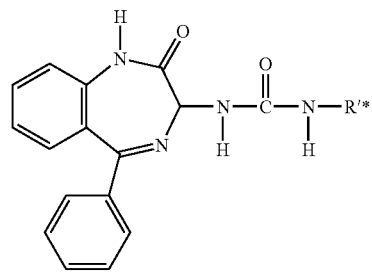

(Ie)

wherein R'* is an aryl group which is unsubstituted or substituted by 1 or 2 substituents selected from fluorine, chlorine, bromine, and nitro.

3. A compound according to claim 1, selected from 1,1-Diethyl-3-(2-oxo-5-phenyl-2,3-dihydro-1H-benzo[e][1,4]diazepin-3-yl)-urea;

(S)-1-(2-Fluoro-phenyl)-3-(2-oxo-5-phenyl-2,3-dihydro-1H-benzo[e][1,4]diazepin-3-yl)-urea;

1-(4-Nitro-phenyl)-3-(2-oxo-5-phenyl-2,3-dihydro-1H-benzo[e][1,4]diazepin-3-yl)-urea;

1-tert-Butyl-3-(2-oxo-5-phenyl-2,3-dihydro-1H-benzo[e][1,4]diazepin-3-yl)-urea;

1-Cyclohexyl-3-(2-oxo-5-phenyl-2,3-dihydro-1H-benzo[e][1,4]diazepin-3-yl)-urea;

1-Ethyl-3-(2-oxo-5-phenyl-2,3-dihydro-1H-benzo[e][1,4]diazepin-3-yl)-urea;

1-Butyl-3-(2-oxo-5-phenyl-2,3-dihydro-1H-benzo[e][1,4]diazepin-3-yl)-urea;

or a pharmaceutically acceptable salt thereof.

4. The compound of claim 2, wherein R'* is a phenyl group which is unsubstituted or substituted by a single fluorine, chlorine, or bromine substituent.

5. A compound according to claim 2, wherein the compound is (S)-1-(2-Fluoro-phenyl)-3-(2-oxo-5-phenyl-2,3-dihydro-1H-benzo[e][1,4]diazepin-3-yl)-urea.

6. A compound according to claim 2, wherein the compound is 1-(4-Nitro-phenyl)-3-(2-oxo-5-phenyl-2,3-dihydro-1H-benzo[e][1,4]diazepin-3-yl)-urea.

7. A compound according to claim 2, wherein the compound is 1-Butyl-3-(2-oxo-5-phenyl-2,3-dihydro-1H-benzo[e][1,4]diazepin-3-yl)-urea.

8. A compound according to claim 1 wherein the compound is 1,1-Diethyl-3-(2-oxo-5-phenyl-2,3-dihydro-1H-benzo[e][1,4]diazepin-3-yl)-urea.

9. A compound according to claim 2, wherein the compound is 1-tert-Butyl-3-(2-oxo-5-phenyl-2,3-dihydro-1H-benzo[e][1,4]diazepin-3-yl)-urea.

10. A compound according to claim 1, wherein $R^1$ is phenyl.

* * * * *

UNITED STATES PATENT AND TRADEMARK OFFICE
CERTIFICATE OF CORRECTION

| | | |
|---|---|---|
| PATENT NO. | : 7,582,624 B2 | Page 1 of 1 |
| APPLICATION NO. | : 10/528250 | |
| DATED | : September 1, 2009 | |
| INVENTOR(S) | : Carter et al. | |

It is certified that error appears in the above-identified patent and that said Letters Patent is hereby corrected as shown below:

On the Title Page

Item [*] Notice:   Subject to any disclaimer, the term of this patent is extended or adjusted under 35 USC 154(b) by 238 days Delete the phrase "by 238 days" and insert -- by 367 days --

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,582,624 B2 Page 1 of 1
APPLICATION NO. : 10/528250
DATED : September 1, 2009
INVENTOR(S) : Carter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this

Fourteenth Day of September, 2010

David J. Kappos
*Director of the United States Patent and Trademark Office*